(12) United States Patent
Lim et al.

(10) Patent No.: US 10,040,802 B2
(45) Date of Patent: Aug. 7, 2018

(54) THIENOPYRAZINE INHIBITORS OF IRAK4 ACTIVITY

(71) Applicant: MERCK SHARP & DOHME CORP., Rahway, NJ (US)

(72) Inventors: Jongwon Lim, Lexington, MA (US); Michael D. Altman, Needham, MA (US); Craig R. Gibeau, Holliston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/557,206

(22) PCT Filed: Mar. 7, 2016

(86) PCT No.: PCT/US2016/021125
§ 371 (c)(1),
(2) Date: Sep. 11, 2017

(87) PCT Pub. No.: WO2016/144849
PCT Pub. Date: Sep. 15, 2016

(65) Prior Publication Data
US 2018/0051035 A1    Feb. 22, 2018

Related U.S. Application Data

(60) Provisional application No. 62/132,174, filed on Mar. 12, 2015.

(51) Int. Cl.
| C07D 495/04 | (2006.01) |
| C07D 519/00 | (2006.01) |
| A61K 45/06  | (2006.01) |
| A61K 31/551 | (2006.01) |
| A61K 31/55  | (2006.01) |
| A61K 31/4985 | (2006.01) |

(52) U.S. Cl.
CPC ........ *C07D 495/04* (2013.01); *A61K 31/4985* (2013.01); *A61K 31/55* (2013.01); *A61K 31/551* (2013.01); *A61K 45/06* (2013.01); *C07D 519/00* (2013.01)

(58) Field of Classification Search
CPC .... C07D 495/04; C07D 519/00; A61K 45/06; A61K 31/551; A61K 31/55
See application file for complete search history.

(56) References Cited

U.S. PATENT DOCUMENTS

| 2009/0203667 A1 | 8/2009  | Nakasato et al. |
| 2013/0065882 A1 | 3/2013  | Machinaga et al. |
| 2014/0303149 A1 | 10/2014 | Arora et al. |

FOREIGN PATENT DOCUMENTS

EP    0573360    8/1998

OTHER PUBLICATIONS

RN 1462236-71-0, 2013, registry abstract.*
Lim et al., Bioorganic&Medicinal Chemistry Letters, 25 (2015), 5384-5388.*
Ryder et al., caplus an 1998:268489.*
Pubchem SID 179734810, Feb. 6, 2014, pp. 1-5.

* cited by examiner

*Primary Examiner* — Sun Jae Yoo
(74) *Attorney, Agent, or Firm* — Matthew A. Leff; Laura Ginkel

(57) ABSTRACT

The present invention relates to thienopyrazine inhibitors of IRAK4 of formula (I) and provides compositions comprising such inhibitors, as well as methods therewith for treating IRAK4-mediated or -associated conditions or diseases.

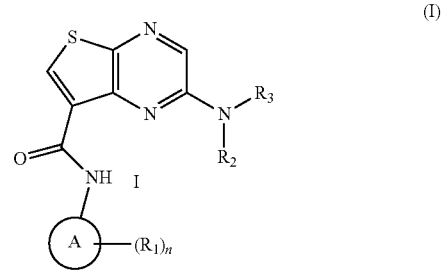

4 Claims, No Drawings

THIENOPYRAZINE INHIBITORS OF IRAK4 ACTIVITY

BACKGROUND OF THE INVENTION

The present invention is directed to compounds which modulate interleukin-1 (IL-1) receptor-associated kinase 4 (IRAK4) and are useful in the prevention or treatment of inflammatory, cell proliferative and immune-related conditions and diseases.

The recruitment of immune cells to sites of injury involves the concerted interactions of a large number of soluble mediators. Several cytokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration observed in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, multiple sclerosis, diabetes, obesity, cancer, sepsis, etc.

The importance of IL-1 in inflammation has been demonstrated by the ability of the highly specific IL-1 receptor antagonist protein (IL-1Ra or IRAP) to relieve inflammatory conditions. See, e.g., Dinarello, Cytokine Growth Factor Rev., 1997, 8:253-265.

IL-1 treatment of cells induces the formation of a complex consisting of the two IL-1 receptor chains, IL-1R1 and IL-1RAcP, and the resulting heterodimer recruits an adaptor molecule designated as MyD88. See e.g., Wesche et al., J. Biol. Chem., 1999, 274:19403-19410. MyD88 binds to a protein designated IRAK (IL-1 receptor associated kinase). See, e.g., O'Neill et al., J. Leukoc. Biol., 1998, 63(6):650-657; Auron, Cytokine Growth Factor Rev., 1998, 9(3-4): 221-237; and O'Neill, Biochem. Soc. Trans., 2000, 28(5): 557-563. IRAK is subsequently phosphorylated and released from the receptor complex to interact with a tumor necrosis factor receptor-associated factor, TRAF6, which transduces the signal to downstream effector molecules. See e.g., Cao et al., Nature, 1996, 383:443-446. TRAF6 can trigger the NIK/IKK kinase cascade to activate the transcription factor NK-kappa B. NF-kappa B regulates a number of genes that, in turn, regulate immune and inflammatory responses.

Four IRAKs have been identified: IRAK1 (see, e.g., Cao et al., Science, 1996, 271:1128-1131), IRAK2 (see, e.g. Muzio et al., Science, 1997, 278:1612-1615), the monomyeloic cell specific IRAKM, also known as IRAK3 (see, e.g., Wesche et al., J. Biol. Chem., 1999, 274:19403-19410), and IRAK4 (see, e.g., PCT Publication No. WO 01/051641). IRAK proteins have been shown to play a role in transducing signals other than those originating from IL-1 receptors, including signals triggered by activation of IL-18 receptors (see, e.g., Kanakaraj et al., J. Exp. Med., 1999, 189(7):1129-1138) and LPS receptors (see, e.g., Yang et al., J. Immunol., 1999, 163:639-643; and Wesche et al., J. Biol. Chem., 1999, 274:19403-19410). Over-expression of IRAK2 and IRAKM has been shown to be capable of reconstituting the response to IL-1 and LPS in an IRAK deficient cell line.

The identification of compounds that inhibit the function of IRAK4 represents an attractive approach to the development of therapeutic agents for the treatment of inflammatory, cell proliferative and immune-related conditions and diseases associated with IRAK4-mediated signal transduction, such as rheumatoid arthritis, inflammatory bowel disease, multiple sclerosis, diabetes, obesity, allergic disease, psoriasis, asthma, graft rejection, cancer, and sepsis.

It is an object of the instant invention to provide novel compounds that are inhibitors of IRAK4.

It is also an object of the present invention to provide pharmaceutical compositions that comprise the novel compounds that are inhibitors of IRAK4.

It is also an object of the present invention to provide a method for treating IRAK4-mediated and associated conditions or diseases that comprises administering such inhibitors of IRAK4 activity.

SUMMARY OF THE INVENTION

The present invention relates to thienopyrazine inhibitors of IRAK4 of formula (I) and provides compositions comprising such inhibitors, as well as methods therewith for treating IRAK4-mediated or -associated conditions or diseases.

DETAILED DESCRIPTION OF THE INVENTION

The compounds of the instant invention are useful in the inhibition of the activity of IRAK4.

An embodiment of the instant invention is illustrated by the Formula I:

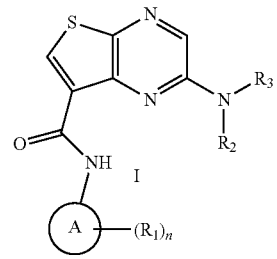

wherein:
Ring A is aryl or heterocyclyl;
n is 0, 1, 2, 3 or 4;
$R_1$ is independently selected from: $(C_1-C_4)$alkyl, $(C_3-C_6)$cycloalkyl, heterocyclyl, $CF_3$, $CHF_2$, CN, halo, said alkyl, cycloalkyl and heterocyclyl optionally substituted with halo, OH, $CH_3$, and $OCH_3$;
$R_2$ is H and $R_3$ is independently selected from: $(C_1-C_6)$alkyl, $(C_3-C_8)$cycloalkyl, and heterocyclyl each optionally substituted with one or more halo, OH, $N(R_b)_2$, or morpholinyl, or $R_2$ and $R_3$ can be taken together with the nitrogen to which they are attached to form a heterocyclyl, said heterocyclyl optionally substituted with one or more substituents selected from $R_a$;
$R_a$ is independently selected from $(C_1-C_4)$alkyl, $(C_3-C_6)$cycloalkyl, $CF_3$, $CHF_2$, OH, halo and $NH_2$, said alkyl optionally substituted with $(C_3-C_6)$cycloalkyl and $CF_3$; and
$R_b$ is independently selected from H and $(C_1-C_4)$alkyl;
or a pharmaceutically acceptable salt thereof.

Another embodiment of the instant invention is illustrated by the Formula I:
wherein:
Ring A is pyrazolyl, pyridinyl, thiophenyl, furanyl or phenyl;
n is 0, 1 or 2;
$R_1$ is independently selected from: $(C_1$-$C_4)$alkyl, cyclopropyl, oxadiazolyl, pyridinyl, oxazolyl, triazolyl, pyriminidyl, $CF_3$, $CHF_2$, CN and halo, said alkyl, oxadiazolyl, pyridinyl, oxazolyl, triazolyl and pyriminidyl are optionally substituted with halo, OH, $CH_3$, and $OCH_3$;
$R_2$ is H and $R_3$ is independently selected from: $(C_1$-$C_4)$ alkyl, cyclohexyl, cycloheptyl, piperidinyl and azepanyl each optionally substituted with one or more F, OH, $N(R_b)_2$, or morpholinyl, or $R_2$ and $R_3$ can be taken together with the nitrogen to which they are attached to form a heterocyclyl selected from piperazinyl, diazepanyl, diazabicyclooctyl, diazabicycloheptyl, diazaspirononyl, hexahydropyrrolopyrazinyl, piperidinyl, diazabicyclononyl, oxadiazabicyclodecyl and diazatricyclodecyl, said heterocyclyl optionally substituted with one or more substituents selected from $R_a$;
$R_a$ is independently selected from $(C_1$-$C_4)$alkyl, cyclopropyl, $CF_3$, $CHF_2$, OH, F and $NH_2$, said alkyl optionally substituted with cyclopropyl and $CF_3$; and
$R_b$ is independently selected from H and methyl;
or a pharmaceutically acceptable salt thereof.
A compound selected from:
2-{[(1R,2S)-2-aminocyclohexyl]amino}-N-[1-methyl-3-(trifluoromethyl)-1H-pyrazol-4-yl]thieno[2,3-b]pyrazine-7-carboxamide;
N-[1-methyl-3-(trifluoromethyl)-1H-pyrazol-4-yl]-2-piperazin-1-ylthieno[2,3-b]pyrazine-7-carboxamide;
2-{[(1R,2S)-2-hydroxycyclohexyl]amino}-N-[1-methyl-3-(trifluoromethyl)-1H-pyrazol-4-yl]thieno[2,3-b]pyrazine-7-carboxamide;
N-[1-methyl-3-(trifluoromethyl)-1H-pyrazol-4-yl]-2-[(3R)-piperidin-3-ylamino]thieno[2,3-b]pyrazine-7-carboxamide;
2-{[(1R,2R)-2-amino-3,3-difluorocyclohexyl]amino}-N-[1-methyl-3-(trifluoromethyl)-1H-pyrazol-4-yl]thieno[2,3-b]pyrazine-7-carboxamide;
2-(1,4-diazepan-1-yl)-N-[1-methyl-3-(trifluoromethyl)-1H-pyrazol-4-yl]thieno[2,3-b]pyrazine-7-carboxamide;
2-(2,5-diazabicyclo[2.2.2]oct-2-yl)-N-[1-methyl-3-(trifluoromethyl)-1H-pyrazol-4-yl]thieno[2,3-b]pyrazine-7-carboxamide;
2-(5,8-diazaspiro[2.6]non-5-yl)-N-[1-methyl-3-(trifluoromethyl)-1H-pyrazol-4-yl]thieno[2,3-b]pyrazine-7-carboxamide;
2-[(3R)-3-aminopiperidin-1-yl]-N-[1-methyl-3-(trifluoromethyl)-1H-pyrazol-4-yl]thieno[2,3-b]pyrazine-7-carboxamide;
N-[3-(difluoromethyl)-1-methyl-1H-pyrazol-4-yl]-2-{[(1R,2S)-2-hydroxycyclohexyl]amino}thieno[2,3-b]pyrazine-7-carboxamide;
2-(2,5-diazabicyclo[2.2.2]oct-2-yl)-N-[3-(difluoromethyl)-1-methyl-1H-pyrazol-4-yl]thieno[2,3-b]pyrazine-7-carboxamide;
N-[3-(difluoromethyl)-1-methyl-1H-pyrazol-4-yl]-2-piperazin-1-ylthieno[2,3-b]pyrazine-7-carboxamide;
2-(5,8-diazaspiro[2.6]non-5-yl)-N-[3-(difluoromethyl)-1-methyl-1H-pyrazol-4-yl]thieno[2,3-b]pyrazine-7-carboxamide;
2-(1,4-diazepan-1-yl)-N-[3-(difluoromethyl)-1-methyl-1H-pyrazol-4-yl]thieno[2,3-b]pyrazine-7-carboxamide;
2-(azepan-3-ylamino)-N-[1-methyl-3-(trifluoromethyl)-1H-pyrazol-4-yl]thieno[2,3-b]pyrazine-7-carboxamide;
N-(3-chloro-1-methyl-1H-pyrazol-4-yl)-2-[(1S,4S)-2,5-diazabicyclo[2.2.2]oct-2-yl]thieno[2,3-b]pyrazine-7-carboxamide;
N-(3-chloro-1-methyl-1H-pyrazol-4-yl)-2-[(1R,4R)-2,5-diazabicyclo[2.2.2]oct-2-yl]thieno[2,3-b]pyrazine-7-carboxamide;
N-(3-chloro-1-methyl-1H-pyrazol-4-yl)-2-(1,4-diazepan-1-yl)thieno[2,3-b]pyrazine-7-carboxamide;
N-(3-bromo-1-methyl-1H-pyrazol-4-yl)-2-[(1S,4S)-2,5-diazabicyclo[2.2.2]oct-2-yl]thieno[2,3-b]pyrazine-7-carboxamide;
N-(3-bromo-1-methyl-1H-pyrazol-4-yl)-2-[(1R,4R)-2,5-diazabicyclo[2.2.2]oct-2-yl]thieno[2,3-b]pyrazine-7-carboxamide;
N-(3-bromo-1-methyl-1H-pyrazol-4-yl)-2-(1,4-diazepan-1-yl)thieno[2,3-b]pyrazine-7-carboxamide;
2-[(1S,4S)-2,5-diazabicyclo[2.2.2]oct-2-yl]-N-[3-(difluoromethyl)-1-methyl-1H-pyrazol-4-yl]thieno[2,3-b]pyrazine-7-carboxamide;
2-[(1R,4R)-2,5-diazabicyclo[2.2.2]oct-2-yl]-N-[3-(difluoromethyl)-1-methyl-1H-pyrazol-4-yl]thieno[2,3-b]pyrazine-7-carboxamide;
2-[(3R)-3-aminopiperidin-1-yl]-N-[3-(difluoromethyl)-1-methyl-1H-pyrazol-4-yl]thieno[2,3-b]pyrazine-7-carboxamide;
2-{[(1R,2S)-2-aminocyclohexyl]amino}-N-[3-(difluoromethyl)-1-methyl-1H-pyrazol-4-yl]thieno[2,3-b]pyrazine-7-carboxamide;
N-(3-cyano-1-methyl-1H-pyrazol-4-yl)-2-[(1S,4S)-2,5-diazabicyclo[2.2.2]oct-2-yl]thieno[2,3-b]pyrazine-7-carboxamide;
N-(3-cyano-1-methyl-1H-pyrazol-4-yl)-2-[(1R,4R)-2,5-diazabicyclo[2.2.2]oct-2-yl]thieno[2,3-b]pyrazine-7-carboxamide;
N-(3-cyano-1-methyl-1H-pyrazol-4-yl)-2-(1,4-diazepan-1-yl)thieno[2,3-b]pyrazine-7-carboxamide;
2-{[(1R,2R)-2-amino-3,3-difluorocyclohexyl]amino}-N-(3-bromo-1-methyl-1H-pyrazol-4-yl)thieno[2,3-b]pyrazine-7-carboxamide;
2-{[(1R,2S)-2-aminocyclohexyl]amino}-N-(3-bromo-1-methyl-1H-pyrazol-4-yl)thieno[2,3-b]pyrazine-7-carboxamide;
2-[(3S)-azepan-3-ylamino]-N-[1-methyl-3-(trifluoromethyl)-1H-pyrazol-4-yl]thieno[2,3-b]pyrazine-7-carboxamide;
N-[3-(difluoromethyl)-1-methyl-1H-pyrazol-4-yl]-2-[(3R)-piperidin-3-ylamino]thieno[2,3-b]pyrazine-7-carboxamide;
2-[(3R)-azepan-3-ylamino]-N-[3-(difluoromethyl)-1-methyl-1H-pyrazol-4-yl]thieno[2,3-b]pyrazine-7-carboxamide;
2-[(3S)-azepan-3-ylamino]-N-[3-(difluoromethyl)-1-methyl-1H-pyrazol-4-yl]thieno[2,3-b]pyrazine-7-carboxamide;
2-{[(1R,2S)-2-aminocyclohexyl]amino}-N-(3-chloro-1-methyl-1H-pyrazol-4-yl)thieno[2,3-b]pyrazine-7-carboxamide;
2-{[(1R,2R)-2-amino-3,3-difluorocyclohexyl]amino}-N-(3-cyano-1-methyl-1H-pyrazol-4-yl)thieno[2,3-b]pyrazine-7-carboxamide;
2-{[(1R,2S)-2-aminocyclohexyl]amino}-N-(3-cyano-1-methyl-1H-pyrazol-4-yl)thieno[2,3-b]pyrazine-7-carboxamide;
2-[(3R)-azepan-3-ylamino]-N-[1-methyl-3-(trifluoromethyl)-1H-pyrazol-4-yl]thieno[2,3-b]pyrazine-7-carboxamide;

2-{[(1R,2R)-2-amino-3,3-difluorocyclohexyl]amino}-N-[3-(difluoromethyl)-1-methyl-1H-pyrazol-4-yl]thieno[2,3-b]pyrazine-7-carboxamide;

2-(3,8-diazabicyclo[3.2.1]oct-3-yl)-N-[3-(difluoromethyl)-1-methyl-1H-pyrazol-4-yl]thieno[2,3-b]pyrazine-7-carboxamide;

2-(3,8-diazabicyclo[3.2.1]oct-3-yl)-N-[1-methyl-3-(trifluoromethyl)-1H-pyrazol-4-yl]thieno[2,3-b]pyrazine-7-carboxamide;

2-{[(1R,2S)-2-aminocyclohexyl]amino}-N-[1-methyl-5-(trifluoromethyl)-1H-pyrazol-4-yl]thieno[2,3-b]pyrazine-7-carboxamide;

2-{[(1R,2R)-2-amino-3,3-difluorocyclohexyl]amino}-N-(3-chloro-1-methyl-1H-pyrazol-4-yl)thieno[2,3-b]pyrazine-7-carboxamide;

2-(3,8-diazabicyclo[3.2.1]oct-8-yl)-N-[3-(difluoromethyl)-1-methyl-1H-pyrazol-4-yl]thieno[2,3-b]pyrazine-7-carboxamide;

2-(3,8-diazabicyclo[3.2.1]oct-8-yl)-N-[1-methyl-3-(trifluoromethyl)-1H-pyrazol-4-yl]thieno[2,3-b]pyrazine-7-carboxamide;

N-(4-bromothiophen-3-yl)-2-[(1S,4S)-2,5-diazabicyclo[2.2.2]oct-2-yl]thieno[2,3-b]pyrazine-7-carboxamide;

2-(1,4-diazepan-1-yl)-N-[4-(difluoromethyl)thiophen-3-yl]thieno[2,3-b]pyrazine-7-carboxamide;

N-(4-bromothiophen-3-yl)-2-(1,4-diazepan-1-yl)thieno[2,3-b]pyrazine-7-carboxamide;

N-(4-bromothiophen-3-yl)-2-[(1S,4S)-2,5-diazabicyclo[2.2.2]oct-2-yl]thieno[2,3-b]pyrazine-7-carboxamide;

2-{[(1R,2S)-2-aminocyclohexyl]amino}-N-[4-(difluoromethyl)thiophen-3-yl]thieno[2,3-b]pyrazine-7-carboxamide;

N-(2-bromothiophen-3-yl)-2-(1,4-diazepan-1-yl)thieno[2,3-b]pyrazine-7-carboxamide;

N-(2-chlorothiophen-3-yl)-2-(1,4-diazepan-1-yl)thieno[2,3-b]pyrazine-7-carboxamide;

2-{[(1R,2S)-2-aminocyclohexyl]amino}-N-(4-bromothiophen-3-yl)thieno[2,3-b]pyrazine-7-carboxamide;

2-{[(1R,2S)-2-aminocyclohexyl]amino}-N-(2-bromothiophen-3-yl)thieno[2,3-b]pyrazine-7-carboxamide;

N-(4-cyanothiophen-3-yl)-2-(1,4-diazepan-1-yl)thieno[2,3-b]pyrazine-7-carboxamide;

2-{[(1R,2S)-2-aminocyclohexyl]amino}-N-(2-chlorothiophen-3-yl)thieno[2,3-b]pyrazine-7-carboxamide;

2-{[(1R,2S)-2-aminocyclohexyl]amino}-N-(4-cyanothiophen-3-yl)thieno[2,3-b]pyrazine-7-carboxamide;

2-[(1S,4S)-2,5-diazabicyclo[2.2.2]oct-2-yl]-N-[4-(difluoromethyl)thiophen-3-yl]thieno[2,3-b]pyrazine-7-carboxamide;

2-[(1R,4R)-2,5-diazabicyclo[2.2.2]oct-2-yl]-N-[4-(difluoromethyl)thiophen-3-yl]thieno[2,3-b]pyrazine-7-carboxamide;

2-{[(1R,2R)-2-amino-3,3-difluorocyclohexyl]amino}-N-(2-chlorothiophen-3-yl)thieno[2,3-b]pyrazine-7-carboxamide;

N-(2-chlorothiophen-3-yl)-2-[(1S,4S)-2,5-diazabicyclo[2.2.2]oct-2-yl]thieno[2,3-b]pyrazine-7-carboxamide;

N-(2-chlorothiophen-3-yl)-2-[(1R,4R)-2,5-diazabicyclo[2.2.2]oct-2-yl]thieno[2,3-b]pyrazine-7-carboxamide;

N-(2-bromothiophen-3-yl)-2-[(1S,4S)-2,5-diazabicyclo[2.2.2]oct-2-yl]thieno[2,3-b]pyrazine-7-carboxamide;

N-(2-bromothiophen-3-yl)-2-[(1R,4R)-2,5-diazabicyclo[2.2.2]oct-2-yl]thieno[2,3-b]pyrazine-7-carboxamide;

N-(4-cyanothiophen-3-yl)-2-[(1S,4S)-2,5-diazabicyclo[2.2.2]oct-2-yl]thieno[2,3-b]pyrazine-7-carboxamide;

N-(4-cyanothiophen-3-yl)-2-[(1R,4R)-2,5-diazabicyclo[2.2.2]oct-2-yl]thieno[2,3-b]pyrazine-7-carboxamide;

2-{[(1R,2R)-2-amino-3,3-difluorocyclohexyl]amino}-N-[4-(difluoromethyl)thiophen-3-yl]thieno[2,3-b]pyrazine-7-carboxamide;

2-{[(1R,2R)-2-amino-3,3-difluorocyclohexyl]amino}-N-(4-bromothiophen-3-yl)thieno[2,3-b]pyrazine-7-carboxamide;

N-(2-cyanothiophen-3-yl)-2-[(1S,4S)-2,5-diazabicyclo[2.2.2]oct-2-yl]thieno[2,3-b]pyrazine-7-carboxamide;

N-(2-cyanothiophen-3-yl)-2-[(1R,4R)-2,5-diazabicyclo[2.2.2]oct-2-yl]thieno[2,3-b]pyrazine-7-carboxamide;

2-{[(1R,2R)-2-amino-3,3-difluorocyclohexyl]amino}-N-(2-bromothiophen-3-yl)thieno[2,3-b]pyrazine-7-carboxamide;

N-(2-cyanothiophen-3-yl)-2-(1,4-diazepan-1-yl)thieno[2,3-b]pyrazine-7-carboxamide;

2-(1,4-diazepan-1-yl)-N-[2-(trifluoromethyl)thiophen-3-yl]thieno[2,3-b]pyrazine-7-carboxamide;

2-[(1S,4S)-2,5-diazabicyclo[2.2.2]oct-2-yl]-N-[2-(trifluoromethyl)thiophen-3-yl]thieno[2,3-b]pyrazine-7-carboxamide;

2-[(1R,4R)-2,5-diazabicyclo[2.2.2]oct-2-yl]-N-[2-(trifluoromethyl)thiophen-3-yl]thieno[2,3-b]pyrazine-7-carboxamide;

2-{[(1R,2S)-2-aminocyclohexyl]amino}-N-[2-(trifluoromethyl)thiophen-3-yl]thieno[2,3-b]pyrazine-7-carboxamide;

2-{[(1R,2S)-2-aminocyclohexyl]amino}-N-(2-cyanothiophen-3-yl)thieno[2,3-b]pyrazine-7-carboxamide;

2-{[(1R,2R)-2-amino-3,3-difluorocyclohexyl]amino}-N-(2-cyanothiophen-3-yl)thieno[2,3-b]pyrazine-7-carboxamide;

2-{[(1R,2R)-2-amino-3,3-difluorocyclohexyl]amino}-N-(4-cyanothiophen-3-yl)thieno[2,3-b]pyrazine-7-carboxamide;

N-(2-cyanophenyl)-2-(1,4-diazepan-1-yl)thieno[2,3-b]pyrazine-7-carboxamide;

2-{[(1R,2S)-2-aminocyclohexyl]amino}-N-[2-(trifluoromethyl)phenyl]thieno[2,3-b]pyrazine-7-carboxamide;

N-(2-bromophenyl)-2-(1,4-diazepan-1-yl)thieno[2,3-b]pyrazine-7-carboxamide;

N-(2-cyanophenyl)-2-(5,8-diazaspiro[2.6]non-5-yl)thieno[2,3-b]pyrazine-7-carboxamide;

2-[(3R)-3-aminopiperidin-1-yl]-N-(2-cyanophenyl)thieno[2,3-b]pyrazine-7-carboxamide;

N-(2-cyanophenyl)-2-[(3R)-piperidin-3-ylamino]thieno[2,3-b]pyrazine-7-carboxamide;

N-(2-cyanophenyl)-2-piperazin-1-ylthieno[2,3-b]pyrazine-7-carboxamide;

2-{[(1R,2S)-2-aminocyclohexyl]amino}-N-(2-bromophenyl)thieno[2,3-b]pyrazine-7-carboxamide;

N-(2-bromophenyl)-2-[(1S,4S)-2,5-diazabicyclo[2.2.2]oct-2-yl]thieno[2,3-b]pyrazine-7-carboxamide;

N-(2-bromophenyl)-2-[(1R,4R)-2,5-diazabicyclo[2.2.2]oct-2-yl]thieno[2,3-b]pyrazine-7-carboxamide;

2-(1,4-diazepan-1-yl)-N-[2-(trifluoromethyl)phenyl]thieno[2,3-b]pyrazine-7-carboxamide;

N-(2-chlorophenyl)-2-(1,4-diazepan-1-yl)thieno[2,3-b]pyrazine-7-carboxamide;

2-{[(1R,2S)-2-aminocyclohexyl]amino}-N-(2-chlorophenyl)thieno[2,3-b]pyrazine-7-carboxamide;

2-[(3S)-azepan-3-ylamino]-N-(2-cyanophenyl)thieno[2,3-b]pyrazine-7-carboxamide;

2-[(3R)-azepan-3-ylamino]-N-(2-cyanophenyl)thieno[2,3-b]pyrazine-7-carboxamide;

2-{[(1R,2S)-2-aminocyclohexyl]amino}-N-(2-cyanophenyl)thieno[2,3-b]pyrazine-7-carboxamide;

2-{[(1R,2R)-2-amino-3,3-difluorocyclohexyl]amino}-N-(2-bromophenyl)thieno[2,3-b]pyrazine-7-carboxamide;

N-(2-cyanophenyl)-2-[(1S,4S)-2,5-diazabicyclo[2.2.2]oct-2-yl]thieno[2,3-b]pyrazine-7-carboxamide;

N-(2-cyanophenyl)-2-[(1R,4R)-2,5-diazabicyclo[2.2.2]oct-2-yl]thieno[2,3-b]pyrazine-7-carboxamide;

N-(2-chlorophenyl)-2-[(1S,4S)-2,5-diazabicyclo[2.2.2]oct-2-yl]thieno[2,3-b]pyrazine-7-carboxamide;

N-(2-chlorophenyl)-2-[(1R,4R)-2,5-diazabicyclo[2.2.2]oct-2-yl]thieno[2,3-b]pyrazine-7-carboxamide;

2-{[(1R,2R)-2-amino-3,3-difluorocyclohexyl]amino}-N-(2-chlorophenyl)thieno[2,3-b]pyrazine-7-carboxamide;

2-{[(1R,2S)-2-aminocyclohexyl]amino}-N-[2-(difluoromethyl)phenyl]thieno[2,3-b]pyrazine-7-carboxamide;

2-(1,4-diazepan-1-yl)-N-[2-(difluoromethyl)phenyl]thieno[2,3-b]pyrazine-7-carboxamide;

2-[(1R,4R)-2,5-diazabicyclo[2.2.2]oct-2-yl]-N-[2-(difluoromethyl)phenyl]thieno[2,3-b]pyrazine-7-carboxamide;

2-{[(1R,2R)-2-amino-3,3-difluorocyclohexyl]amino}-N-(2-cyanophenyl)thieno[2,3-b]pyrazine-7-carboxamide;

2-{[(1R,2R)-2-amino-3,3-difluorocyclohexyl]amino}-N-[2-(difluoromethyl)phenyl]thieno[2,3-b]pyrazine-7-carboxamide;

N-(4-chlorothiophen-3-yl)-2-(1,4-diazepan-1-yl)thieno[2,3-b]pyrazine-7-carboxamide;

N-(4-chlorothiophen-3-yl)-2-[(1S,4S)-2,5-diazabicyclo[2.2.2]oct-2-yl]thieno[2,3-b]pyrazine-7-carboxamide;

N-(4-chlorothiophen-3-yl)-2-[(1R,4R)-2,5-diazabicyclo[2.2.2]oct-2-yl]thieno[2,3-b]pyrazine-7-carboxamide;

2-{[(1R,2S)-2-aminocyclohexyl]amino}-N-(4-chlorothiophen-3-yl)thieno[2,3-b]pyrazine-7-carboxamide; and 2-{[(1R,2R)-2-amino-3,3-difluorocyclohexyl]amino}-N-(4-chlorothiophen-3-yl)thieno[2,3-b]pyrazine-7-carboxamide;

or a pharmaceutically acceptable salt thereof.

When any variable (e.g. $R_a$, etc.) occurs more than one time in any constituent, its definition on each occurrence is independent at every other occurrence. Also, combinations of substituents and variables are permissible only if such combinations result in stable compounds.

Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. In some instances, two substituents are attached to the same carbon and come together to form a carbocyclic or heterocyclic ring (a spirocyclic ring system).

As used herein, "alkyl" is intended to include both branched and straight-chain saturated aliphatic hydrocarbon groups having the specified number of carbon atoms. For example, $C_1$-$C_6$, as in "($C_1$-$C_6$)alkyl" is defined to include groups having 1, 2, 3, 4, 5 or 6 carbons in a linear or branched arrangement. For example, "($C_1$-$C_6$)alkyl" specifically includes methyl, ethyl, n-propyl, i-propyl, n-butyl, t-butyl, i-butyl, pentyl, hexyl, and so on. For example, $C_1$-$C_4$, as in "($C_1$-$C_4$)alkyl" is defined to include groups having 1, 2, 3 or 4 carbons in a linear or branched arrangement. For example, "($C_1$-$C_4$)alkyl" specifically includes methyl, ethyl, n-propyl, i-propyl, n-butyl, t-butyl and i-butyl.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes spiro, bicyclic and tricyclic groups. "Heterocyclyl" therefore includes heteroaryls, as well as dihydro and tetrathydro analogs thereof. Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (I).

The compounds of this invention include the salts, solvates, hydrates or prodrugs of the compounds. The use of the terms "salt", "solvate", "hydrate", "prodrug" and the like, is intended to equally apply to the salt, solvate, hydrate and prodrug of enantiomers, stereoisomers, rotamers, tautomers, positional isomers, or racemates of the inventive compounds.

Salts

The IRAK4 inhibitor compounds of the present invention, which can be in the form of a free base, may be isolated from the reaction mixture in the form of a pharmaceutically acceptable salt.

The compounds of Formula I can form salts which are also within the scope of this invention. Reference to a compound of Formula I herein is understood to include reference to pharmaceutically acceptable salts thereof, unless otherwise indicated. The term "pharmaceutically acceptable salt(s)" or "salt", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Crystals

The IRAK4 inhibitor compounds of the present invention may exist as amorphous forms or crystalline forms.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

Solvates

The compounds having Formula I or the pharmaceutically acceptable salts may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

One or more compounds of the invention having Formula I or the pharmaceutically acceptable salts or solvates thereof may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

Optical Isomers

The compounds of Formula I may contain asymmetric or chiral centers, and, therefore, exist in different stereoisomeric forms. It is intended that all stereoisomeric forms of the compounds of Formula I, as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention. Such stereoisomeric forms also include enantiomers and diastereoisomers, etc.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in *Chirality in Industry* (edited by A. N. Collins, G. N. Sheldrake and J. Crosby, 1992; John Wiley). Likewise methods for synthesis of geometrical isomers are also well known in the art.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Prodrugs

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of Formula I or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Isotopes

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula I (e.g. those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labeled reagent for a non-isotopically labeled reagent.

Utility

According to another embodiment, the present invention provides a method of treating or reducing the severity of a disease in a patient by using a compound of Formulas I as described above, wherein said disease is selected from IRAK4 mediated pathologies, such as rheumatoid arthritis, multiple sclerosis, sepsis, osteoarthritis, inflammatory bowel disease, Parkinson's disease, cardiac contractile dysfunction, type I diabetes, type II diabetes or familial cold autoinflammatory syndrome, allergic disease, cancer, lupus, psoriasis, asthma or graft rejection.

The compounds of the invention find use in a variety of applications. As will be appreciated by those skilled in the art, the kinase activity of IRAK4 may be modulated in a variety of ways; that is, one can affect the phosphorylation/activation of IRAK4 either by modulating the initial phosphorylation of the protein or by modulating the autophosphorylation of the other active sites of the protein. Alternatively, the kinase activity of IRAK4 may be modulated by affecting the binding of a substrate of IRAK4 phosphorylation.

The compounds of the invention are used to treat or prevent inflammation related diseases. Disease states which can be treated by the methods and compositions provided herein include, but are not limited to, cancer, autoimmune disease, viral disease, fungal disease, neurological/neurodegenerative disorders, arthritis, inflammation, anti-proliferative (e.g. ocular retinopathy), neuronal, alopecia, cardiovascular disease, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or *arachis* oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, age, weight, sex; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. For example, compounds of the instant invention can be administered in a total daily dose of up to 10,000 mg. Compounds of the instant invention can be administered once daily (QD), or divided into multiple daily doses such as twice daily (BID), and three times daily (TID). Compounds of the instant invention can be administered at a total daily dosage of up to 10,000 mg, e.g., 2,000 mg, 3,000 mg, 4,000 mg, 6,000 mg, 8,000 mg or 10,000 mg, which can be administered in one daily dose or can be divided into multiple daily doses as described above.

For example, compounds of the instant invention can be administered in a total daily dose of up to 1,000 mg. Compounds of the instant invention can be administered once daily (QD), or divided into multiple daily doses such as twice daily (BID), and three times daily (TID). Compounds of the instant invention can be administered at a total daily dosage of up to 1,000 mg, e.g., 200 mg, 300 mg, 400 mg, 600 mg, 800 mg or 1,000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention.

The instant compounds are also useful in combination with other therapeutic agents. Combinations of the presently disclosed compounds with therapeutic agents are within the scope of the invention. A person of ordinary skill in the art would be able to discern which combinations of agents would be useful based on the particular characteristics of the drugs and the pathologies involved. The instant compounds are also useful in combination with known therapeutic agents.

The instant compounds are useful in combination with a known anti-inflammatory agent. In one embodiment, the anti-inflammatory agent is a nonsteroidal anti-inflammatory drug (NSAID). In one embodiment, the NSAID is selected from the group consisting of salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, a pharmaceutically acceptable salt thereof, and a mixture thereof.

In another embodiment, the NSAID is a selective COX-2 inhibitor. For purposes of this specification NSAID's which are selective inhibitors of COX-2 are defined as those which possess a specificity for inhibiting COX-2 over COX-1 of at least 100 fold as measured by the ratio of IC50 for COX-2 over IC50 for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Compounds that have been described as specific inhibitors of COX-2 and are therefore useful in the present invention include, but are not limited to: parecoxib, CELEBREX® and BEXTRA® or a pharmaceutically acceptable salt thereof.

Those skilled in the art will realize that the term "cancer" to be the name for diseases in which the body's cells become abnormal and divide without control.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, neuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compositions and methods of the invention include acute myeloid leukemia (AML), liposarcoma, colorectal cancer, gastric cancer and melanoma.

In a further embodiment, cancers that may be treated by the compositions and methods of the invention include hematological malignancies, for example acute myeloid leukemia.

In a further embodiment, cancers that may be treated by the compositions and methods of the invention include acute lymphoblastic leukemia (ALL), lymphoma, lung, breast and glioblastoma.

The compounds of the invention are also useful in preparing a medicament that may be useful in treating cancer. In one embodiment, the compounds of the invention are for the potential treatment of cancer.

The compounds of the invention may be useful to the treatment of a variety of cancers, including, but not limited to: carcinoma, including, but not limited to, of the bladder, breast, colon, rectum, endometrium, kidney, liver, lung, head and neck, esophagus, gall bladder, cervix, pancreas, prostrate, larynx, ovaries, stomach, uterus, sarcoma and thyroid cancer; hematopoietic tumors of the lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoetic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma, and schwannomas; and other tumors, including melanoma, skin (non-melanoma) cancer, mesothelioma (cells), seminoma, teratocarcinoma, osteosarcoma, xenoderoma pigmentosum, keratoctanthoma, thyroid follicular cancer and Kaposi's sarcoma.

The compounds of the invention may be useful for the treatment of activated B-cell-like diffuse large B-cell lymphoma (ABC-DLBCL), chronic lymphocytic leukemia (CLL) and Waldenström's Macroglobulinemia.

The instant compounds are useful in combination with a known anti-cancer agent. Combinations of the presently disclosed compounds with anti-cancer agents are within the scope of the invention. Examples of such anti-cancer agents can be found in Cancer Principles and Practice of Oncology by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints.

In one embodiment, the anti-cancer agent is selected from the group consisting of abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leupolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®); a pharmaceutically acceptable salt thereof, and a mixture thereof.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

Further included within the scope of the invention is a method for treating an inflammatory disease which comprises administering to a mammal in need thereof a therapeutically effective amount of a compound of the instant invention.

Further included within the scope of the invention is a method for treating an inflammatory disease which comprises administering to a mammal in need thereof a therapeutically effective amount of a compound of the instant invention wherein the inflammatory disease is selected from rheumatoid arthritis, inflammatory bowel disease and cancer.

The compounds of the instant invention are useful for the treatment and/or reducing the severity of rheumatoid arthritis.

The compounds of the instant invention are useful for the treatment and/or reducing the severity of inflammatory bowel disease.

The compounds of the instant invention are useful for the treatment and/or reducing the severity of lupus.

The compounds of the instant invention are useful for the treatment and/or reducing the severity of cancer.

The compounds of the instant invention are useful for the treatment of rheumatoid arthritis.

The compounds of the instant invention are useful for the treatment of inflammatory bowel disease.

The compounds of the instant invention are useful for the treatment of lupus.

The compounds of the instant invention are useful for the treatment of cancer.

Further included within the scope of the invention is a method of treating an inflammatory disease which comprises administering a therapeutically effective amount of a compound of the instant invention in combination with a second therapeutic agent.

Further included within the scope of the invention is a method of treating an inflammatory disease which comprises administering a therapeutically effective amount of a compound of the instant invention in combination with a second therapeutic agent, wherein the second therapeutic agent is selected from an anti-cancer agent and an anti-inflammatory agent.

Abbreviations used in the description of the chemistry and in the Examples that follow are: Ac (Acetyl); ACN or MeCN (acetonitrile); AcOH or HOAc (acetic acid); Boc or BOC (tert-butoxycarbonyl); Bu (butyl); Bz (benzoyl); calc'd (calculated); Cbz (benyzloxycarbonyl); CDCl$_3$ (chloroform-d); CHCl$_3$ (Chloroform); DAST ((diethylamino)sulfur trifluoride); DCM (dichloromethane); DIEA or Hünig's base (N,N-diisopropylethylamine); DMAP (4-dimethylaminopyridine); DMSO (Dimethylsulfoxide); DMF (dimethylformamide); dppf (1,1'-bis(diphenylphosphino)ferrocene); Et (ethyl); EtOH (ethanol); EtOAc (ethyl acetate); g (grams); GST (glutathione S-transferase); h (hour); HATU (N,N,N',N'-tetramethyl-O-(7-azabenzotriazol-1-yl)uronium hexafluorophosphate); HCl (hydrochloric acid); HOBt (1-hydroxybenzotriazole); HPLC (high-performance liquid chromatography); IPA or iPrOH (isopropanol); iPr (isopropyl); LC (liquid chromatography); LCMS (liquid chromatography mass spectrometry); M (molar); mCPBA (m-choroperoxybenzoic acid); Me (methyl); MeOH (methanol); mg (milligrams); min (minute); μL (microliters); mL (milliliters); mmol (millimoles); MS (mass spectrometry); MTBE (methyl tert-butyl ether); NMR (nuclear magnetic resonance spectroscopy); OAc (Acetate); Pd(dppf)Cl$_2$ (1,1'-bis(diphenylphosphino)ferrocene]dichloropalladium(II)); Ph (phenyl); POCl$_3$ (phosphorous oxychloride); Pr (propyl); rac (racemic mixture); RT or rt (room temperature (ambient, about 25° C.)); sat (saturated); SFC (supercritical fluid chromatography); tBu (tert-butyl); TEA (triethylamine (Et$_3$N)); TFA (trifluoroacetic acid); THF (tetrahydrofuran); TLC (thin layer chromatography); and Xantphos (4,5-bis (diphenylphosphino)-9,9-dimethylxanthene).

General Synopsis of Reaction Schemes

The following General Reaction Schemes, Schemes 1 to 2, provide useful details for preparing the instant compounds. The requisite intermediates are in some cases commercially available or can be prepared according to literature procedures. The illustrative General Reaction Schemes below are not limited by the compounds listed or by any particular substituents employed for illustrative purposes. Substituent labelings (i.e. R groups) as shown in the Reaction Schemes do not necessarily correlate to that used in the claims and often, for clarity, a single substituent is shown attached to the compound where multiple substituents are allowed under the definitions of Formula I hereinabove.

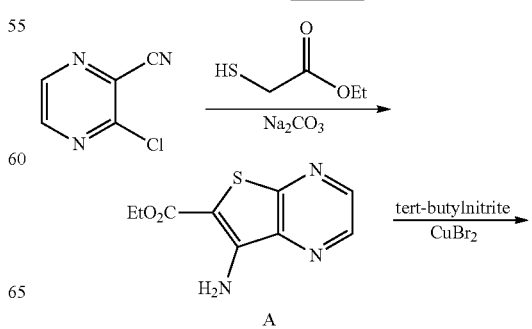

Scheme 1

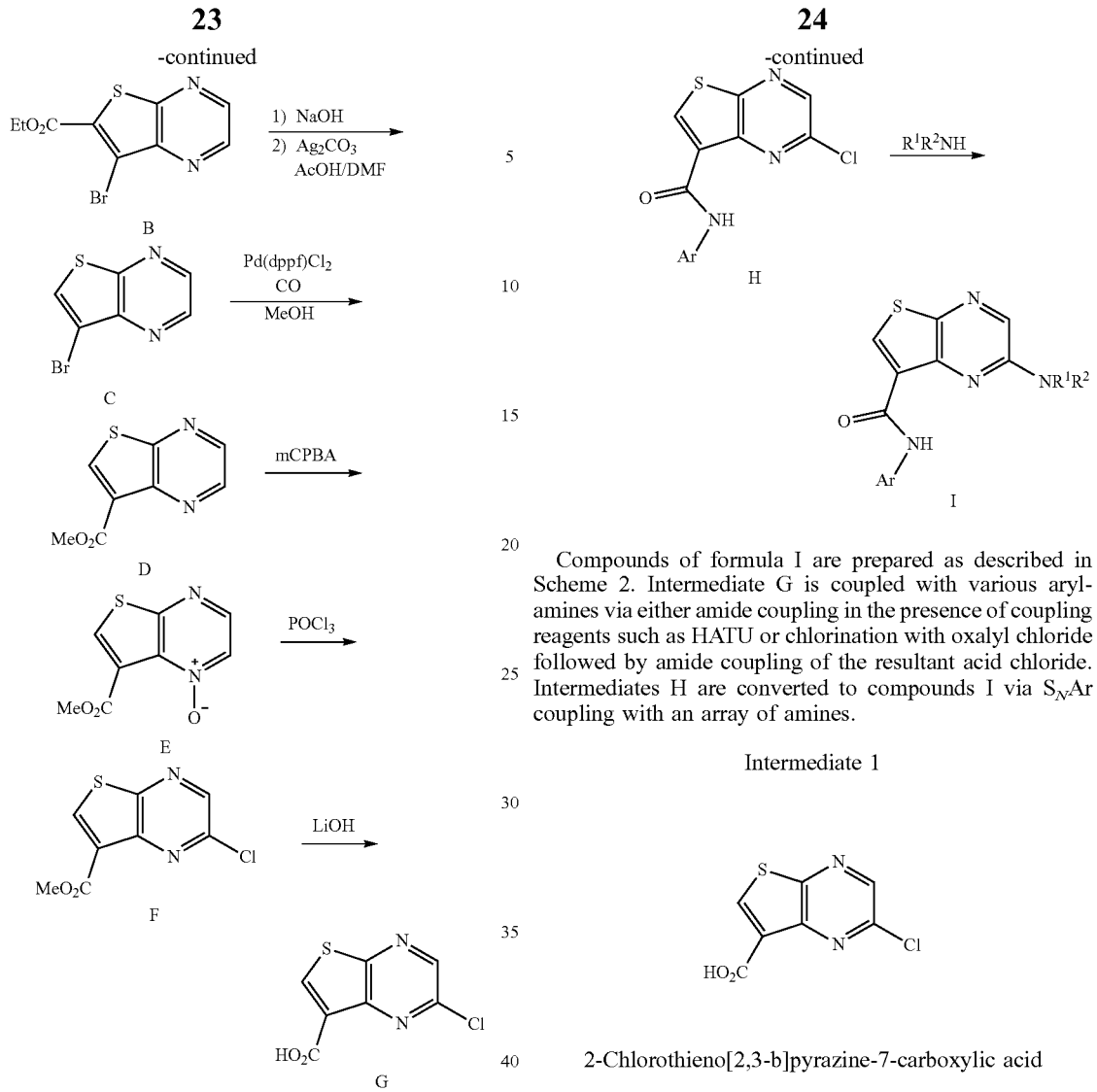

2-Chlorothieno[2,3-b]pyrazine-7-carboxylic acid (G) is prepared as described in Scheme 1. 3-Chloropyrazine-2-carbonitrile is condensed with ethyl 2-sulfanylacetate in the presence of sodium carbonate at an elevated temperature to afford 7-aminothieno[2,3-b]pyrazine-6-carboxylate (A). Intermediate A is converted to intermediate C via sequential Sandmeyer conditions (CuBr$_2$, tert-butylnitrite), saponification, and decarboxylation. Intermediate C is then converted to intermediate D via palladium-mediated carbonylation in methanol. Intermediate D is converted to intermediate G via sequential mCPBA oxidation, chlorination and saponification.

Scheme 2

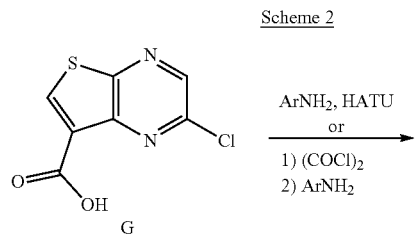

Compounds of formula I are prepared as described in Scheme 2. Intermediate G is coupled with various arylamines via either amide coupling in the presence of coupling reagents such as HATU or chlorination with oxalyl chloride followed by amide coupling of the resultant acid chloride. Intermediates H are converted to compounds I via S$_N$Ar coupling with an array of amines.

Intermediate 1

2-Chlorothieno[2,3-b]pyrazine-7-carboxylic acid

Step 1: Into a 2000 mL 4 necked round bottom flask purged and maintained with an inert atmosphere of nitrogen were placed a solution of 3-chloropyrazine-2-carbonitrile (100 g, 716 mmol) in ethanol (660 mL), ethyl 2-sulfanylacetate (112 g, 932 mmol) and sodium carbonate (99 g, 930 mmol). The resulting solution was stirred for 4.5 h at 100° C. in an oil bath. The reaction mixture was cooled to room temperature and poured into 7.5 L of water. The solid was collected by filtration. The solid was dissolved in 1500 mL of ethyl ether and filtered. The filtrate was concentrated under reduced pressure. This resulted in ethyl 7-aminothieno [2,3-b]pyrazine-6-carboxylate as a solid.

Step 2: Into a 2000 mL 4 necked round bottom flask purged and maintained with an inert atmosphere of nitrogen were placed a solution of t-butylnitrite (42.4 g, 411 mmol) in acetonitrile (700 mL) and CuBr$_2$ (79.2 g, 355 mmol). This was followed by the addition of ethyl 7-aminothieno[2,3-b] pyrazine-6-carboxylate (72 g, 323 mmol) in several batches at 0° C. over 2 h. The resulting solution was stirred for 1 h at room temperature. The reaction was treated with 400 mL of aqueous ammonia. The resulting solution was extracted with 2×1000 mL of ethyl acetate and the combined organic layers were dried over anhydrous sodium sulfate. The mixture was filtered, concentrated under reduced pressure and purified by flash chromatography to afford ethyl 7-bromothieno[2,3-b]pyrazine-6-carboxylate as a solid.

Step 3: Into a 1000 mL 4 necked round bottom flask purged and maintained with an inert atmosphere of nitrogen was placed a solution of ethyl 7-bromothieno[2,3-b]pyrazine-6-carboxylate (52 g, 180 mmol) in ethanol (150 mL). This was followed by the addition of sodium hydroxide (172 mL, 2 N) in portions at room temperature. The resulting solution was stirred for 5 min at room temperature. The pH value of the solution was adjusted to 3-4 with hydrogen chloride (2 N). The solids were collected by filtration and dried in an oven under reduced pressure. This resulted in 7-bromothieno[2,3-b]pyrazine-6-carboxylic acid as a solid.

Step 4: Into a 2000 mL 4 necked round bottom flask purged and maintained with an inert atmosphere of nitrogen were placed a solution of 7-bromothieno[2,3-b]pyrazine-6-carboxylic acid (100 g, 386 mmol) in N,N-dimethylformamide (1000 mL), Ag$_2$CO$_3$ (5.3 g, 19 mmol) and AcOH (1.1 g, 18 mmol). The resulting solution was stirred for 4 h at 120° C. in an oil bath. The reaction mixture was cooled to room temperature and extracted with 2×1000 mL of ether. The combined organics were dried over anhydrous sodium sulfate, filtered, concentrated, and purified by flash chromatography eluting with ethyl acetate/petroleum ether (1:30) to afford 7-bromothieno[2,3-b]pyrazine as a solid.

Step 5: Into a 1000 mL pressure tank reactor (15 atm) were placed a solution of 7-bromothieno[2,3-b]pyrazine (40 g, 190 mmol) in methanol (400 mL), Pd(dppf)Cl$_2$.CH$_2$Cl$_2$ (7.6 g) and triethylamine (94 g, 930 mmol). Into the mixture was introduced CO and the resulting solution was stirred overnight at 100° C. The reaction mixture was cooled to room temperature, concentrated under reduced pressure, and purified by flash chromatography eluting with ethyl acetate/petroleum ether (1:3) to afford methyl thieno[2,3-b]pyrazine-7-carboxylate as a solid.

Step 6: Into a 1000 mL 4 necked round bottom flask purged and maintained with an inert atmosphere of nitrogen were placed a solution of methyl thieno[2,3-b]pyrazine-7-carboxylate (20 g, 100 mmol) in dichloromethane (200 mL) and mCPBA (3.6 g). The resulting solution was stirred overnight at room temperature, concentrated under reduced pressure and purified by flash chromatography eluting with ethyl acetate/petroleum ether (1:3) to afford methyl thieno[2,3-b]pyrazine-7-carboxylate 1-oxide as a solid.

Step 7: Into a 1000 mL 4 necked round bottom flask purged and maintained with an inert atmosphere of nitrogen were placed a solution of methyl thieno[2,3-b]pyrazine-7-carboxylate 1-oxide (21.5 g, 102 mmol) in CH$_3$CN (220 mL), POCl$_3$ (47 g, 310 mmol) and N-dimethylaniline (18.6 g, 153 mmol). The resulting solution was stirred for 2 h at 40° C. in an oil bath, cooled to room temperature and concentrated under reduced pressure. The residue was treated with 400 mL of water/ice and the solid was collected by filtration and dried in an oven under reduced pressure. This resulted in methyl 2-chlorothieno[2,3-b]pyrazine-7-carboxylate as a solid.

Step 8: Into a 2000 mL 4 necked round bottom flask purged and maintained with an inert atmosphere of nitrogen were placed a solution of methyl 2-chlorothieno[2,3-b]pyrazine-7-carboxylate (20 g, 87 mmol) in tetrahydrofuran/H$_2$O (500/200 mL) and LiOH (3.8 g, 160 mmol). The resulting solution was stirred for 2 h at room temperature and washed with 2×500 mL of ether. The pH value of the aqueous layer was adjusted to 2-3 with hydrogen chloride (1.5 N). The solids were collected by filtration and dried in an oven under reduced pressure to afford 2-chlorothieno[2,3-b]pyrazine-7-carboxylic acid as a solid. $^1$H NMR (CDCl$_3$, 300 MHz): δ 13.44 (s, 1H), 9.14 (s, 1H), 3.87 (s, 1H). MS [M+H]+ 215.

Intermediate 2

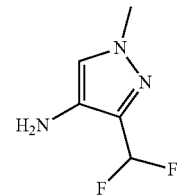

3-(Difluoromethyl)-1-methyl-1H-pyrazol-4-amine

Step 1: Into a 100 mL round bottom flask containing a solution of methyl 1-methyl-4-nitro-1H-pyrazole-3-carboxylate (1.5 g, 8 mmol) in dichloromethane (30 mL) was added diisobutylaluminum hydride (12 mL, 1 M in toluene, 12 mmol) at 0° C. and the reaction mixture was stirred at room temperature for 6 h. The reaction mixture was treated with hydrochloric acid (1.5 N, 1 mL) and extracted with ethyl acetate. The organic fraction was dried over anhydrous sodium sulfate, filtered and concentrated under reduced pressure. The residue was purified by flash chromatography eluting with methanol in dichloromethane (5-10%) to yield (1-methyl-4-nitro-1H-pyrazol-3-yl)methanol as a solid. $^1$H NMR (DMSO-d$_6$, 300 MHz): δ 8.77 (s, 1H), 5.19 (t, J=5.9 Hz, 1H), 4.63 (d, J=5.9 Hz, 2H), 3.85 (s, 3H).

Step 2: Into a 50 mL round bottom flask containing a solution of 2-iodoxybenzoic acid (2.8 g, 10 mmol) in dimethyl sulfoxide (3 mL) was added a solution of (1-methyl-4-nitro-1H-pyrazol-3-yl)methanol (800 mg, 5 mmol) in dimethyl sulfoxide (3 mL) and the reaction mixture was stirred at room temperature for 3 h. The reaction mixture was diluted with diethyl ether and washed with water and brine. The organic fraction was dried over anhydrous sodium sulfate, filtered and concentrated under reduced pressure. The residue was purified by flash chromatography eluting with methanol in dichloromethane (7-9%) to yield 1-methyl-4-nitro-1H-pyrazole-3-carbaldehyde as a solid. $^1$H NMR (CDCl$_3$, 400 MHz): δ 10.43 (s, 1H), 8.25 (s, 1H), 4.09 (s, 3H).

Step 3: Into a 25 mL round bottom flask containing a solution of 1-methyl-4-nitro-1H-pyrazole-3-carbaldehyde (300 mg, 1.9 mmol) in dichloromethane (5 mL) was added diethylaminosulfur trifluoride (0.76 mL, 5.8 mmol) at −20° C. and the reaction was stirred at room temperature for 16 h. The reaction mixture was concentrated under reduced pressure and the residue was purified by flash chromatography eluting with methanol in dichloromethane (3-5%) to yield 3-(difluoromethyl)-1-methyl-4-nitro-1H-pyrazole. $^1$H NMR (CDCl$_3$, 400 MHz): δ 8.19 (s, 1H), 7.13 (t, J=53.2 Hz, 1H), 4.03 (s, 3H).

Step 4: Into a 25 mL round bottom flask containing a solution of 3-(difluoromethyl)-1-methyl-4-nitro-1H-pyrazole (300 mg, 1.93 mmol) in methanol (3 mL) was added palladium on carbon (15 mg, 5% w/w) and the reaction was stirred at room temperature for 8 h under hydrogen bladder pressure. The reaction mixture was filtered through celite and washed with methanol and the filtrate was concentrated under reduced pressure. The residue was purified by flash chromatography eluting with methanol in dichloromethane (4-7%) to yield 3-(difluoromethyl)-1-methyl-1H-pyrazol-4- amine. ¹H NMR (CDCl₃, 400 MHz): δ 7.09 (s, 1H), 6.86 (t, J=54.1 Hz, 1H), 3.70 (s, 3H). MS calc'd [M+H]⁺ 148.1, found 148.2.

Intermediate 3

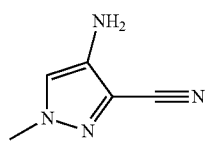

4-Amino-1-methyl-1H-pyrazole-3-carbonitrile

Step 1: Into a 250 mL round bottom flask containing a suspension of 4-nitro-1H-pyrazole-3-carboxylic acid (20.0 g, 127 mmol) in methanol (100 mL) was added concentrated sulfuric acid (4 mL) dropwise over 5 min at 0° C. and the resulting slurry was refluxed at 80° C. for 16 h. The solvent was removed under reduced pressure and the residual mass was dissolved in ethyl acetate (300 mL) and washed with saturated aqueous sodium bicarbonate solution (2×100 mL) and brine (100 mL) and dried over anhydrous sodium sulfate. The solution was filtered and concentrated under reduced pressure to give methyl 4-nitro-1H-pyrazole-3-carboxylate as a solid. The crude product was taken to the next step without further purification. MS calc'd [M−H]⁺170.0, found 170.0.

Step 2: Into a 1 L round bottom flask containing a suspension of sodium hydride (60% in paraffin oil, 4.7 g, 116 mmol) in tetrahydrofuran (400 mL) at 0° C. was added methyl 4-nitro-1H-pyrazole-3-carboxylate (16.5 g, 96 mmol) in tetrahydrofuran (50 mL) dropwise and the reaction mixture was stirred for 1 h. To the reaction mixture was added methyl iodide (9 mL, 145 mmol) and the mixture was stirred at room temperature for 3 h. The reaction mixture was cooled to 0° C. and treated with saturated aqueous ammonium chloride solution and extracted with ethyl acetate (4×200 mL). The combined organic fractions were washed with brine (100 mL), dried over anhydrous sodium sulfate, filtered and concentrated under reduced pressure. The residue was purified by flash chromatography eluting with ethyl acetate in petroleum ether (15-25%) to afford methyl 1-methyl-4-nitro-1H-pyrazole-3-carboxylate as a solid. ¹H NMR (CDCl₃, 400 MHz): δ 8.17 (s, 1H), 4.03 (s, 3H), 4.01 (s, 3H).

Step 3: Into a 250 mL sealed tube were added methyl 1-methyl-4-nitro-1H-pyrazole-3-carboxylate (2.5 g, 13.5 mmol) and methanol (60 mL) and the reaction mixture was cooled to −60° C. and ammonia gas was purged for 15 min and then heated at 80° C. for 4 h. The reaction mixture was cooled to −15° C. and the excess ammonia gas was carefully removed by bubbling nitrogen and concentrated under reduced pressure to afford 1-methyl-4-nitro-1H-pyrazole-3-carboxamide as a solid. 1H NMR (CD₃OD, 300 MHz): δ 8.56 (s, 1H), 3.94 (s, 3H). MS calc'd [M+H]⁺ 171.0, found 171.2.

Step 4: Into a 250 mL sealed tube containing a solution of 1-methyl-4-nitro-1H-pyrazole-3-carboxamide (2.0 g, 12 mmol) in dichloromethane (100 mL) was added N,N-diisopropylethylamine (13 mL, 71 mmol) at 0° C. To this reaction mixture was added phosphorous oxychloride (3.3 mL, 35 mmol) dropwise and the mixture was stirred at room temperature for 1 h. The reaction was treated with saturated sodium bicarbonate solution and extracted with dichloromethane. The combined organics were washed with water and brine, dried over anhydrous sodium sulfate, filtered and concentrated under reduced pressure. The residue was purified by flash chromatography eluting with ethyl acetate in petroleum ether (25-30%) to afford 1-methyl-4-nitro-1H-pyrazole-3-carbonitrile as a solid. ¹H NMR (CDCl₃, 400 MHz): δ 8.24 (s, 1H), 4.09 (s, 3H).

Step 5: Into a 250 mL round bottom flask containing a solution of 1-methyl-4-nitro-1H-pyrazole-3-carbonitrile (3.5 g, 23 mmol) in methanol (100 mL) at room temperature was added palladium on carbon (0.5 g, 15% w/w) and the reaction mixture was stirred at room temperature under hydrogen bladder atmosphere for 2 h. The reaction mixture was filtered through celite and washed with methanol and dichloromethane. The filtrate was concentrated under reduced pressure to afford 4-amino-1-methyl-1H-pyrazole-3-carbonitrile as a solid. ¹H NMR (CD₃OD, 400 MHz): δ 7.22 (s, 1H), 3.84 (s, 3H). MS calc'd [M+H]⁺ 123.1, found 123.4.

Intermediate 4

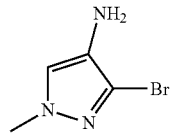

3-Bromo-1-methyl-1H-pyrazol-4-amine

Step 1: Into a 250 mL round bottom flask containing a solution of 3-amino-1-methyl-1H-pyrazole (5.0 g, 52 mmol) in dichloromethane (100 mL) at 0° C. was added triethylamine (18 mL, 129 mmol). After 10 min, trifluoroacetic anhydride (9.5 mL, 67 mmol) was added and the reaction mixture was stirred at room temperature for 2 h. The reaction mixture was diluted with dichloromethane (50 mL), washed with water and brine, dried over anhydrous sodium sulfate, filtered and concentrated under reduced pressure to afford 2,2,2-trifluoro-N-(1-methyl-1H-pyrazol-3-yl)acetamide as a solid. ¹H NMR (CDCl₃, 400 MHz): δ 9.26 (brs, 1H), 7.33 (d, J=2.2 Hz, 1H), 6.73 (d, J=2.2 Hz, 1H), 3.84 (s, 3H). MS calc'd [M+H]⁺ 194.1, found 194.4.

Step 2: Into a 100 mL round bottom flask containing a solution of 2,2,2-trifluoro-N-(1-methyl-1H-pyrazol-3-yl)acetamide (8.5 g, 44 mmol) in concentrated sulfuric acid (14 mL) was added fuming nitric acid (14 mL) at 0° C. dropwise and the reaction was stirred at room temperature for 2 h. The reaction mixture was treated with ice cold water and extracted with ethyl acetate. The combined organic fractions were washed with saturated sodium bicarbonate solution, water and brine, dried over anhydrous sodium sulfate, filtered and concentrated under reduced pressure to afford 2,2,2-trifluoro-N-(1-methyl-4-nitro-1H-pyrazol-3-yl)acetamide (8.5 g) which was taken to the next step without further purification. ¹H NMR (CDCl₃, 300 MHz): δ 9.86 (s, 1H), 8.15 (s, 1H), 3.98 (s, 3H). MS calc'd [M−H]⁺237.0, found 237.0.

Step 3: Into a 500 mL round bottom flask containing a solution of 2,2,2-trifluoro-N-(1-methyl-4-nitro-1H-pyrazol-3-yl)acetamide (8.5 g, 36 mmol) in methanol (200 mL) and water (50 mL) was added potassium carbonate (12.5 g, 89 mmol) and the reaction was stirred at room temperature for 24 h. The mixture was concentrated under reduced pressure and the residue was dissolved in ethyl acetate (150 mL), washed with water and brine, dried over anhydrous sodium sulfate, filtered and concentrated under reduced pressure. The residue was purified by column chromatography eluting with ethyl acetate to afford 1-methyl-4-nitro-1H-pyrazol-3-amine as a solid. $^1$H NMR (DMSO-d$_6$, 300 MHz): δ 8.44 (s, 1H), 6.22 (s, 2H), 3.65 (s, 3H). MS calc'd [M+H]$^+$ 143.1, found 143.2.

Step 4: Into a 250 mL round bottom flask containing a solution of copper(II) bromide (3.0 g, 14 mmol) and tert-butyl nitrite (1.7 mL, 14 mmol) in acetonitrile (150 mL) was added 1-methyl-4-nitro-1H-pyrazol-3-amine (2 g, 14 mmol) in acetonitrile (20 mL) at 0° C. and the reaction was stirred at room temperature for 2 h. The reaction mixture was concentrated under reduced pressure. The residue was dissolved in ethyl acetate (120 mL), washed with water and brine, dried over anhydrous sodium sulfate, filtered and concentrated under reduced pressure. The residue was purified by column chromatography eluting with ethyl acetate in petroleum ether (20-30%) to afford 3-bromo-1-methyl-4-nitro-1H-pyrazole as a solid. $^1$H NMR (CDCl$_3$, 300 MHz): δ 8.25 (s, 1H), 3.89 (s, 3H).

Step 5: Into a 100 mL round bottom flask containing a solution of 3-bromo-1-methyl-4-nitro-1H-pyrazole (1.0 g) in ethyl acetate (50 mL) at room temperature was added Raney Nickel (700 mg) and the reaction mixture was stirred at room temperature for 16 h under hydrogen atmosphere. The reaction mixture was filtered through celite and washed with ethyl acetate. The filtrate was concentrated under reduced pressure and purified by flash chromatography eluting with ethyl acetate in petroleum ether (40-50%) to afford 3-bromo-1-methyl-1H-pyrazol-4-amine as a liquid. $^1$H NMR (CD$_3$OD, 400 MHz): δ 7.18 (s, 1H), 3.77 (s, 3H). MS calc'd [M+H]$^+$ 176.0, found 176.2.

Intermediate 5

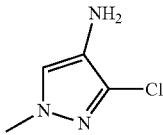

3-Chloro-1-methyl-1H-pyrazol-4-amine

Step 1: Into a 250 mL round bottom flask containing a solution of 1-methyl-4-nitro-1H-pyrazol-3-amine (4.0 g, 28 mmol) in acetonitrile (100 mL) was added concentrated hydrochloric acid (8 mL) dropwise at 0° C. To this reaction mixture was added sodium nitrite (8.0 g, 116 mmol) in portions and the reaction mixture was gradually brought to room temperature and stirred for 16 h. The reaction mixture was cooled to 0° C., treated with water (30 mL) and extracted with ethyl acetate (2×50 mL). The combined organics were washed with saturated sodium bicarbonate solution, water and brine, dried over anhydrous sodium sulfate, filtered and concentrated under reduced pressure. The residue was purified by column chromatography eluting with ethyl acetate in petroleum ether (20-30%) to furnish 3-chloro-1-methyl-4-nitro-1H-pyrazole as a solid. $^1$H NMR (CDCl$_3$, 300 MHz): δ 8.25 (s, 1H), 3.98 (s, 3H).

Step 2: Into a 100 mL round bottom flask containing a solution of 3-chloro-1-methyl-4-nitro-1H-pyrazole (2.0 g) in ethyl acetate (50 mL) was added Raney Ni (1.0 g) and the reaction mixture was stirred under hydrogen atmosphere for 24 h. The reaction mixture was filtered through celite and washed with ethyl acetate. The filtrate was concentrated under reduced pressure and purified by flash chromatography eluting with ethyl acetate in petroleum ether (40-50%) to afford 3-chloro-1-methyl-1H-pyrazol-4-amine as an oil. $^1$H NMR (CD$_3$OD, 400 MHz): δ 7.17 (s, 1H), 3.73 (s, 3H).

Intermediate 6

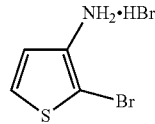

2-Bromo-3-aminothiophene hydrobromide

Step 1: Into a 100 mL round bottom flask containing a solution of thiophene-3-carboxylic acid (4.0 g, 31 mmol) in toluene (40 mL) were added diphenylphosphoryl azide (9.5 g, 34 mmol) and N,N-diisopropylethylamine (6.7 mL, 38 mmol) at 0° C. and the reaction was stirred at room temperature for 1 h. The reaction mixture was cooled to 0° C., treated with tert-butanol (12 mL, 124 mmol) and heated to 120° C. for 5 h. The reaction mixture was concentrated under reduced pressure and purified by flash chromatography eluting with ethyl acetate in petroleum ether (2-5%) to afford tert-butyl thiophen-3-ylcarbamate as a solid. $^1$H NMR (CDCl$_3$, 400 MHz): δ 7.23-7.21 (m, 2H), 6.93 (d, J=5.6 Hz, 1H), 6.71 (brs, 1H), 1.54 (s, 9H).

Step 2: Into a 100 mL round bottom flask containing a solution of tert-butyl thiophen-3-ylcarbamate (4.2 g, 21 mmol) in carbon tetrachloride (40 mL) was added N-bromosuccinimide (7.5 g, 42 mmol) and the reaction mixture was heated at 80° C. for 2 h. The reaction mixture was diluted with ethyl acetate (100 mL), washed with water and brine, dried over anhydrous sodium sulfate, filtered and concentrated under reduced pressure. The residue was purified by flash chromatography eluting with ethyl acetate in petroleum ether (2-5%) to afford tert-butyl (2-bromothiophen-3-yl)carbamate as a solid. $^1$H NMR (CDCl$_3$, 400 MHz): δ 7.59 (d, J=3.3 Hz, 1H), 7.26 (d, J=3.4 Hz, 1H), 6.58 (brs, 1H), 1.54 (s, 9H). MS calc'd [M+H]$^+$ 278.0, found 278.2.

Step 3: Into a 10 mL round bottom flask containing a solution of tert-butyl (2-bromothiophen-3-yl)carbamate (500 mg) in dichloromethane (5 mL) was added HBr in acetic acid (0.5 mL) dropwise at 0° C. and reaction mixture was stirred at room temperature for 2 h. The reaction mixture was concentrated under reduced pressure and triturated using diethyl ether to afford 2-bromothiophen-3-amine hydrobromide as a solid. $^1$H NMR (DMSO-d$_6$, 400 MHz): (7.66 (d, J=5.8 Hz, 1H), 6.96 (d, J=5.8 Hz, 1H).

The following intermediate was prepared in an analogous manner of that described in Intermediate 6.

| Intermediate # | Structure | IUPAC Name | Exact Mass [M + 11]+ |
|---|---|---|---|
| 7 | 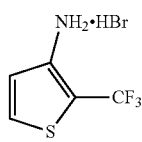 | 2-chlorothiophen-3-amine hydrochloride | Calc'd 134.0, found 134.4 |

Intermediate 8

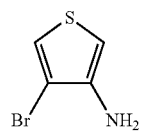

2-(Trifluoromethyl)thiophen-3-amine hydrobromide

Step 1: Into a 50 mL round bottom flask containing a solution of tert-butyl thiophen-3-ylcarbamate (1.0 g, 5 mmol) in tert-butanol (30 mL) were added 1-(trifluoromethyl)-1λ³,2-benziodoxol-3(1H)-one (3.3 g, 10 mmol) and copper(I) chloride (100 mg, 1 mmol) and the reaction was heated at 115° C. for 8 h. The reaction mixture was diluted with ethyl acetate (20 mL) and washed with saturated sodium bicarbonate solution, water and brine. The solution was dried over anhydrous sodium sulfate, filtered, concentrated under reduced pressure and purified by flash column chromatography eluting with ethyl acetate in petroleum ether (15-20%) to furnish tert-butyl (2-(trifluoromethyl)thiophen-3-yl)carbamate as a solid. $^1$H NMR (CDCl$_3$, 300 MHz): δ 7.77 (d, J=4.4 Hz, 1H), 7.38 (d, J=5.5 Hz, 1H), 6.91 (brs, 1H), 1.53 (s, 9H).

Step 2: Into a 25 mL round bottom flask tert-butyl (2-(trifluoromethyl)thiophen-3-yl)carbamate (800 mg) in dichloromethane (10 mL) was added HBr in acetic acid (1 mL) at 0° C. and the mixture was stirred at room temperature for 2 h. The reaction mixture was concentrated under reduced pressure and triturated using diethyl ether to afford 2-(trifluoromethyl)thiophen-3-amine hydrobromide as a solid. $^1$H NMR (DMSO-d$_6$, 300 MHz): δ 7.51 (d, J=5.2 Hz, 1H), 6.59 (d, J=4.0 Hz, 1H).

Intermediate 9

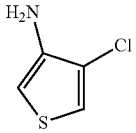

4-Bromo-3-aminothiophene

Step 1: Into a 100 mL round bottom flask containing a solution of 3,4-dibromothiophene (5.0 g, 21 mmol) in toluene (50 mL) were added benzophenone imine (4.1 g, 23 mmol), palladium acetate (140 mg, 0.6 mmol), 2,2'-bis(diphenylphosphino)-1,1'-binaphthyl (510 mg, 0.83 mmol) and cesium carbonate (13.4 g, 41 mmol) and the reaction mixture was degassed for 15 min using nitrogen gas and heated at 110° C. for 16 h. The reaction mixture was filtered through celite and washed with ethyl acetate. The filtrate was concentrated under reduced pressure and purified by flash column chromatography eluting with ethyl acetate in petroleum ether (2-5%) to afford N-(4-bromothiophen-3-yl)-1,1-diphenylmethanimine as a solid. $^1$H NMR (CDCl$_3$, 400 MHz): δ 7.85-7.82 (m, 3H), 7.64-7.60 (m, 2H), 7.53-7.49 (m, 3H), 7.45-7.42 (m, 1H), 7.39-7.36 (m, 2H), 7.23-7.18 (m, 1H). MS calc'd [M+H]+ 342.0, found 342.0.

Step 2: Into a 50 mL round bottom flask containing a solution of N-(4-bromothiophen-3-yl)-1,1-diphenylmethanimine (4.0 g, 12 mmol) in dichloromethane (20 mL) was added hydrochloric acid (4 M solution in 1,4-dioxane, 10 mL) at 0° C. and the reaction was stirred at room temperature for 4 h. The reaction mixture was concentrated under reduced pressure, triturated using diethyl ether and dried under high vacuum to afford 4-bromothiophen-3-amine hydrochloride as a solid. $^1$H NMR (CDCl$_3$, 400 MHz): (7.15 (d, J=3.6 Hz, 1H), 6.25 (d, J=3.6 Hz, 1H). MS calc'd [M+H]$^+$ 177.9, found 178.2.

Intermediate 10

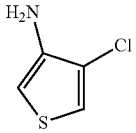

4-Chlorothiophen-3-amine

Step 1: Into a 250 mL round bottom flask containing a solution of methyl 4-aminothiophene-3-carboxylate (2.5 g, 16 mmol) in concentrated hydrochloric acid (21 mL) was added sodium nitrite (1.2 g, 18 mmol) in water (5 mL) dropwise at 0° C. and the reaction mixture was stirred at for 1 h. The mixture was treated with copper(I) chloride (2.5 g, 19 mmol) in chloroform (25 mL) and heated at 50° C. for 16 h. The reaction mixture was cooled to room temperature, treated with saturated sodium carbonate solution and extracted with dichloromethane (3×50 mL). The combined organic layers were washed with water and brine, dried over anhydrous sodium sulfate, filtered and concentrated under reduced pressure. The residue was purified by flash chromatography eluting with ethyl acetate in petroleum ether (0-4%) to furnish methyl 4-chlorothiophene-3-carboxylate as a liquid. $^1$H NMR (CDCl$_3$, 400 MHz): δ 8.13 (d, J=3.7 Hz, 1H), 7.20 (d, J=3.7 Hz, 1H), 3.90 (s, 3H).

Step 2: Into a 25 mL round bottom flask containing a solution of methyl 4-chlorothiophene-3-carboxylate (600 mg, 3.4 mmol) in tetrahydrofuran (6 mL) and water (1 mL) was added lithium hydroxide monohydrate (240 mg, 10 mmol) and the reaction was stirred at room temperature for 16 h. The mixture was concentrated under reduced pressure and acidified to pH 2 using diluted hydrochloric acid (1.5 N). The reaction mixture was extracted with ethyl acetate. The combined organic fractions were washed with water and brine, dried over anhydrous sodium sulfate, filtered and concentrated under reduced pressure to afford 4-chlorothiophene-3-carboxylic acid as a liquid. $^1$H NMR (CDCl$_3$, 300

MHz): δ 8.29 (d, J=3.7 Hz, 1H), 6.57 (d, J=3.6 Hz, 1H). MS calc'd [M−H]⁺161.0, found 161.0.

Step 3: Into a 100 mL round bottom flask containing a solution of 4-chlorothiophene-3-carboxylic acid (500 mg, 3 mmol) in toluene (20 mL) were added diphenylphosphoryl azide (2.5 g, 3.4 mmol) and N,N-diisopropylethylamine (0.7 mL, 3.7 mmol) and the reaction was stirred at room temperature for 1 h. To this mixture was added tert-butanol (1.2 mL, 12 mmol) and the mixture was heated at 100° C. for 3 h. The reaction mixture was concentrated under reduced pressure, diluted with ethyl acetate (120 mL), washed with water and brine, dried over anhydrous sodium sulfate, filtered and concentrated under reduced pressure. The residue was purified by column chromatography eluting with ethyl acetate in petroleum ether (2-4%) to furnish tert-butyl (4-chlorothiophen-3-yl)carbamate as a solid. ¹H NMR (CDCl₃, 400 MHz): (7.53 (d, J=4.8 Hz, 1H), 7.11 (d, J=3.6 Hz, 1H), 6.82 (brs, 1H), 1.43 (s, 9H). MS calc'd [M−Boc+H]⁺134.0, found 134.4.

Step 4: Into a 10 mL round bottom flask containing a solution of tert-butyl (4-chlorothiophen-3-yl)carbamate (400 mg, 1.7 mmol) in dichloromethane (4 mL) was added hydrochloric acid solution (4M solution in 1,4-dioxane, 0.3 mL) and the reaction mixture was stirred at room temperature for 2 h. The reaction mixture was concentrated under reduced pressure, triturated with diethyl ether and dried under high vacuum to afford 4-chlorothiophen-3-amine hydrochloride as a solid. ¹H NMR (CD₃OD, 400 MHz): δ 7.64 (s, 2H). MS calc'd [M+H]⁺134.0, found 134.4.

Intermediate 11

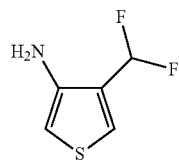

4-(Difluoromethyl)thiophen-3-amine

Step 1: Into a 100 mL round bottom flask containing a solution of 3,4-dibromothiophene (4.0 g, 17 mmol) in diethyl ether (50 mL) was added n-butyl lithium in hexane (1 M solution in hexanes, 17 mL, 17 mmol) at −78° C. over 15 min. To this mixture was added N,N-dimethylformamide and the reaction was stirred for 3 h. The reaction mixture was treated with saturated ammonium chloride solution and extracted with diethyl ether (2×50 mL). The combined organics were washed with water and brine, dried over anhydrous sodium sulfate, filtered and concentrated under reduced pressure to furnish 4-bromothiophene-3-carbaldehyde as a liquid which was directly taken to the next step without further purification. ¹H NMR (CDCl₃, 400 MHz): δ 9.99 (s, 1H), 8.17 (s, 1H), 7.76 (s, 1H).

Step 2: Into a 50 mL round bottom flask containing a solution of 4-bromothiophene-3-carbaldehyde (3.5 g, 18 mmol) in dichloromethane (40 mL) was added diethylaminosulfur trifluoride (7.3 mL, 55 mmol) at 0° C. and the reaction was stirred room temperature for 16 h.

The reaction mixture was diluted with dichloromethane (20 mL) and washed with saturated sodium bicarbonate solution, water and brine. The solution was dried over anhydrous sodium sulfate, filtered, concentrated under reduced pressure and purified by flash column chromatography eluting with ethyl acetate in petroleum ether (2-5%) to furnish 3-bromo-4-(difluoromethyl)thiophene as a liquid. ¹H NMR (CDCl₃, 300 MHz): δ 7.68 (s, 1H), 7.35 (s, 1H), 6.67 (t, J=55.1 Hz, 1H).

Step 3: A solution of 3-bromo-4-(difluoromethyl)thiophene (800 mg, 4 mmol) in N,N-dimethylformamide (10 mL) at 0° C. was purged with ammonia gas for 1 h. To this mixture were added potassium phosphate tribasic (2.4 g, 11 mmol) and copper(II) acetylacetonate (300 mg, 1.9 mmol) and the reaction mixture was heated at 90° C. for 16 h. The reaction mixture was diluted with ethyl acetate (20 mL), washed with water and brine, dried over anhydrous sodium sulfate, filtered, concentrated under reduced pressure and purified by flash column chromatography eluting with ethyl acetate in petroleum ether (15-20%) to furnish 4-(difluoromethyl)thiophen-3-amine as a liquid. ¹H NMR (CDCl₃, 300 MHz): δ 7.36 (d, J=2.9 Hz, 1H), 6.63 (t, J=55.7 Hz, 1H), 6.24 (d, J=3.3 Hz, 1H). MS calc'd [M+H]⁺ 150.0, found 150.4.

Intermediate 12

2-(Difluoromethyl)aniline hydrobromide

Step 1: Into a 250 mL round bottom flask containing a solution of methyl 2-formylbenzoate (5.0 g, 30 mmol) in dichloromethane (80 mL) were added diethylaminosulfur trifluoride (7 mL, 52 mmol) and methanol (1.5 mL) at −5° C. and the reaction was stirred at room temperature for 16 h. The reaction mixture was diluted with dichloromethane (20 mL) and washed with saturated sodium bicarbonate solution, water and brine. The solution was dried over anhydrous sodium sulfate, filtered and concentrated under reduced pressure to afford methyl 2-(difluoromethyl)benzoate as an oil which was taken to the next step without further purification.

Step 2: Into a 100 mL round bottom flask containing a solution of methyl 2-(difluoromethyl)benzoate (4.3 g, 23 mmol) in tetrahydrofuran (30 mL) and water (15 mL) was added lithium hydroxide monohydrate (2.9 g, 69 mmol) at 0° C. and the reaction mixture was stirred at room temperature for 16 h. The reaction mixture was concentrated under reduced pressure and acidified to pH 2 using diluted hydrochloric acid (1.5 N). The reaction mixture was extracted with ethyl acetate. The combined organics were washed with water and brine, dried over anhydrous sodium sulfate, filtered and concentrated under reduced pressure to afford 2-(difluoromethyl)benzoic acid (4.0 g). The crude product was taken to the next step without further purification. MS calc'd [M−H]⁺171.0, found 171.0.

Step 3: Into a 100 mL round bottom flask containing a solution of 2-(difluoromethyl)benzoic acid (4.0 g, 23 mmol) in toluene (50 mL) were added diphenylphosphoryl azide (5.5 mL, 26 mmol), N,N-diisopropylethylamine (5 mL, 28 mmol) and tert-butanol (7 mL) and the mixture was stirred at room temperature for 30 min and at 110° C. for 16 h. The reaction mixture was concentrated under reduced pressure. The residue was dissolved in ethyl acetate (120 mL), washed with water and brine, dried over anhydrous sodium sulfate, filtered and concentrated under reduced pressure. The residue was purified by column chromatography eluting with ethyl acetate in petroleum ether (5-10%) to furnish tert-butyl (2-(difluoromethyl)phenyl)carbamate as a liquid. $^1$H NMR (CDCl$_3$, 300 MHz): δ 8.01 (d, J=8.2 Hz, 1H), 7.49-7.38 (m, 2H), 7.14 (t, J=7.5 Hz, 1H), 6.86 (brs, 1H), 6.68 (t, J=55.1 Hz, 1H), 1.53 (s, 9H).

Step 4: Into a 10 mL round bottom flask containing a solution of tert-butyl (2-(difluoromethyl)phenyl)carbamate (650 mg) in dichloromethane (5 mL) was added HBr in acetic acid (0.5 mL) at 0° C. and the reaction was stirred at room temperature for 2 h. The reaction mixture was concentrated under reduced pressure, triturated with diethyl ether and dried under high vacuum to afford 2-(difluoromethyl)aniline hydrobromide as a solid. $^1$H NMR (DMSO-d$_6$, 400 MHz): δ 7.37-7.35 (m, 1H), 7.32-7.28 (m, 1H), 7.07 (t, J=55.2 Hz, 1H), 6.95-6.93 (m, 1H), 6.88-6.84 (m, 1H). MS calc'd [M+H]$^+$ 144.1, found 144.4.

Intermediate 13

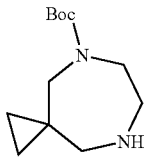 [SMILES: CC(C)(C)OC(=O)N1CCNCC2(CC2)C1]

tert-Butyl 5,8-diazaspiro[2.6]nonane-5-carboxylate

Step 1: Into a 5 L 4 necked round bottomed flask was placed a solution of diethyl malonate (300 g, 1.87 mol) and 1,2-dibromoethane (634.5 g, 3.38 mol) in DMSO (1.5 L). The mixture was treated with K$_2$CO$_3$ (1020 g, 7.39 mol) and Bu$_4$NHSO$_4$ (6.4 g, 19 mmol). The resulting solution was allowed to stir for 48 h at room temperature. The reaction mixture was treated with 2 L of H$_2$O and extracted with 1.5 L of EtOAc (3×). The organic layers were combined, dried over Na$_2$SO$_4$ and concentrated under reduced pressure. The residue was distilled under 5-10 mmHg vacuum at 64-65° C. This resulted in 400 g (90%) of diethyl cyclopropane-1,1-dicarboxylate as an oil.

Step 2: Into a 100 mL 3 necked round bottomed flask was placed THF (50 mL), then added LiAlH$_4$ (2 g, 53 mmol) in several batches. This was followed by the addition of a solution of diethyl cyclopropane-1,1-dicarboxylate (5 g, 27 mmol) in THF (10 mL) dropwise with stirring, while cooling to 0° C. The resulting solution was allowed to stir for 1 h at 0-5° C. in an ice bath. The reaction mixture was then treated with 2 mL of H$_2$O, 6 mL of 15% NaOH solution and 2 mL of H$_2$O. The mixture was filtered and the filtrate was concentrated under reduced pressure. The residue was extracted with 50 mL of EtOAc. The organic layer was dried over Na$_2$SO$_4$ and concentrated under reduced pressure to afford cyclopropane-1,1-diyldimethanol as a liquid.

Step 3: Into a 2 L 3 necked round bottomed flask were placed a solution of cyclopropane-1,1-diyldimethanol (42 g, 410 mmol) in DCM (200 mL) and DMAP (126 g, 1.03 mol). The mixture was treated with a solution of TsCl (173 g, 907 mmol) in DCM (500 mL) dropwise, while cooling to 0° C., over 30 min. The resulting solution was allowed to stir for 2.5 h at room temperature. The reaction mixture was washed with H$_2$O, HCl (1N) and brine, dried over Na$_2$SO$_4$ and concentrated under reduced pressure. This resulted in cyclopropane-1,1-diyldimethanediyl bis(4-methylbenzenesulfonate) as a solid Step 4: Into a 5 L 4 necked round bottomed flask was placed a solution of 4-methylbenzene-1-sulfonyl chloride (487 g, 2.55 mol) in ethyl ether (1 L). To the mixture was added a solution of ethane-1,2-diamine (77 g, 1.3 mol) and sodium hydroxide (102 g, 2.55 mol) in H$_2$O (1 L) dropwise while cooled to 0° C. The resulting solution was allowed to stir for 30 min at 0° C. in an ice bath, then overnight at room temperature. A filtration was performed and the filter cake was washed 2 times with H$_2$O and dried in an oven. This resulted in (crude) N,N-ethane-1,2-diylbis (4-methylbenzenesulfonamide) as a solid.

Into a 5 L 4 necked round bottom flask were placed N,N-ethane-1,2-diylbis(4-methylbenzenesulfonamide) (150 g, 408 mmol), cyclopropane-1,1-diyldimethanediyl bis(4-methylbenzenesulfonate) (200 g, 487 mmol), 18-crown-6 (53 g, 200 mmol) and THF (2 L) followed by the addition of a solution of t-BuOK (100 g, 893 mmol) in THF (500 mL) dropwise with stirring at −30° C. The resulting solution was allowed to stir for 2 days at room temperature. The resulting mixture was concentrated under reduced pressure to remove most of THF. The residual solution was diluted with 1500 mL of H$_2$O. The precipitate was collected by filtration and dried. The residue was purified by eluting through a silica gel column with dichloromethane/petroleum ether (1:10-1:2). This resulted in 5,8-bis[(4-methylphenyl)sulfonyl]-5,8-diazaspiro[2.6]nonane as a solid.

Step 5: Into a 5 L 4 necked round bottomed flask was placed a solution of 5,8-bis[(4-methylphenyl)sulfonyl]-5,8-diazaspiro[2.6]nonane (100 g, 230 mmol) in MeOH (1500 mL). To the mixture was added magnesium (27.4 g, 1.14 mol) batchwise when the reaction mixture was warmed at 40° C. The resulting mixture was allowed to stir for 2 h at room temperature. The resulting mixture was concentrated under reduced pressure to remove MeOH. The residue was diluted with 500 mL of EtOAc and filtered. The filtrate was treated with a solution of oxalic acid (23 g, 255 mmol) in Et$_2$O (500 mL). The precipitate was collected by filtration and dried. This resulted in 5-[(4-methylphenyl)sulfonyl]-5,8-diazaspiro[2.6]nonane ethanedioate as a solid.

Step 6: Into a 2 L 3 necked round bottomed flask was placed a solution of 5-[(4-methylphenyl)sulfonyl]-5,8-diazaspiro[2.6]nonane ethanedioate (50 g, 121.48 mmol, 90%) in DCM (800 mL) and Et$_3$N (31 g, 310 mmol). To the mixture was added Boc$_2$O (26 g, 119 mmol) at 0-5° C. The resulting solution was allowed to stir overnight at room temperature. The reaction mixture was washed with 3×500 mL of H$_2$O and 1×500 mL of brine. The organic layer was dried over Na$_2$SO$_4$ and concentrated under reduced pressure. This resulted in tert-butyl 8-[(4-methylphenyl)sulfonyl]-5,8-diazaspiro[2.6]nonane-5-carboxylate as an oil.

Step 7: Into a 3 L 3 necked round bottomed flask was placed a solution of tert-butyl 8-[(4-methylphenyl)sulfonyl]-5,8-diazaspiro[2.6]nonane-5-carboxylate (110 g, 232 mmol, 80%) in MeOH (1800 mL). To the mixture was added Mg (36 g, 1.50 mol) in several batches at 40° C. The resulting solution was allowed to stir for 1 h at room temperature. The resulting mixture was concentrated under reduced pressure. The residue was diluted with 1 L of EtOAc and filtered. The filtrate was treated with a solution of oxalic acid in ether to precipitate the product. The solid was collected by filtration and washed 2 times with ether. This resulted in tert-butyl 5,8-diazaspiro[2.6]nonane-5-carboxylate ethanedioate as a solid. ¹H-NMR (400 MHz, D$_2$O): δ 0.71-0.736 (d, J=9.6 Hz, 2H), 0.75-0.78 (d, J=9.6 Hz, 2H), 0.77 (m, 4H), 1.42 (s, 9H), 3.18 (s, 2H), 3.33-3.39 (m, 4H), 3.78 (s, 1H). MS [M+H]$^+$ 227.

Example 1

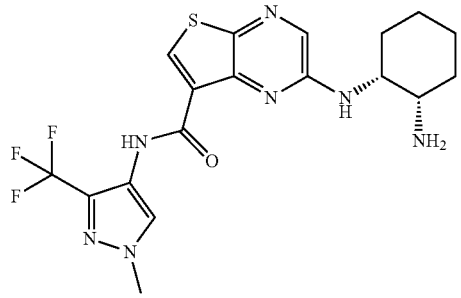 [SMILES: Cn1cc(NC(=O)c2csc3ncc(N[C@@H]4CCCC[C@@H]4N)nc23)c(C(F)(F)F)n1]

2-{[(1R,2S)-2-Aminocyclohexyl]amino}-N-[1-methyl-3-(trifluoromethyl)-1H-pyrazol-4-yl]thieno[2,3-b]pyrazine-7-carboxamide (IRAK4 IC$_{50}$=1 nM)

Step 1: Into a 25 mL round bottom flask containing a solution of 2-chlorothieno[2,3-b]pyrazine-7-carboxylic acid (0.6 g, 2.8 mmol) in N,N-dimethylformamide (3 mL) were added N,N-diisopropylethylamine (1.7 mL, 9.8 mmol), 1-[bis(dimethylamino)methylene]-1H-1,2,3-triazolo[4,5-b]pyridinium 3-oxid hexafluorophosphate (1.6 g, 4.2 mmol) and 1-methyl-3-(trifluoromethyl)-1H-pyrazol-4-amine (0.55 g, 3.4 mmol) and the reaction was stirred at room temperature for 16 h. The reaction mixture was treated with ice-cooled water (20 mL) and extracted with ethyl acetate (3×50 mL). The combined organics were washed with brine (50 mL), dried over anhydrous sodium sulfate, filtered, concentrated under reduced pressure and purified by flash chromatography (silica gel) eluting with 30-35% ethyl acetate in petroleum ether to afford 2-chloro-N-(1-methyl-3-(trifluoromethyl)-1H-pyrazol-4-yl)thieno[2,3-b]pyrazine-7-carboxamide as a solid. ¹H NMR (CDCl$_3$, 300 MHz): δ 10.94 (brs, 1H), 8.96 (s, 1H), 8.67 (s, 1H), 8.39 (s, 1H), 3.99 (s, 3H). MS calc'd [M−H]$^+$360.0, found 360.0.

Step 2: Into a 5 mL microwave vial charged with a solution of 2-chloro-N-(1-methyl-3-(trifluoromethyl)-1H-pyrazol-4-yl)thieno[2,3-b]pyrazine-7-carboxamide (150 mg, 0.4 mmol) in ethanol (2 mL) were added tert-butyl ((1S,2R)-2-aminocyclohexyl)carbamate (98 mg, 0.46 mmol) and N,N-diisopropylethylamine (0.15 mL, 0.83 mmol) and the reaction was irradiated at 150° C. under microwave irradiation for 12 h. The reaction mixture was concentrated under reduced pressure and purified by flash chromatography (silica gel) eluting with 30% ethyl acetate in petroleum ether to afford tert-butyl ((1S,2R)-2-((7-((1-methyl-3-(trifluoromethyl)-1H-pyrazol-4-yl)carbamoyl)thieno[2,3-b]pyrazin-2-yl)amino)cyclohexyl)carbamate as a solid. MS calc'd [M+H]$^+$ 540.2, found 540.0.

Step 3: Into a solution of tert-butyl ((1S,2R)-2-((7-((1-methyl-3-(trifluoromethyl)-1H-pyrazol-4-yl)carbamoyl)thieno[2,3-b]pyrazin-2-yl)amino)cyclohexyl)carbamate (40 mg, 0.07 mmol) in dichloromethane (1 mL) was added trifluoroacetic acid (0.5 mL) and the reaction mixture was stirred at room temperature for 2 h. The reaction mixture was concentrated under reduced pressure and purified by preparative HPLC to afford 2-(((1R,2S)-2-aminocyclohexyl)amino)-N-(1-methyl-3-(trifluoromethyl)-1H-pyrazol-4-yl)thieno[2,3-b]pyrazine-7-carboxamide trifluoroacetate as a solid. ¹H NMR (CD$_3$OD, 400 MHz): δ 8.78 (s, 1H), 8.35 (s, 1H), 8.25 (s, 1H), 4.78-4.77 (m, 1H), 4.00 (s, 3H), 3.56-3.54 (m, 1H), 1.96-1.92 (m, 1H), 1.85-1.74 (m, 5H), 1.67-1.59 (m, 2H). MS calc'd [M+H]$^+$ 440.1, found 440.2.

The following examples were prepared in an analogous manner of that described in Example 1.

| Example # | IRAK4 IC$_{50}$ (nM) | Structure | IUPAC Name | Exact Mass [M + H]$^+$ |
|---|---|---|---|---|
| 2 | 42 | 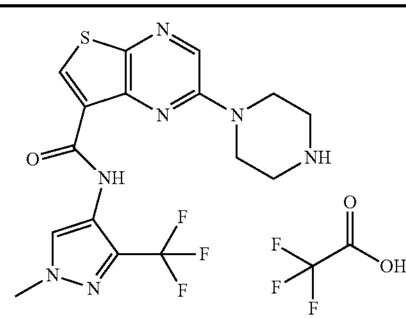 | N-[1-methyl-3-(trifluoromethyl)-1H-pyrazol-4-yl]-2-piperazin-1-ylthieno[2,3-b]pyrazine-7-carboxamide trifluoroacetate | Calc'd 412.1, found 412.2 |
| 3 | 100 | 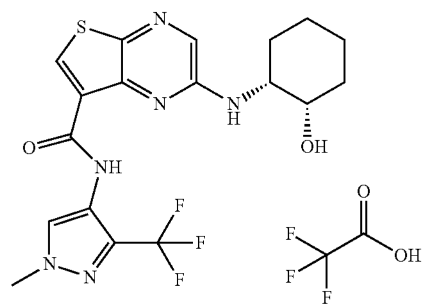 [SMILES: Cn1cc(NC(=O)c2csc3ncc(N[C@@H]4CCCC[C@@H]4O)nc23)c(C(F)(F)F)n1 ; O=C(O)C(F)(F)F] | 2-{[(1R,2S)-2-hydroxycyclohexyl]amino}-N-[1-methyl-3-(trifluoromethyl)-1H-pyrazol-4-yl]thieno[2,3-b]pyrazine-7-carboxamide trifluoroacetate | Calc'd 441.1, found 441.2 |

-continued

| Example # | IRAK4 IC$_{50}$ (nM) | Structure | IUPAC Name | Exact Mass [M + H]$^+$ |
|---|---|---|---|---|
| 4 | 0.8 | 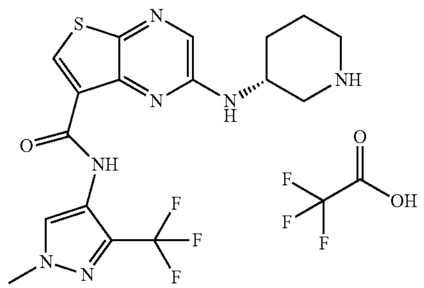 [SMILES: Cn1cc(NC(=O)c2csc3ncc(N[C@@H]4CCCNC4)nc23)c(C(F)(F)F)n1 ; O=C(O)C(F)(F)F] | N-[1-methyl-3-(trifluoromethyl)-1H-pyrazol-4-yl]-2-[(3R)-piperazin-3-ylamino]thieno[2,3-b]pyrazine-7-carboxamide trifluoroacetate | Calc'd 426.1, found 426.2 |
| 5 | 332 | 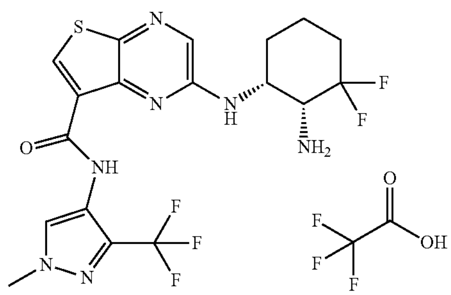 [SMILES: Cn1cc(NC(=O)c2csc3ncc(N[C@@H]4CCCC(F)(F)[C@@H]4N)nc23)c(C(F)(F)F)n1 ; O=C(O)C(F)(F)F] | 2-{[(1R,2R)-2-amino-3,3-difluorocyclohexyl]amino}-N-[1-methyl-3-(trifluoromethyl)-1H-pyrazol-4-yl]thieno[2,3-b]pyrazine-7-carboxamide trifluoroacetate | Calc'd 476.1, found 476.2 |
| 6 | 17 | 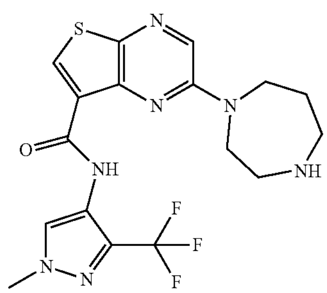 [SMILES: Cn1cc(NC(=O)c2csc3ncc(N4CCCNCC4)nc23)c(C(F)(F)F)n1] | 2-(1,4-diazepan-1-yl)-N-[1-methyl-3-(trifluoromethyl)-1H-pyrazol-4-yl]thieno[2,3-b]pyrazine-7-carboxamide | 426.1 |
| 7 | 109 | 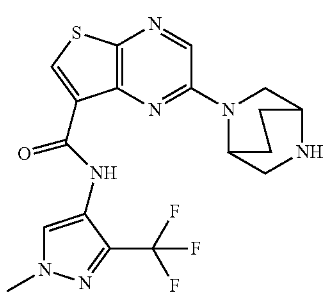 [SMILES: Cn1cc(NC(=O)c2csc3ncc(N4CC5CCC4CN5)nc23)c(C(F)(F)F)n1] | 2-(2,5-diazabicyclo[2.2.2]oct-2-yl)-N-[1-methyl-3-(trifluoromethyl)-1H-pyrazol-4-yl]thieno[2,3-b]pyrazine-7-carboxamide | Calc'd 438.1, found 438.4 |
| 8 | 18 | 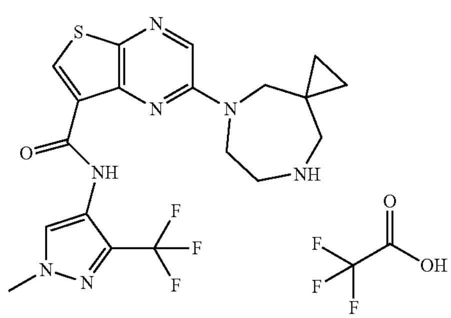 [SMILES: Cn1cc(NC(=O)c2csc3ncc(N4CCNCC5(CC5)C4)nc23)c(C(F)(F)F)n1 ; O=C(O)C(F)(F)F] | 2-(5,8-diazaspiro[2.6]non-5-yl)-N-[1-methyl-3-(trifluoromethyl)-1H-pyrazol-4-yl]thieno[2,3-b]pyrazine-7-carboxamide trifluoroacetate | Calc'd 452.1, found 452.4 |

-continued

| Example # | IRAK4 IC$_{50}$ (nM) | Structure | IUPAC Name | Exact Mass [M + H]$^+$ |
|---|---|---|---|---|
| 9 | 1 | 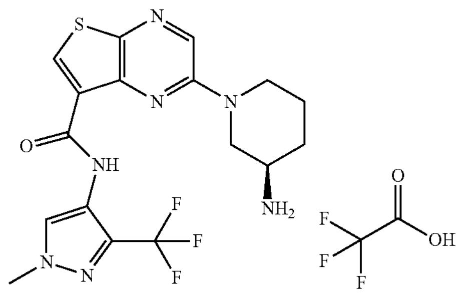 | 2-[(3R)-3-aminopiperidin-1-yl]-N-[1-methyl-3-(trifluoromethyl)-1H-pyrazol-4-yl]thieno[2,3-b]pyrazine-7-carboxamide trifluoroacetate | Calc'd 426.1, found 426.1 |
| 10 | 30 | 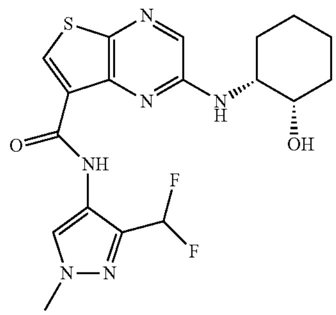 [SMILES: Cn1cc(NC(=O)c2csc3ncc(N[C@@H]4CCCC[C@@H]4O)nc23)c(C(F)F)n1] | N-[3-(difluoromethyl)-1-methyl-1H-pyrazol-4-yl]-2-{[(1R,2S)-2-hydroxycyclohexyl]amino}thieno[2,3-b]pyrazine-7-carboxamide | Calc'd 423.1, found 423.4 |
| 11 | 4 | 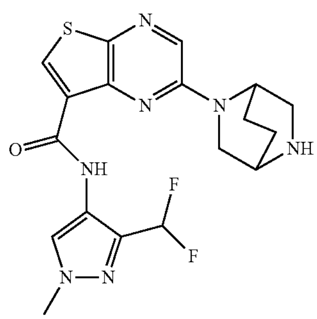 [SMILES: Cn1cc(NC(=O)c2csc3ncc(N4CC5CCC4CN5)nc23)c(C(F)F)n1] | 2-(2,5-diazabicyclo[2.2.2]oct-2-yl)-N-[3-(difluoromethyl)-1-methyl-1H-pyrazol-4-yl]thieno[2,3-b]pyrazine-7-carboxamide | Calc'd 420.1, found 420.4 |
| 12 | 3 | 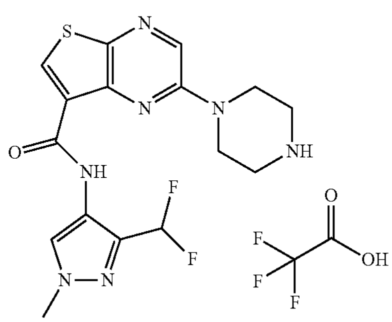 | N-[3-(difluoromethyl)-1-methyl-1H-pyrazol-4-yl]-2-piperazin-1-ylthieno[2,3-b]pyrazine-7-carboxamide trifluoroacetate | Calc'd 394.1, found 394.2 |
| 13 | 6 | 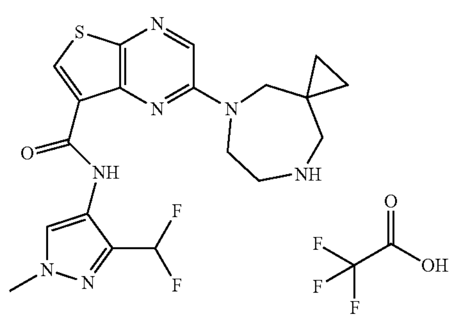 [SMILES: Cn1cc(NC(=O)c2csc3ncc(N4CCNCC5(CC5)C4)nc23)c(C(F)F)n1 ; O=C(O)C(F)(F)F] | 2-(5,8-diazaspiro[2.6]non-5-yl)-N-[3-(difluoromethyl)-1-methyl-1H-pyrazol-4-yl]thieno[2,3-b]pyrazine-7-carboxamide trifluoroacetate | Calc'd 434.0, found 434.4 |

| Example # | IRAK4 IC$_{50}$ (nM) | Structure | IUPAC Name | Exact Mass [M + H]$^+$ |
|---|---|---|---|---|
| 14 | 5 | 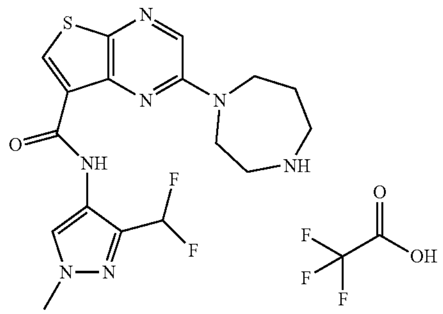 [SMILES: Cn1cc(NC(=O)c2csc3ncc(N4CCCNCC4)nc23)c(C(F)F)n1 ; O=C(O)C(F)(F)F] | 2-(1,4-diazepan-1-yl)-N-[3-(difluoromethyl)-1-methyl-1H-pyrazol-4-yl]thieno[2,3-b]pyrazine-7-carboxamide trifluoroacetate | Calc'd 408.1, found 408.4 |
| 15 | 4 | 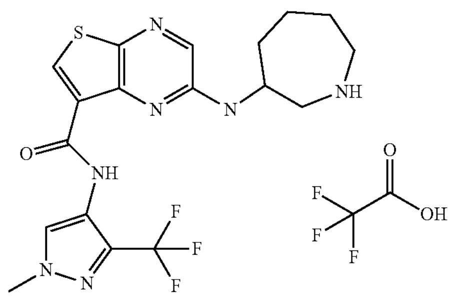 [SMILES: Cn1cc(NC(=O)c2csc3ncc(NC4CCCCNC4)nc23)c(C(F)(F)F)n1 ; O=C(O)C(F)(F)F] | 2-(azepan-3-ylamino)-N-[1-methyl-3-(trifluoromethyl)-1H-pyrazol-4-yl]thieno[2,3-b]pyrazine-7-carboxamide trifluoroacetate | Calc'd 440.1, found 440.4 |
| 16 | 73 | 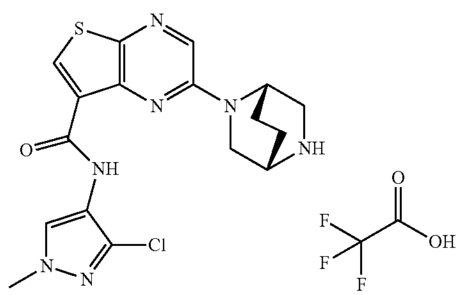 [SMILES: Cn1cc(NC(=O)c2csc3ncc(N4C[C@@H]5CC[C@H]4CN5)nc23)c(Cl)n1 ; O=C(O)C(F)(F)F] | N-(3-chloro-1-methyl-1H-pyrazol-4-yl)-2-[(1S,4S)- or (1R,4R)-2,5-diazabicyclo[2.2.2]oct-2-yl]thieno[2,3-b]pyrazine-7-carboxamide trifluoroacetate | Calc'd 404.1, found 404.4 |
| 17 | 15 | 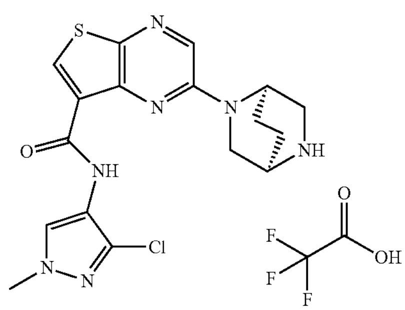 | N-(3-chloro-1-methyl-1H-pyrazol-4-yl)-2-[(1S,4S)- or (1R,4R)-2,5-diazabicyclo[2.2.2]oct-2-yl]thieno[2,3-b]pyrazine-7-carboxamide trifluoroacetate | Calc'd 404.1, found 404.4 |
| 18 | 14 | 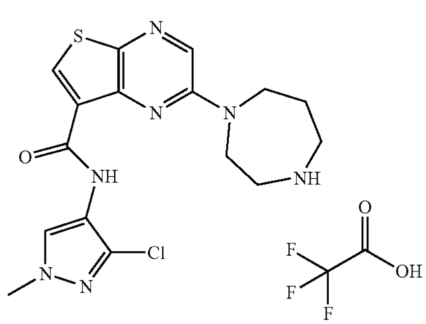 [SMILES: Cn1cc(NC(=O)c2csc3ncc(N4CCCNCC4)nc23)c(Cl)n1 ; O=C(O)C(F)(F)F] | N-(3-chloro-1-methyl-1H-pyrazol-4-yl)-2-(1,4-diazepan-1-yl)thieno[2,3-b]pyrazine-7-carboxamide trifluoroacetate | Calc'd 392.0, found 392.4 |

| Example # | IRAK4 IC$_{50}$ (nM) | Structure | IUPAC Name | Exact Mass [M + H]$^+$ |
|---|---|---|---|---|
| 19 | 70 | 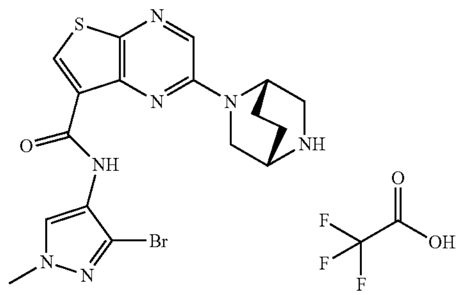 [SMILES: Cn1cc(NC(=O)c2csc3ncc(N4C[C@@H]5CC[C@H]4CN5)nc23)c(Br)n1 ; O=C(O)C(F)(F)F] | N-(3-bromo-1-methyl-1H-pyrazol-4-yl)-2-[(1S,4S)- or (1R,4R)-2,5-diazabicyclo[2.2.2]oct-2-yl]thieno[2,3-b]pyrazine-7-carboxamide trifluoroacetate | Calc'd 448.0, found 448.2 |
| 20 | 19 | 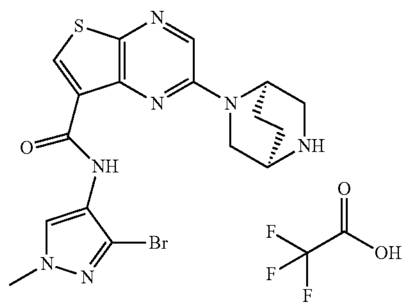 | N-(3-bromo-1-methyl-1H-pyrazol-4-yl)-2-[(1S,4S)- or (1R,4R)-2,5-diazabicyclo[2.2.2]oct-2-yl]thieno[2,3-b]pyrazine-7-carboxamide trifluoroacetate | Calc'd 448.0, found 448.4 |
| 21 | 15 | 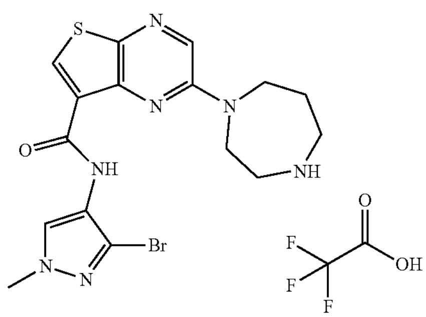 | N-(3-bromo-1-methyl-1H-pyrazol-4-yl)-2-(1,4-diazepan-1-yl)thieno[2,3-b]pyrazine-7-carboxamide trifluoroacetate | Calc'd 436.1, found 436.2 |
| 22 | 7 | 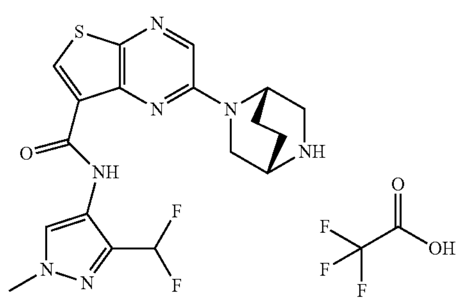 [SMILES: Cn1cc(NC(=O)c2csc3ncc(N4C[C@@H]5CC[C@H]4CN5)nc23)c(C(F)F)n1 ; O=C(O)C(F)(F)F] | 2-[(1S,4S)- or (1R,4R)-2,5-diazabicyclo[2.2.2]oct-2-yl]-N-[3-(difluoromethyl)-1-methyl-1H-pyrazol-4-yl]thieno[2,3-b]pyrazine-7-carboxamide trifluoroacetate | Calc'd 420.1, found 420.4 |
| 23 | 1 | 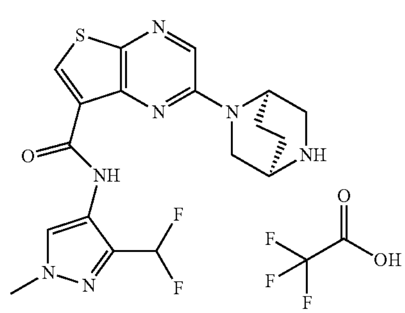 | 2-[(1S,4S)- or (1R,4R)-2,5-diazabicyclo[2.2.2]oct-2-yl]-N-[3-(difluoromethyl)-1-methyl-1H-pyrazol-4-yl]thieno[2,3-b]pyrazine-7-carboxamide trifluoroacetate | Calc'd 420.1, found 420.4 |

| Example # | IRAK4 IC$_{50}$ (nM) | Structure | IUPAC Name | Exact Mass [M + H]$^+$ |
|---|---|---|---|---|
| 24 | 0.2 | 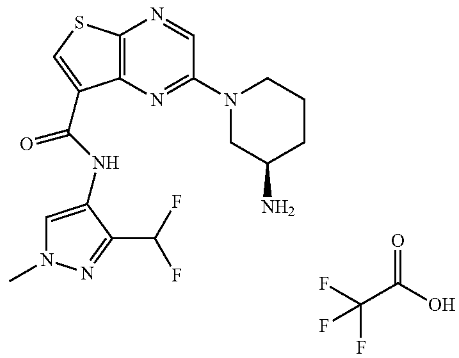 [SMILES: Cn1cc(NC(=O)c2csc3ncc(N4CCC[C@@H](N)C4)nc23)c(C(F)F)n1 ; O=C(O)C(F)(F)F] | 2[(3R)-3-aminopiperidin-1-yl] N-[3-(difluoromethyl)-1-methyl-1H-pyrazol-4-yl]thieno[2,3-b]pyrazine-7-carboxamide trifluoroacetate | Calc'd 408.1, found 408.4 |
| 25 | 0.2 | 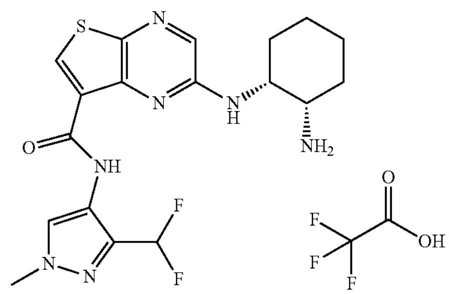 [SMILES: Cn1cc(NC(=O)c2csc3ncc(N[C@@H]4CCCC[C@@H]4N)nc23)c(C(F)F)n1 ; O=C(O)C(F)(F)F] | 2-{[(1R,2S)-2-aminocyclohexyl]amino}-N-[3-(difluoromethyl)-1-methyl-1H-pyrazol-4-yl]thieno[2,3-b]pyrazine-7-carboxamide trifluoroacetate | Calc'd 422.2, found 422.4 |
| 26 | 46 | 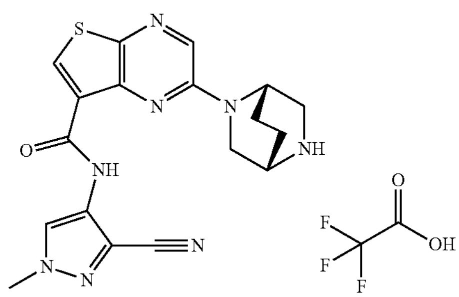 [SMILES: Cn1cc(NC(=O)c2csc3ncc(N4C[C@@H]5CC[C@H]4CN5)nc23)c(C#N)n1 ; O=C(O)C(F)(F)F] | N-(3-cyano-1-methyl-1H-pyrazol-4-yl)-2-[(1S,4S)- or (1R,4R)-2,5-diazabicyclo[2.2.2]oct-2-yl]thieno[2,3-b]pyrazine-7-carboxamide trifluoroacetate | Calc'd 395.1, found 395.4 |
| 27 | 37 | 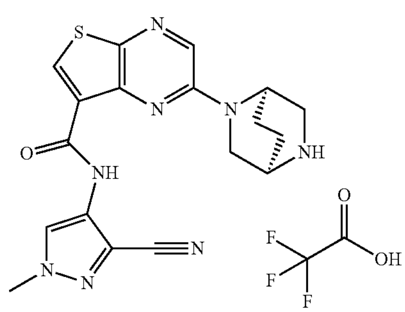 | N-(3-cyano-1-methyl-1H-pyrazol-4-yl)-2-[(1S,4S)- or (1R,4R)-2,5-diazabicyclo[2.2.2]oct-2-yl]thieno[2,3-b]pyrazine-7-carboxamide trifluoroacetate | Calc'd 395.1, found 395.4 |
| 28 | 26 | 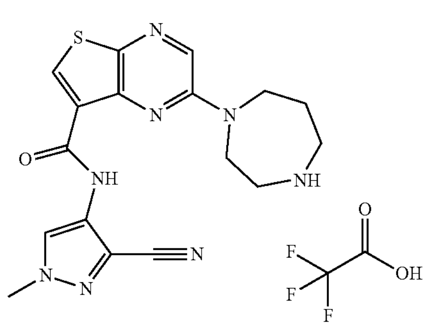 [SMILES: Cn1cc(NC(=O)c2csc3ncc(N4CCCNCC4)nc23)c(C#N)n1 ; O=C(O)C(F)(F)F] | N-(3-cyano-1-methyl-1H-pyrazol-4-yl)-2-(1,4-diazepan-1-yl)thieno[2,3-b]pyrazine-7-carboxamide trifluoroacetate | Calc'd 383.1, found 383.4 |

| Example # | IRAK4 IC$_{50}$ (nM) | Structure | IUPAC Name | Exact Mass [M + H]$^+$ |
|---|---|---|---|---|
| 29 | 107 | 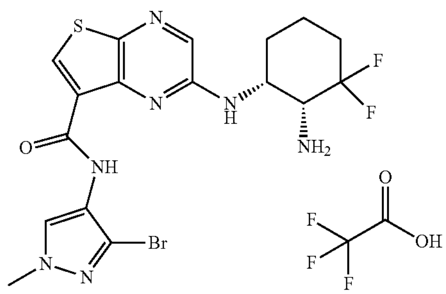 [SMILES: Cn1cc(NC(=O)c2csc3ncc(N[C@@H]4CCCC(F)(F)[C@@H]4N)nc23)c(Br)n1 ; O=C(O)C(F)(F)F] | 2-{[(1R,2R)-2-amino-3,3-difluorocyclohexyl]amino}-N-(3-(bromo-1-methyl-1H-pyrazol-4-yl)thieno[2,3-b]pyrazine-7-carboxamide trifluoroacetate | Calc'd 486.1, found 486.2 |
| 30 | 0.6 | 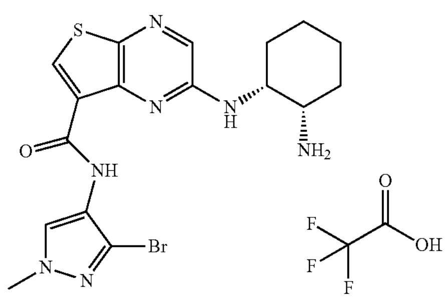 | 2-{[(1R,2S)-2-aminocyclohexyl]amino}-N-(3-bromo-1-methyl-1H-pyrazol-4-yl)thieno[2,3-b]pyrazine-7-carboxamide trifluoroacetate | Calc'd 450.1, found 450.2 |
| 31 | 7 | 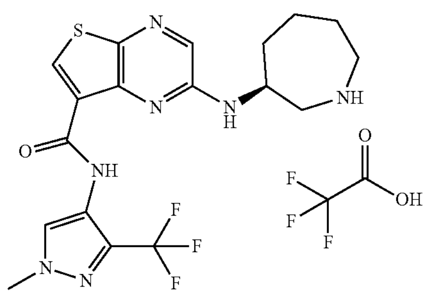 | 2-[(3S)- or (3R)-azepan-3-ylamino]-N-[1-methyl-3-(trifluoromethyl)-1H-pyrazol-4-yl]thieno[2,3-b]pyrazine-7-carboxamide trifluoroacetate | Calc'd 440.1, found 440.2 |
| 32 | 0.4 | 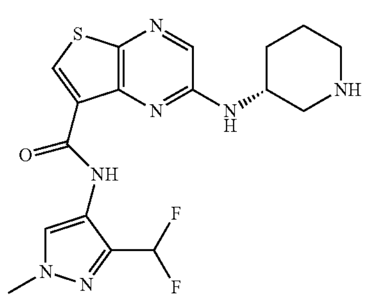 [SMILES: Cn1cc(NC(=O)c2csc3ncc(N[C@@H]4CCCNC4)nc23)c(C(F)F)n1] | N-[3-(difluoromethyl)-1-methyl-1H-pyrazol-4-yl]-2-[(3R)-piperidin-3-ylamino]thieno[2,3-b]pyrazine-7-carboxamide | Calc'd 408.1, found 408.2 |
| 33 | 0.2 | 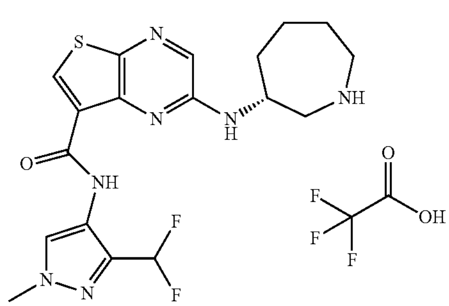 [SMILES: Cn1cc(NC(=O)c2csc3ncc(N[C@@H]4CCCCNC4)nc23)c(C(F)F)n1 ; O=C(O)C(F)(F)F] | 2-[(3S)- or (3R)-azepan-3-ylamino]-N-[3-(difluoromethyl)-1-methyl-1H-pyrazol-4-yl]thieno[2,3-b]pyrazine-7-carboxamide trifluoroacetate | Calc'd 422.2, found 422.2 |

-continued

| Example # | IRAK4 IC$_{50}$ (nM) | Structure | IUPAC Name | Exact Mass [M + H]$^+$ |
|---|---|---|---|---|
| 34 | 2 | 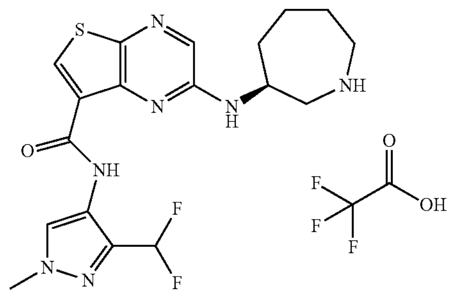 [SMILES: Cn1cc(NC(=O)c2csc3ncc(N[C@H]4CCCCNC4)nc23)c(C(F)F)n1 ; O=C(O)C(F)(F)F] | 2-[(3S)- or (3R)-azepan-3-ylamino]-N-[3-(difluoromethyl)-1-methyl-1H-pyrazol-4-yl]thieno[2,3-b]pyrazine-7-carboxamide trifluoroacetate | Calc'd 422.2, found 422.4 |
| 35 | 0.3 | 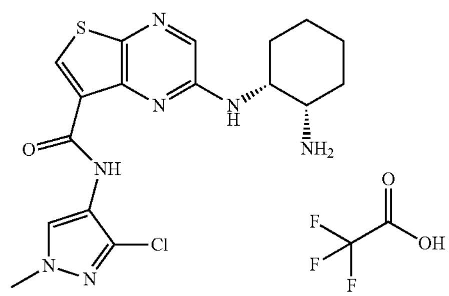 [SMILES: Cn1cc(NC(=O)c2csc3ncc(N[C@@H]4CCCC[C@@H]4N)nc23)c(Cl)n1 ; O=C(O)C(F)(F)F] | 2-{[(1R,2S)-2-aminocyclohexyl]amino}-N-(3-chloro-1-methyl-1H-pyrazol-4-yl)thieno[2,3-b]pyrazine-7-carboxamide trifluoroacetate | Calc'd 406.1, found 406.4 |
| 36 | 50 | 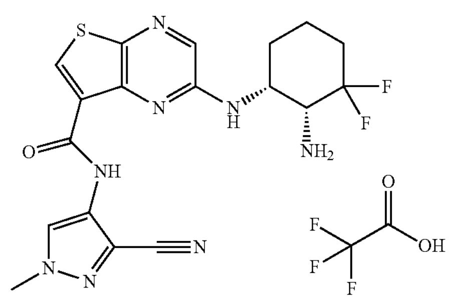 [SMILES: Cn1cc(NC(=O)c2csc3ncc(N[C@@H]4CCCC(F)(F)[C@@H]4N)nc23)c(C#N)n1 ; O=C(O)C(F)(F)F] | 2-{[(1R,2R)-2-amino-3,3-difluorocyclohexyl]amino}-N-(3-cyano-1-methyl-1H-pyrazol-4-yl)thieno[2,3-b]pyrazine-7-carboxamide trifluoroacetate | Calc'd 433.1, found 433.4 |
| 37 | 0.4 | 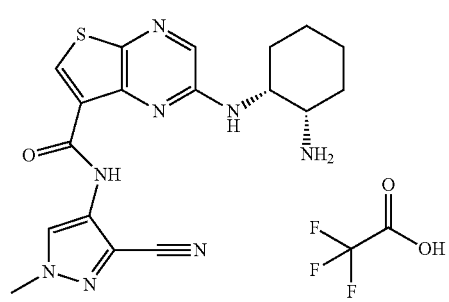 [SMILES: Cn1cc(NC(=O)c2csc3ncc(N[C@@H]4CCCC[C@@H]4N)nc23)c(C#N)n1 ; O=C(O)C(F)(F)F] | 2-{[(1R,2S)-2-aminocyclohexyl]amino}-N-(3-cyano-1-methyl-1H-pyrazol-4-yl)thieno[2,3-b]pyrazine-7-carboxamide trifluoroacetate | Calc'd 397.2, found 397.4 |
| 38 | 0.6 | 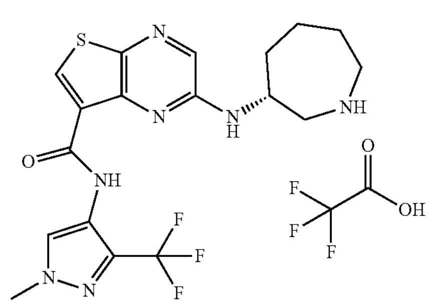 | 2-[(3S)- or (3R)-azepan-3-ylamino]-N-[1-methyl-3-(trifluoromethyl)-1H-pyrazol-4-yl]thieno[2,3-b]pyrazine-7-carboxamide trifluoroacetate | Calc'd 440.1, found 440.2 |

-continued

| Example # | IRAK4 IC$_{50}$ (nM) | Structure | IUPAC Name | Exact Mass [M + H]$^+$ |
|---|---|---|---|---|
| 39 | 32 | 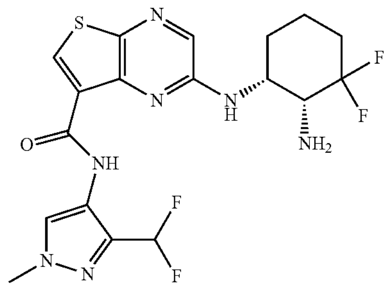 [SMILES: Cn1cc(NC(=O)c2csc3ncc(N[C@@H]4CCCC(F)(F)[C@@H]4N)nc23)c(C(F)F)n1] | 2-{[(1R,2R)-2-amino-3,3-difluorocyclohexyl]amino}-N-[3-(difluoromethyl)-1-methyl-1H-pyrazol-4-yl]thieno[2,3-b]pyrazine-7-carboxamide | Calc'd 458.1, found 458.0 |
| 40 | 0.6 | 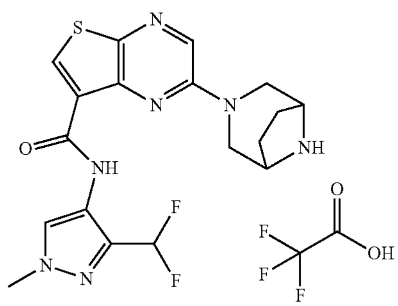 | 2-(3,8-diazabicyclo[3.2.1]oct-3-yl)-N-[3-(difluoromethyl)-1-methyl-1H-pyrazol-4-yl]thieno[2,3-b]pyrazine-7-carboxamide trifluoroacetate | Calc'd 420.1, found 420.4 |
| 41 | 18 | 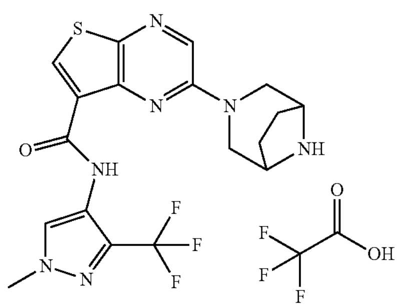 | 2-(3,8-diazabicyclo[3.2.1]oct-3-yl)-N-[1-methyl-3-(trifluoromethyl)-1H-pyrazol-4-yl]thieno[2,3-b]pyrazine-7-carboxamide trifluoroacetate | Calc'd 438.1, found 438.4 |
| 42 | 16 | 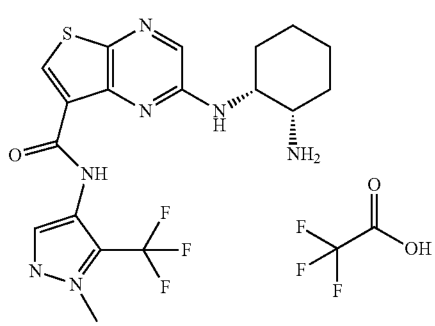 | 2-{[(1R,2S)-2-aminocyclohexyl]amino}-N-(1-methyl-5-(trifluoromethyl)-1H-pyrazol-4-yl]thieno[2,3-b]pyrazine-7-carboxamide trifluoroacetate | Calc'd 440.1, found 440.4 |
| 43 | 64 | 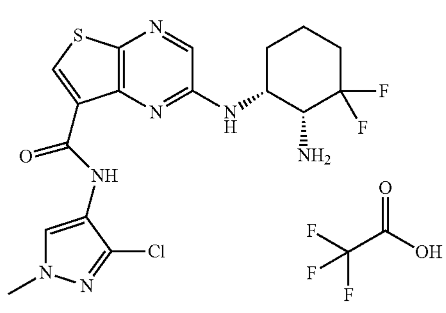 [SMILES: Cn1cc(NC(=O)c2csc3ncc(N[C@@H]4CCCC(F)(F)[C@@H]4N)nc23)c(Cl)n1 ; O=C(O)C(F)(F)F] | 2-{[(1R,2R)-2-amino-3,3-difluorocyclohexyl]amino}-N-(3-chloro-1-methyl-1H-pyrazol-4-yl)thieno[2,3-b]pyrazine-7-carboxamide trifluoroacetate | Calc'd 442.1, found 442.4 |

-continued

| Example # | IRAK4 IC$_{50}$ (nM) | Structure | IUPAC Name | Exact Mass [M + H]$^+$ |
|---|---|---|---|---|
| 44 | 0.5 | 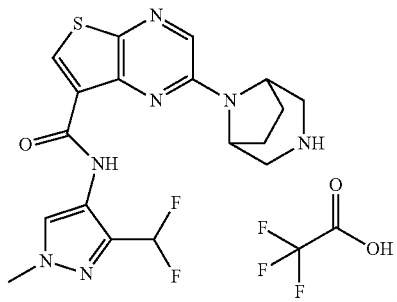 | 2-(3,8-diazabicyclo[3.2.1]oct-8-yl)-N-[3-(difluoromethyl)-1-methyl-1H-pyrazol-4-yl]thieno[2,3-b]pyrazine-7-carboxamide trifluoroacetate | Calc'd 420.1, found 420.4 |
| 45 | 2 | 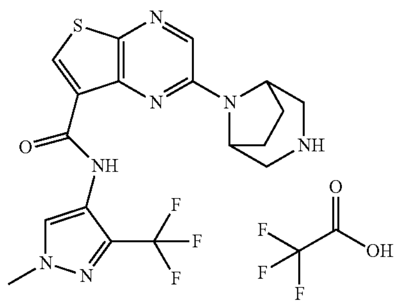 | 2-(3,8-diazabicyclo[3.2.1]oct-8-yl)-N-[1-methyl-3-(trifluoromethyl)-1H-pyrazol-4-yl]thieno[2,3-b]pyrazine-7-carboxamide trifluoroacetate | Calc'd 438.1, found 438.4 |
| 46 | 812 | 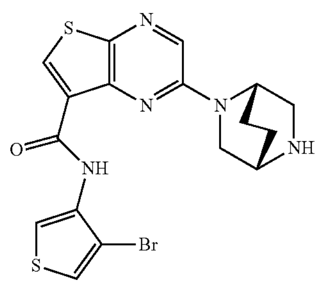 [SMILES: O=C(Nc1cscc1Br)c1csc2ncc(N3C[C@@H]4CC[C@H]3CN4)nc12] | N-(4-bromothiophen-3-yl)-2-[(1S,4S)- or (1R,4R)-2,5-diazabicyclo[2.2.2]oct-2-yl]thieno[2,3-b]pyrazine-7-carboxamide | 450.0 |
| 47 | 38 | 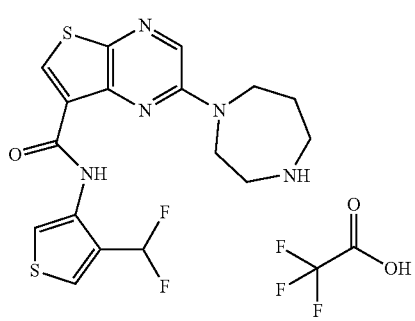 [SMILES: O=C(Nc1cscc1C(F)F)c1csc2ncc(N3CCCNCC3)nc12 ; O=C(O)C(F)(F)F] | 2-(1,4-diazepan-1-yl)-N-[4-(difluoromethyl)thiophen-3-yl]thieno[2,3-b]pyrazine-7-carboxamide trifluoroacetate | Calc'd 410.1, found 410.4 |
| 48 | 346 | 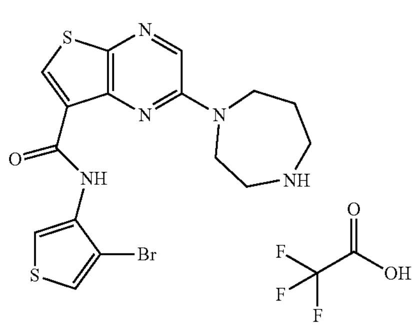 [SMILES: O=C(Nc1cscc1Br)c1csc2ncc(N3CCCNCC3)nc12 ; O=C(O)C(F)(F)F] | N-(4-bromothiophen-3-yl)-2-(1,4-diazepan-1-yl)thieno[2,3-b]pyrazine-7-carboxamide trifluoroacetate | Calc'd 438.1, found 438.2 |

| Example # | IRAK4 IC$_{50}$ (nM) | Structure | IUPAC Name | Exact Mass [M + H]$^+$ |
|---|---|---|---|---|
| 49 | 213 | 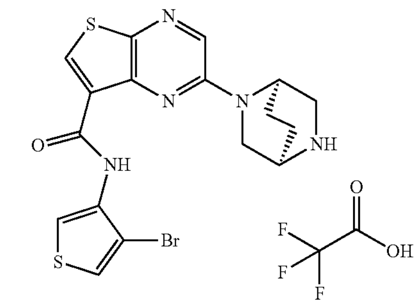 | N-(4-bromothiophen-3-yl)-2-[(1S,4S)- or (1R,4R)-2,5-diazabicyclo[2.2.2]oct-2-yl]thieno[2,3-b]pyrazine-7-carboxamide trifluoroacetate | Calc'd 450.0, found 450.2 |
| 50 | 0.7 | 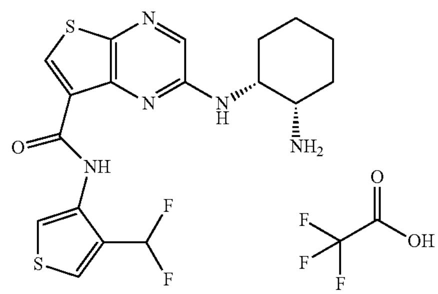 [SMILES: N[C@H]1CCCC[C@H]1Nc1cnc2scc(C(=O)Nc3cscc3C(F)F)c2n1 ; O=C(O)C(F)(F)F] | 2-{[(1R,2S)-2-aminocyclohexyl]amino}-N-(4-(difluoromethyl)thiophen-3-yl]thieno[2,3-b]pyrazine-7-carboxamide trifluoroacetate | Calc'd 424.1, found 424.4 |
| 51 | 1161 | 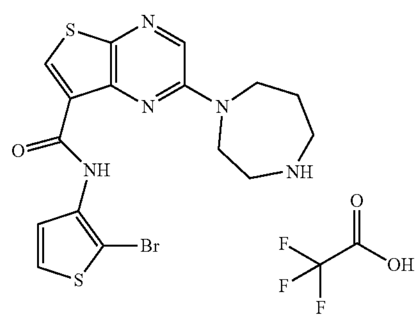 [SMILES: O=C(Nc1ccsc1Br)c1csc2ncc(N3CCCNCC3)nc12 ; O=C(O)C(F)(F)F] | N-(2-bromothiophen-3-yl)-2-(1,4-diazepan-1-yl)thieno[2,3-b]pyrazine-7-carboxamide trifluoroacetate | Calc'd 438.1, found 438.2 |
| 52 | 585 | 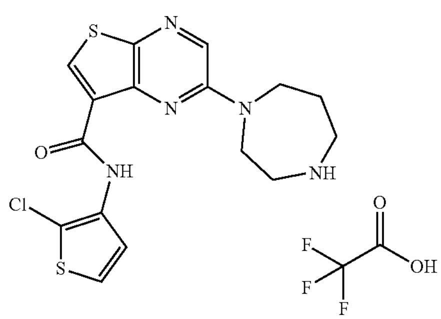 [SMILES: O=C(Nc1ccsc1Cl)c1csc2ncc(N3CCCNCC3)nc12 ; O=C(O)C(F)(F)F] | N-(2-chlorothiophen-3-yl)-2-(1,4-diazepan-1-yl)thieno[2,3-b]pyrazine-7-carboxamide trifluoroacetate | Calc'd 394.1, found 394.4 |
| 53 | 0.6 | 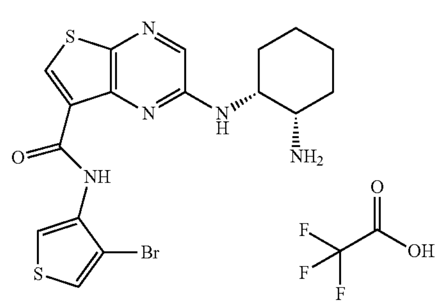 [SMILES: N[C@H]1CCCC[C@H]1Nc1cnc2scc(C(=O)Nc3cscc3Br)c2n1 ; O=C(O)C(F)(F)F] | 2-{[(1R,2S)-2-amino-cyclohexyl]amino}-N-(4-bromothiophen-3-yl)thieno[2,3-b]pyrazine-7-carboxamide trifluoroacetate | Calc'd 452.0, found 452.0 |

| Example # | IRAK4 IC$_{50}$ (nM) | Structure | IUPAC Name | Exact Mass [M + H]$^+$ |
|---|---|---|---|---|
| 54 | 1 | 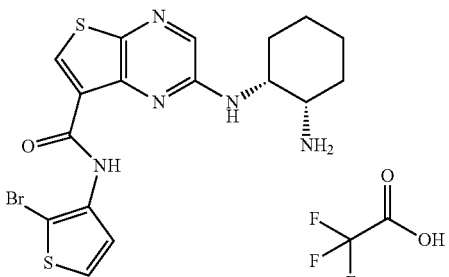 | 2-{[(1R,2S)-2-amino-cyclohexyl]amino}-N-(2-bromothiophen-3-yl)thieno[2,3-b]pyrazine-7-carboxamide trifluoroacetate | Calc'd 452.0, found 452.2 |
| 55 | 189 | 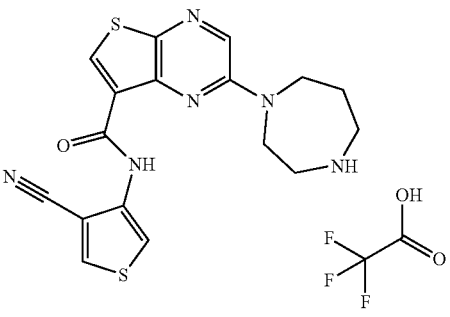 | N-(4-cyanothiophen-3-yl)-2-(1,4-diazepan-1-yl)thieno[2,3-b]pyrazine-7-carboxamide trifluoroacetate | Calc'd 385.1, found 385.4 |
| 56 | 0.6 | 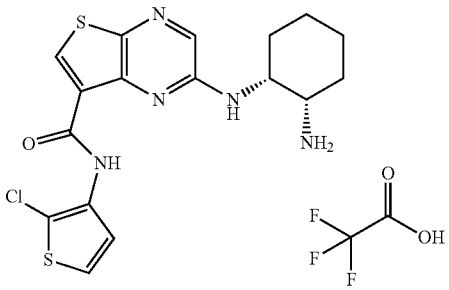 [SMILES: N[C@H]1CCCC[C@H]1Nc1cnc2scc(C(=O)Nc3ccsc3Br)c2n1 ; O=C(O)C(F)(F)F] | 2-{[(1R,2S)-2-amino-cyclohexyl]amino}-N-(2-chlorothiophen-3-yl)thieno[2,3-b]pyrazine-7-carboxamide trifluoroacetate | Calc'd 408.1, found 408.2 |
| 57 | 0.5 | 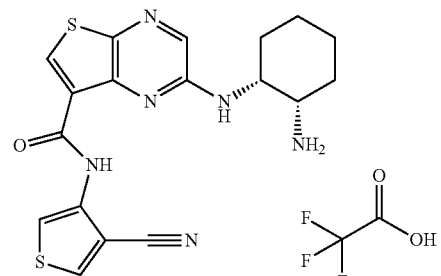 | 2-{[(1R,2S)-2-amino-cyclohexyl]amino}-N-(4-cyanothiophen-3-yl)thieno[2,3-b]pyrazine-7-carboxamide trifluoroacetate | Calc'd 399.1, found 399.2 |
| 58 | 285 | 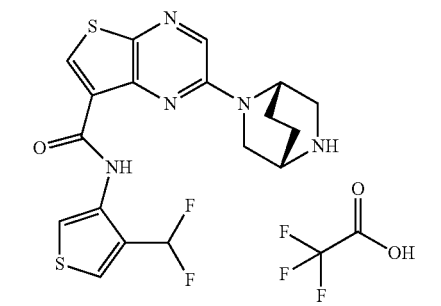 | 2-[(1S,4S)- or (1R,4R)-2,5-diazabicyclo[2.2.2]oct-2-yl]-N-[4-(difluoromethyl)thiophen-3-yl]thieno[2,3-b]pyrazine-7-carboxamide trifluoroacetate | Calc'd 422.1, found 422.4 |

-continued

| Example # | IRAK4 IC$_{50}$ (nM) | Structure | IUPAC Name | Exact Mass [M + H]$^+$ |
|---|---|---|---|---|
| 59 | 21 | 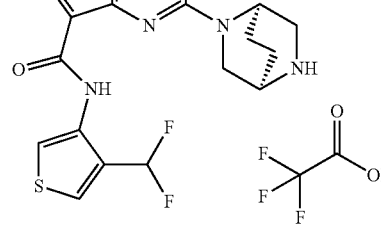 | 2-[(1S,4S)- or (1R,4R)-2,5-diazabicyclo[2.2.2]oct-2-yl]-N-[4-(difluoromethyl)thiophen-3-yl]thieno[2,3-b]pyrazine-7-carboxamide trifluoroacetate | Calc'd 422.1, found 422.4 |
| 60 | 1413 | 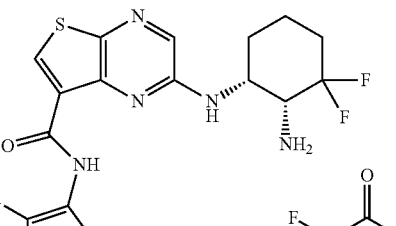 | 2-{[(1R,2R)-2-amino-3,3-difluorocyclohexyl]amino}-N-(2-chlorothiophen-3-yl)thieno[2,3-b]pyrazine-7-carboxamide trifluoroacetate | Calc'd 444.1, found 444.4 |
| 61 | 689 | 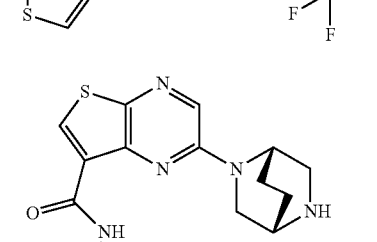 | N-(2-chlorothiophen-3-yl)-2-[(1S,4S)- or (1R,4R)-2,5-diazabicylo[2.2.2]oct-2-yl]thieno[2,3-b]pyrazine-7-carboxamide trifluoroacetate | Calc'd 406.1, found 406.4 |
| 62 | 274 | 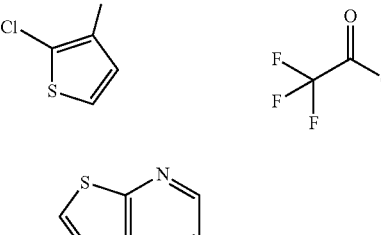 | N-(2-chlorothiophen-3-yl)-2-[(1S,4S)- or (1R,4R)-2,5-diazabicylo[2.2.2]oct-2-yl]thieno[2,3-b]pyrazine-7-carboxamide trifluoroacetate | Calc'd 406.1, found 406.4 |
| 63 | 324 | 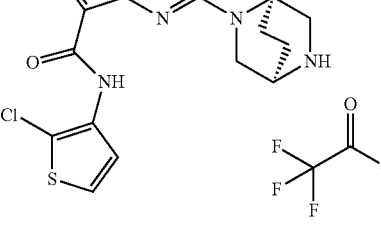 | N-(2-bromothiophen-3-yl)-2-[(1S,4S)- or (1R,4R)-2,5-diazabicylo[2.2.2]oct-2-yl]thieno[2,3-b]pyrazine-7-carboxamide trifluoroacetate | Calc'd 450.0, found 450.2 |

| Example # | IRAK4 IC$_{50}$ (nM) | Structure | IUPAC Name | Exact Mass [M + H]$^+$ |
|---|---|---|---|---|
| 64 | 767 | 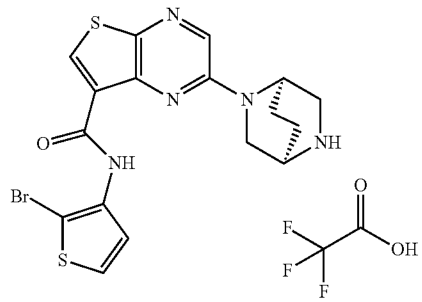 | N-(2-bromothiophen-3-yl)-2-[(1S,4S)- or (1R,4R)-2,5-diazabicylo[2.2.2]oct-2-yl]thieno[2,3-b]pyrazine-7-carboxamide trifluoroacetate | Calc'd 450.0, found 450.2 |
| 65 | 310 | 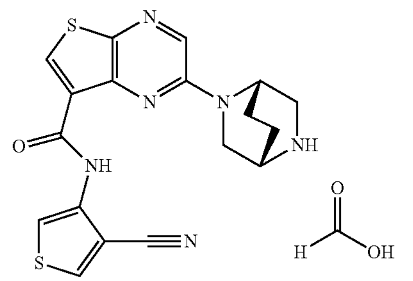 | N-(4-cyanothiophen-3-yl)-2-[(1S,4S)- or (1R,4R)-2,5-diazabicylo[2.2.2]oct-2-yl]thieno[2,3-b]pyrazine-7-carboxamide formate | Calc'd 397.1, found 397.4 |
| 66 | 220 | 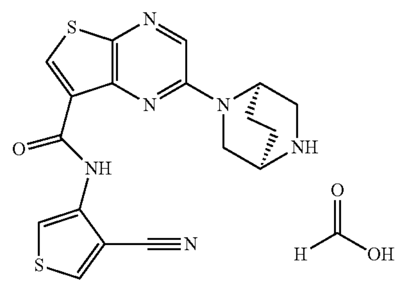 | N-(4-cyanothiophen-3-yl)-2-[(1S,4S)- or (1R,4R)-2,5-diazabicylo[2.2.2]oct-2-yl]thieno[2,3-b]pyrazine-7-carboxamide formate | Calc'd 397.1, found 397.2 |
| 67 | 330 | 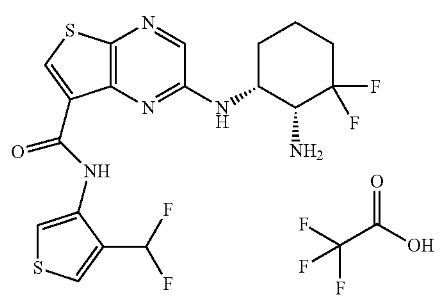 [SMILES: N[C@@H]1[C@H](Nc2cnc3scc(C(=O)Nc4cscc4C(F)F)c3n2)CCCC1(F)F ; O=C(O)C(F)(F)F] | 2-{[(1R,2R)-2-amino-3,3-difluorocyclohexyl]amino}-N-[4-(difluoromethyl)thiophen-3-yl]thieno[2,3-b]pyrazine-7-carboxamide trifluoroacetate | Calc'd 460.1, found 460.4 |
| 68 | 2100 | 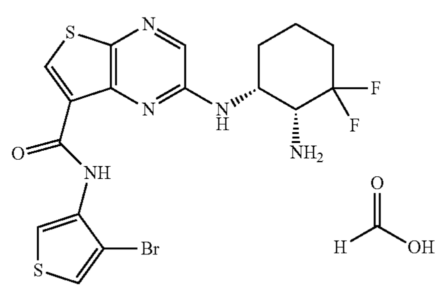 [SMILES: N[C@@H]1[C@H](Nc2cnc3scc(C(=O)Nc4cscc4Br)c3n2)CCCC1(F)F ; O=CO] | 2-{[(1R,2R)-2-amino-3,3-difluorocyclohexyl]amino}-N-(4-bromothiophen-3-yl)thieno[2,3-b]pyrazine-7-carboxamide formate | Calc'd 488.0, found 488.2 |

| Example # | IRAK4 IC$_{50}$ (nM) | Structure | IUPAC Name | Exact Mass [M + H]$^+$ |
|---|---|---|---|---|
| 69 | 228 | 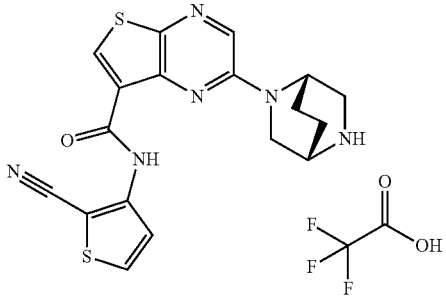 | N-(2-cyanothiophen-3-yl)-2-[(1S,4S)- or (1R,4R)-2,5-diazabicyclo[2.2.2]oct-2-yl]thieno[2,3-b]pyrazine-7-carboxamide trifluoroacetate | Calc'd 397.1, found 397.4 |
| 70 | 224 | 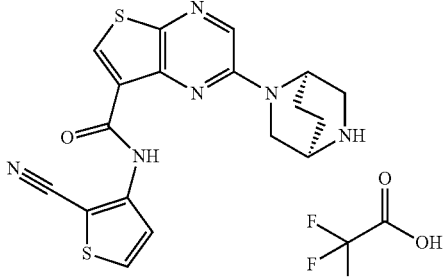 | N-(2-cyanothiophen-3-yl)-2-[(1S,4S)- or (1R,4R)-2,5-diazabicyclo[2.2.2]oct-2-yl]thieno[2,3-b]pyrazine-7-carboxamide trifluoroacetate | Calc'd 397.1, found 397.4 |
| 71 | 2069 | 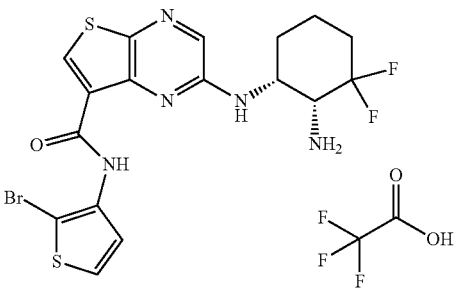 [SMILES: N[C@@H]1[C@H](Nc2cnc3scc(C(=O)Nc4ccsc4Br)c3n2)CCCC1(F)F ; O=C(O)C(F)(F)F] | 2-{[(1R,2R)-2-amino-3,3-difluorocyclohexyl]amino}-N-(2-bromothiophen-3-yl)thieno[2,3-b]pyrazine-7-carboxamide trifluoroacetate | Calc'd 488.0, found 488.2 |
| 72 | 422 | 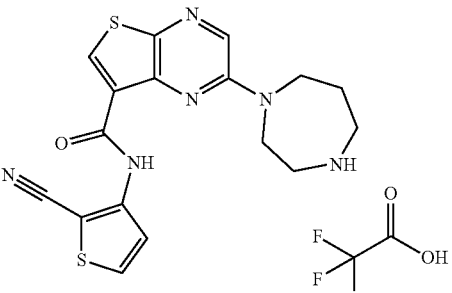 | N-(2-cyanothiophen-3-yl)-2-(1,4-diazepan-1-yl)thieno[2,3-b]pyrazine-7-carboxamide trifluoroacetate | Calc'd 385.1, found 385.4 |
| 73 | 1587 | 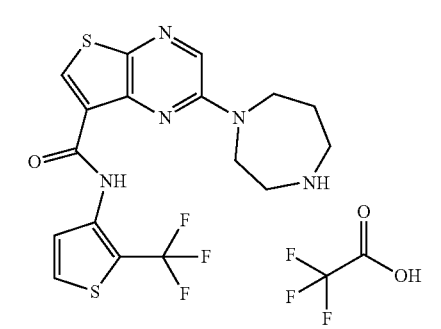 [SMILES: O=C(Nc1ccsc1C(F)(F)F)c1csc2ncc(N3CCCNCC3)nc12 ; O=C(O)C(F)(F)F] | 2-(1,4-diazepan-1-yl)-N-[2-(trifluoromethyl)thiophen-3-yl]thieno[2,3-b]pyrazine-7-carboxamide trifluoroacetate | Calc'd 428.1, found 428.2 |

-continued

| Example # | IRAK4 IC$_{50}$ (nM) | Structure | IUPAC Name | Exact Mass [M + H]$^+$ |
|---|---|---|---|---|
| 74 | 3653 | 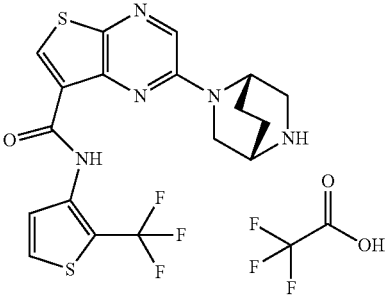 | 2-[(1S,4S)- or (1R,4R)-2,5-diazabicyclo[2.2.2]oct-2-yl]-N-[2-(trifluoromethyl)thiophen-3-yl]thieno[2,3-b]pyrazine-7-carboxamide trifluoroacetate | Calc'd 440.1, found 440.2 |
| 75 | 1231 | 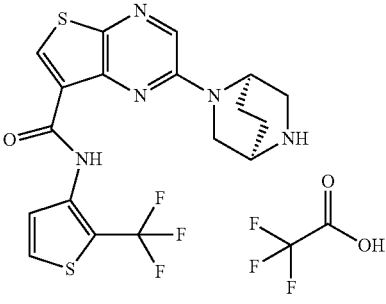 | 2-[(1S,4S)- or (1R,4R)-2,5-diazabicyclo[2.2.2]oct-2-yl]-N-[2-(trifluoromethyl)thiophen-3-yl]thieno[2,3-b]pyrazine-7-carboxamide trifluoroacetate | Calc'd 440.1, found 440.2 |
| 76 | 12 | 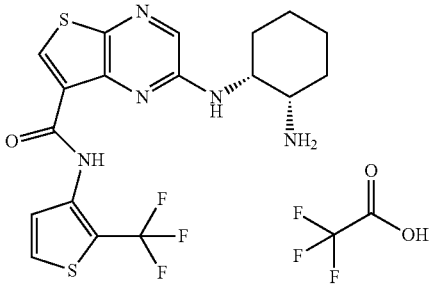 [SMILES: N[C@H]1CCCC[C@H]1Nc1cnc2scc(C(=O)Nc3ccsc3C(F)(F)F)c2n1 ; O=C(O)C(F)(F)F] | 2-{[(1R,2S)-2-aminocyclohexyl]amino}-N-(2-(trifluoromethyl)thiophen-3-yl]thieno[2,3-b]pyrazine-7-carboxamide trifluoroacetate | Calc'd 442.1, found 442.2 |
| 77 | 0.5 | 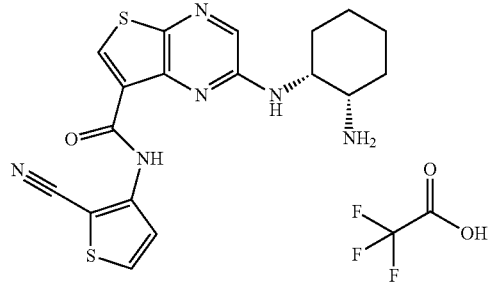 [SMILES: N#Cc1sccc1NC(=O)c1csc2ncc(N[C@@H]3CCCC[C@@H]3N)nc12 ; O=C(O)C(F)(F)F] | 2-{[(1R,2S)-2-aminocyclohexyl]amino}-N-(2-cyanothiophen-3-yl)thieno[2,3-b]pyrazine-7-carboxamide trifluoroacetate | Calc'd 399.1, found 399.0 |
| 78 | 3659 | 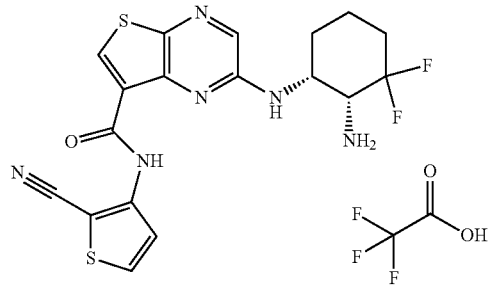 [SMILES: N#Cc1sccc1NC(=O)c1csc2ncc(N[C@@H]3CCCC(F)(F)[C@@H]3N)nc12 ; O=C(O)C(F)(F)F] | 2-{[(1R,2R)-2-amino-3,3-difluorocyclohexyl]amino}-N-(2-cyanothiophen-3-yl)thieno[2,3-b]pyrazine-7-carboxamide trifluoroacetate | Calc'd 435.1, found 435.2 |

| Example # | IRAK4 IC$_{50}$ (nM) | Structure | IUPAC Name | Exact Mass [M + H]$^+$ |
|---|---|---|---|---|
| 79 | 371 | 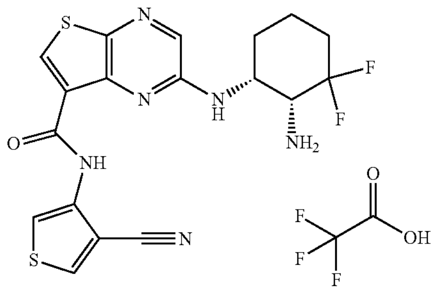 [SMILES: N#Cc1cscc1NC(=O)c1csc2ncc(N[C@@H]3CCCC(F)(F)[C@@H]3N)nc12 ; O=C(O)C(F)(F)F] | 2-{[(1R,2R)-2-amino-3,3-difluorocyclohexyl]amino}-N-(4-cyanothiophen-3-yl)thieno[2,3-b]pyrazine-7-carboxamide trifluoroacetate | Calc'd 435.1, found 435.2 |

Example 80

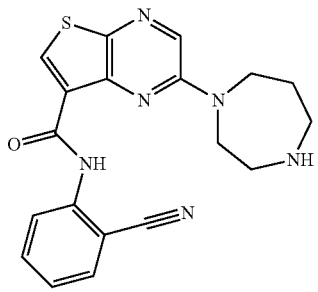 [SMILES: N#Cc1ccccc1NC(=O)c1csc2ncc(N3CCCNCC3)nc12]

N-(2-Cyanophenyl)-2-(1,4-diazepan-1-yl)thieno[2,3-b]pyrazine-7-carboxamide (IRAK4 IC$_{50}$=558 nM)

Step 1: Into a 25 mL round bottom flask containing a solution of 2-chlorothieno[2,3-b]pyrazine-7-carboxylic acid (500 mg, 2.1 mmol) in dichloromethane (10 mL) at 0° C. was added oxalyl chloride (0.5 mL, 11 mmol) followed by N,N-dimethylformamide (1 drop) and the reaction was stirred at room temperature for 1 h. The reaction mixture was concentrated to afford 2-chlorothieno[2,3-b]pyrazine-7-carbonyl chloride, which was taken to the next step without further purification.

Into a 10 mL round bottom flask charged with 2-aminobenzonitrile (0.38 g, 3.2 mmol) and N,N-diisopropylethylamine (0.5 mL, 6.4 mmol) in dichloromethane (3 mL) at 0° C. was added 2-chlorothieno[2,3-b]pyrazine-7-carbonyl chloride in dichloromethane (2 mL) dropwise and the reaction mixture was stirred at room temperature for 3 h. The reaction mixture was treated with ice cold water (4 mL) and extracted with dichloromethane (3×10 mL). The combined organics were washed with brine (20 mL) and dried over anhydrous sodium sulfate. The solution was filtered, concentrated under reduced pressure and purified by flash chromatography (silica gel) eluting with 20-30% ethyl acetate in petroleum ether to afford 2-chloro-N-(2-cyanophenyl)thieno[2,3-b]pyrazine-7-carboxamide as a solid. $^1$H NMR (CD$_3$OD, 400 MHz): δ 9.22 (s, 1H), 8.81 (s, 1H), 7.83-7.73 (m, 3H), 7.38 (t, J=7.6 Hz, 1H). MS calc'd [M+H]$^+$ 315.0, found 315.4.

Step 2: Into a 10 mL Pyrex tube containing a solution of 2-chloro-N-(2-cyanophenyl)thieno[2,3-b]pyrazine-7-carboxamide (50 mg, 0.15 mmol) in ethanol (2 mL) was added tert-butyl 1,4-diazepane-1-carboxylate (38 mg, 0.19 mmol) followed by N,N-diisopropylethylamine (0.1 mL, 0.48 mmol) and the reaction was heated at 140° C. for 16 h. The reaction mixture was cooled to room temperature, concentrated under reduced pressure and purified by flash chromatography (silica gel) eluting with 30-40% ethyl acetate in petroleum ether to afford tert-butyl 4-(7-((2-cyanophenyl)carbamoyl)thieno[2,3-b]pyrazin-2-yl)-1,4-diazepane-1-carboxylate as a liquid. MS calc'd [M+H]$^+$ 479.2, found 479.2.

Step 3: To a stirred solution of tert-butyl 4-(7-((2-cyanophenyl)carbamoyl)thieno[2,3-b]pyrazin-2-yl)-1,4-diazepane-1-carboxylate (50 mg, 0.1 mmol) in dichloromethane (3 mL) was added trifluoroacetic acid (0.3 mL) and the reaction mixture was stirred at room temperature for 2 h. The reaction mixture was concentrated under reduced pressure and purified by preparative HPLC to afford N-(2-cyanophenyl)-2-(1,4-diazepan-1-yl)thieno[2,3-b]pyrazine-7-carboxamide trifluoroacetate as a solid. $^1$H NMR (CD$_3$OD, 400 MHz): δ 8.93 (s, 1H), 8.46 (s, 1H), 8.10 (d, J=8.0 Hz, 1H), 7.83-7.74 (m, 2H), 7.40 (t, J=6.8 Hz, 1H), 4.27 (t, J=5.2 Hz, 2H), 4.04 (t, J=6.0 Hz, 2H), 3.55 (t, J=5.6 Hz, 2H), 3.38 (t, J=5.2 Hz, 2H), 2.30-2.25 (m, 2H). MS calc'd [M+H]$^+$ 379.1, found 379.4.

The following examples were prepared in an analogous manner of that described in Example 80.

| Example # | IRAK4 IC$_{50}$ (nM) | Structure | IUPAC Name | Exact Mass [M + H]$^+$ |
|---|---|---|---|---|
| 81 | 86 | 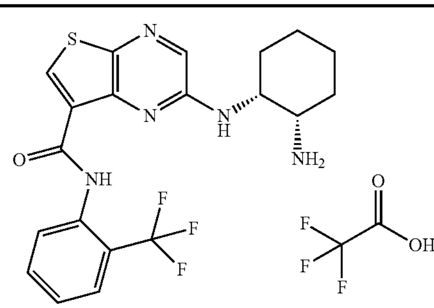 | 2-{[(1R,2S)-2-aminocyclohexyl]amino}-N-[2-(trifluoromethyl)phenyl]thieno[2,3-b]pyrazine-7-carboxamide trifluoroacetate | Calc'd 436.1, found 435.8 |

-continued

| Example # | IRAK4 IC₅₀ (nM) | Structure | IUPAC Name | Exact Mass [M + H]⁺ |
|---|---|---|---|---|
| 82 | 2338 | 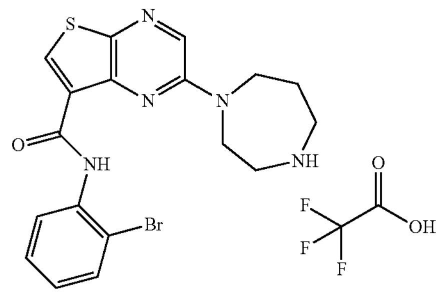 | N-(2-bromophenyl)-2-(1,4-diazepan-1-yl)thieno[2,3-b]pyrazine-7-carboxamide trifluoroacetate | Calc'd 432.0, found 432.2 |
| 83 | 899 | 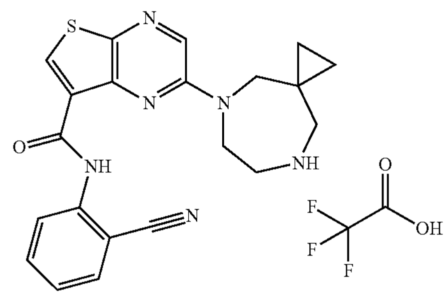 | N-(2-cyanophenyl)-2-(5,8-diazaspiro-[2.6]non-5-yl)-thieno[2,3-b]-pyrazine-7-carboxamide trifluoroacetate | Calc'd 405.1, found 405.4 |
| 84 | 33 | 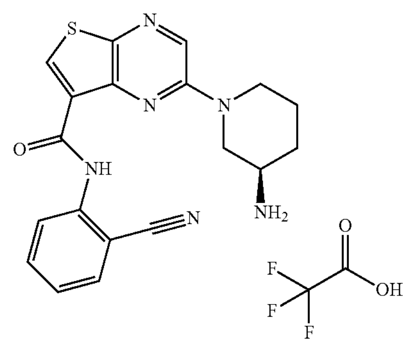 | 2-[(3R)-3-aminopiperidin-1-yl]-N-(2-cyanophenyl)-thieno[2,3-b]-pyrazine-7-carboxamide trifluoroacetate | Calc'd 379.1, found 379.4 |
| 85 | 2 | 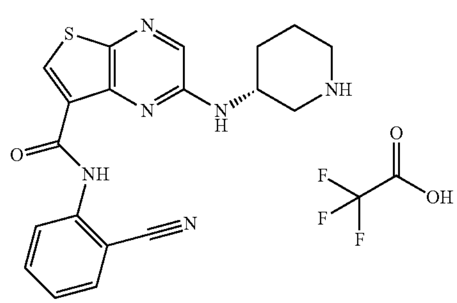 [SMILES: N#Cc1ccccc1NC(=O)c1csc2ncc(N[C@@H]3CCCNC3)nc12 ; O=C(O)C(F)(F)F] | N-(2-cyanophenyl)-2-[(3R)-piperidin-3-ylamino]-thieno[2,3-b]-pyrazine-7-carboxamide trifluoroacetate | Calc'd 379.1, found 379.4 |
| 86 | 292 | 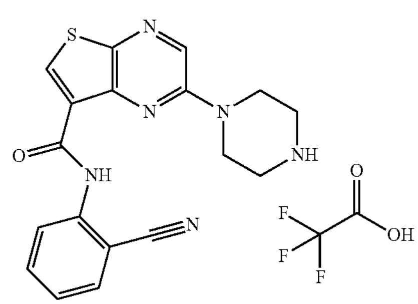 | N-(2-cyanophenyl)-2-piperazin-1-yl-thieno[2,3-b]-pyrazine-7-carboxamide trifluoroacetate | Calc'd 365.1, found 365.4 |

-continued

| Example # | IRAK4 IC$_{50}$ (nM) | Structure | IUPAC Name | Exact Mass [M + H]$^+$ |
|---|---|---|---|---|
| 87 | 2 | 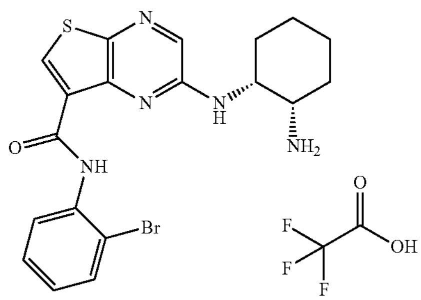 [SMILES: N[C@H]1CCCC[C@H]1Nc1cnc2scc(C(=O)Nc3ccccc3Br)c2n1 ; O=C(O)C(F)(F)F] | 2-{[(1R,2S)-2-aminocyclohexyl]-amino}-N-(2-bromophenyl)-thieno[2,3-b]-pyrazine-7-carboxamide trifluoroacetate | Calc'd 446.1, found 446.4 |
| 88 | 2872 | 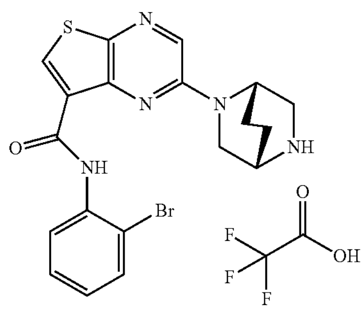 | N-(2-bromophenyl)-2-[(1S,4S)- or (1R,4R)-2,5-diazabicyclo-[2.2.2]oct-2-yl]thieno[2,3-b]-pyrazine-7-carboxamide trifluoroacetate | Calc'd 444.1, found 444.2 |
| 89 | 612 | 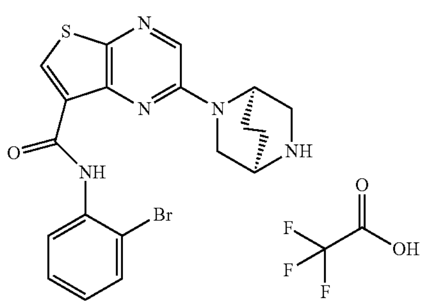 [SMILES: O=C(Nc1ccccc1Br)c1csc2ncc(N3C[C@H]4CC[C@@H]3CN4)nc12 ; O=C(O)C(F)(F)F] | N-(2-bromophenyl)-2-[(1S,4S)- or (1R,4R)-2,5-diazabicyclo-[2.2.2]oct-2-yl]thieno[2,3-b]-pyrazine-7-carboxamide trifluoroacetate | Calc'd 444.1, found 444.2 |
| 90 | 6395 | 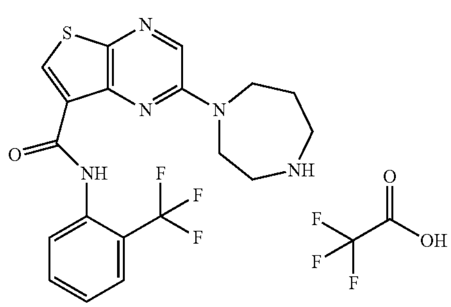 | 2-(1,4-diazepan-1-yl)-N-[2-(trifluoromethyl)phenyl]thieno[2,3-b]pyrazine-7-carboxamide trifluoroacetate | Calc'd 422.1, found 422.4 |
| 91 | 595 | 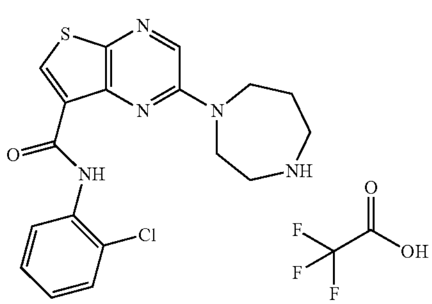 | N-(2-chlorophenyl)-2-(1,4-diazepan-1-yl)thieno[2,3-b]-pyrazine-7-carboxamide trifluoroacetate | Calc'd 388.1, found 388.4 |

-continued

| Example # | IRAK4 IC$_{50}$ (nM) | Structure | IUPAC Name | Exact Mass [M + H]$^+$ |
|---|---|---|---|---|
| 92 | 0.8 | 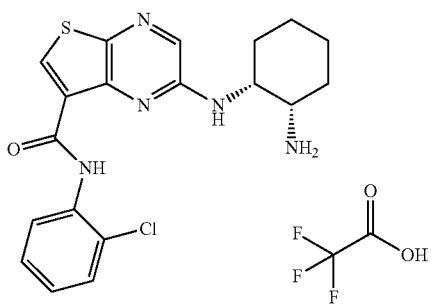 [SMILES: N[C@H]1CCCC[C@H]1Nc1cnc2scc(C(=O)Nc3ccccc3Cl)c2n1 ; O=C(O)C(F)(F)F] | 2-{(1R,2S)-2-aminocyclohexyl]-amino}-N-(2-chlorophenyl)-thieno[2,3-b]-pyrazine-7-carboxamide trifluoroacetate | Calc'd 402.1, found 402.4 |
| 93 | 4 | 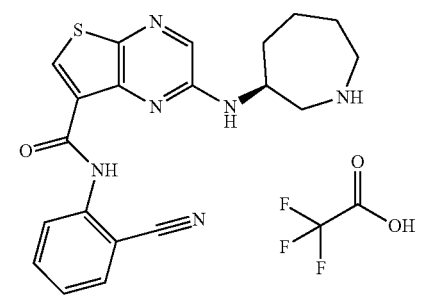 [SMILES: N#Cc1ccccc1NC(=O)c1csc2ncc(N[C@H]3CCCCNC3)nc12 ; O=C(O)C(F)(F)F] | 2-[(3S)- or (3R)-azepan-3-ylamino]-N-(2-cyanophenyl)-thieno[2,3-b]-pyrazine-7-carboxamide trifluoroacetate | Calc'd 393.1, found 393.4 |
| 94 | 9 | 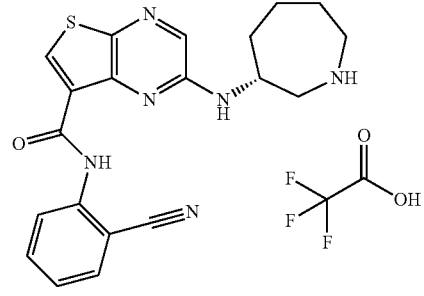 [SMILES: N#Cc1ccccc1NC(=O)c1csc2ncc(N[C@@H]3CCCCNC3)nc12 ; O=C(O)C(F)(F)F] | 2-[(3S)- or (3R)-azepan-3-ylamino]-N-(2-cyanophenyl)-thieno[2,3-b]-pyrazine-7-carboxamide trifluoroacetate | Calc'd 393.1, found 393.4 |
| 95 | 0.5 | 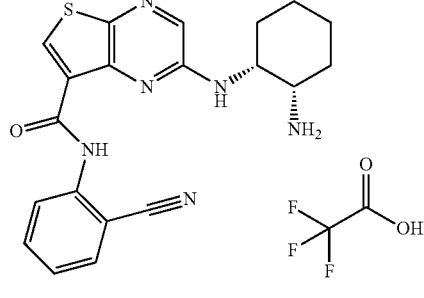 | 2-{[(1R,2S)-2-aminocyclohexyl]-amino}-N-(2-cyanophenyl)-thieno[2,3-b]-pyrazine-7-carboxamide trifluoroacetate | Calc'd 393.1, found 393.4 |
| 96 | 2011 | 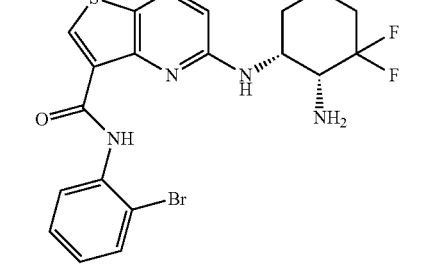 | 2-{[(1R,2R)-2-amino-3,3-difluorocyclo-hexyl]amino}-N-(2-bromo-phenyl)thieno-[2,3-b]-pyrazine-7-carboxamide | Calc'd 482.0, found 482.0 |

| Example # | IRAK4 IC$_{50}$ (nM) | Structure | IUPAC Name | Exact Mass [M + H]$^+$ |
|---|---|---|---|---|
| 97 | 173 | 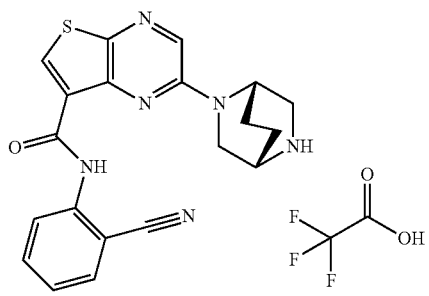 [SMILES: N#Cc1ccccc1NC(=O)c1csc2ncc(N3C[C@@H]4CC[C@H]3CN4)nc12 ; O=C(O)C(F)(F)F] | N-(2-cyanophenyl)-2-[(1S,4S)- or (1R,4R)-2,5-diazabicyclo-[2.2.2]oct-2-yl]thieno[2,3-b]-pyrazine-7-carboxamide trifluoroacetate | Calc'd 391.1, found 391.4 |
| 98 | 251 | 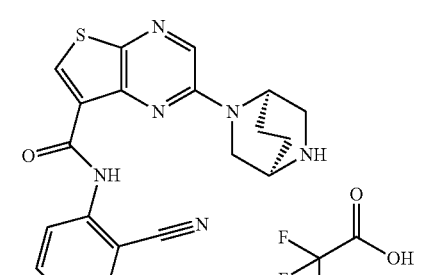 | N-(2-cyanophenyl)-2-[(1S,4S)- or (1R,4R)-2,5-diazabicyclo-[2.2.2]oct-2-yl]thieno[2,3-b]-pyrazine-7-carboxamide trifluoroacetate | Calc'd 391.1, found 391.4 |
| 99 | 1556 | 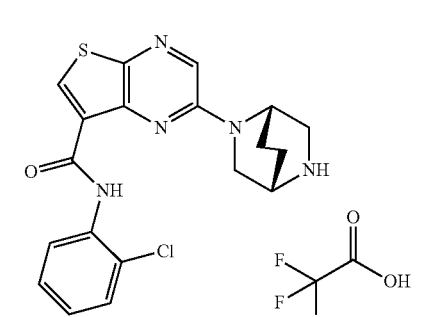 | N-(2-chlorophenyl)-2-[(1S,4S)- or (1R,4R)-2,5-diazabicyclo-[2.2.2]oct-2-yl]thieno[2,3-b]-pyrazine-7-carboxamide trifluoroacetate | Calc'd 400.1, found 400.4 |
| 100 | 191 | 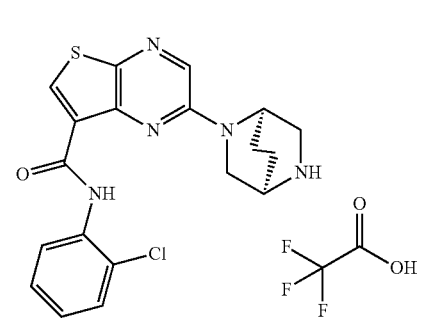 | N-(2-chlorophenyl)-2-[(1S,4S)- or (1R,4R)-2,5-diazabicyclo-[2.2.2]oct-2-yl]thieno[2,3-b]-pyrazine-7-carboxamide trifluoroacetate | Calc'd 400.1, found 400.4 |
| 101 | 545 | 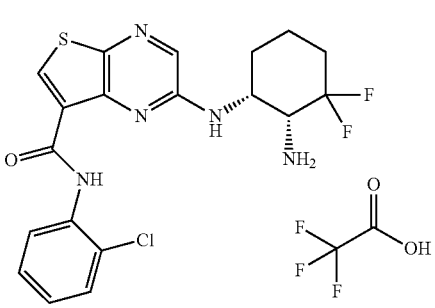 | 2-{[(1R,2R)-2-amino-3,3-difluorocyclohexyl]-amino}-N-(2-chlorophenyl)-thieno[2,3-b]-pyrazine-7-carboxamide trifluoroacetate | Calc'd 438.1, found 438.4 |

-continued

| Example # | IRAK4 IC₅₀ (nM) | Structure | IUPAC Name | Exact Mass [M + H]⁺ |
|---|---|---|---|---|
| 102 | 25 | 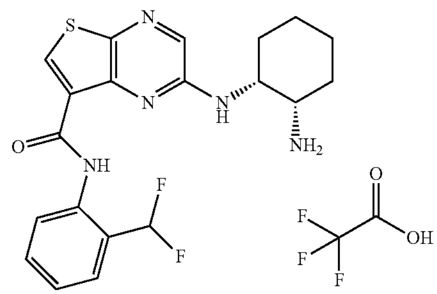 [SMILES: N[C@H]1CCCC[C@H]1Nc1cnc2scc(C(=O)Nc3ccccc3C(F)F)c2n1 ; O=C(O)C(F)(F)F] | 2-{[(1R,2S)-2-aminocyclohexyl]-amino}-N-[2-(difluoromethyl)phenyl]thieno-[2,3-b]-pyrazine-7-carboxamide trifluoroacetate | Calc'd 418.2, found 418.4 |
| 103 | 3630 | 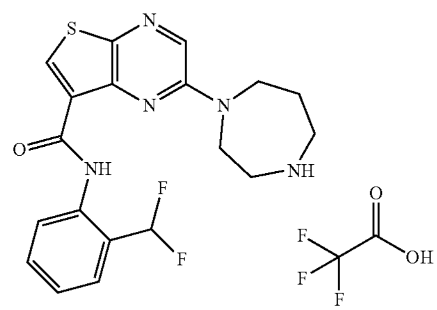 [SMILES: O=C(Nc1ccccc1C(F)F)c1csc2ncc(N3CCCNCC3)nc12 ; O=C(O)C(F)(F)F] | 2-(1,4-diazepan-1-yl)-N-[2-(difluoromethyl)phenyl]thieno[2,3-b]pyrazine-7-carboxamide trifluoroacetate | Calc'd 404.1, found 404.4 |
| 104 | 4180 | 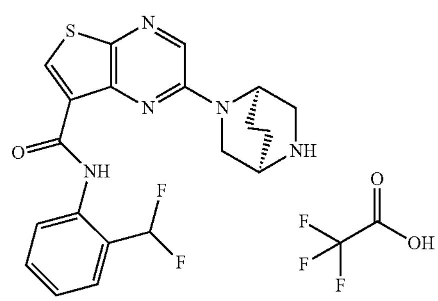 [SMILES: O=C(Nc1ccccc1C(F)F)c1csc2ncc(N3C[C@H]4CC[C@@H]3CN4)nc12 ; O=C(O)C(F)(F)F] | 2-[(1S,4S)- or (1R,4R)-2,5-diazabicyclo-[2.2.2]oct-2-yl]-N-[2-(difluoro-methyl)phenyl]-thieno[2,3-b]-pyrazine-7-carboxamide trifluoroacetate | Calc'd 416.1, found 416.2 |
| 105 | 146 | 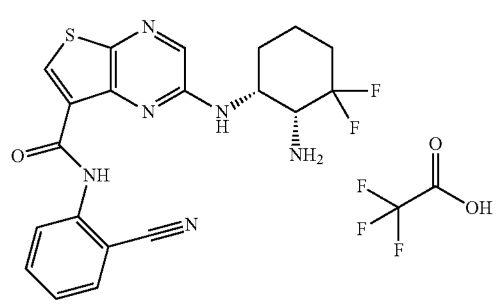 | 2-{[(1R,2R)-2-amino-3,3-difluorocyclohexyl]-amino}-N-(2-cyanophenyl)-thieno[2,3-b]-pyrazine-7-carboxamide trifluoroacetate | Calc'd 429.1, found 429.4 |
| 106 | 2583 | 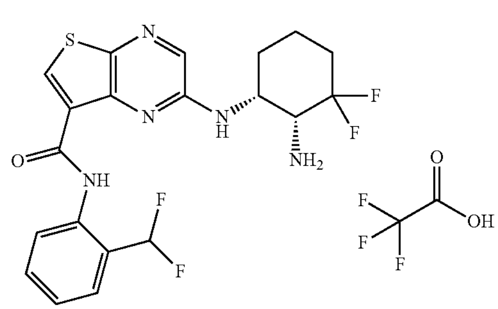 [SMILES: N[C@@H]1[C@H](Nc2cnc3scc(C(=O)Nc4ccccc4C(F)F)c3n2)CCCC1(F)F ; O=C(O)C(F)(F)F] | 2-{[(1R,2R)-2-amino-3,3-difluorocyclohexyl]-amino}-N-[2-(difluoromethyl)phenyl]thieno[2,3-b]pyrazine-7-carboxamide trifluoroacetate | Calc'd 454.1, found 454.4 |

| Example # | IRAK4 IC$_{50}$ (nM) | Structure | IUPAC Name | Exact Mass [M + H]$^+$ |
|---|---|---|---|---|
| 107 | 151 | 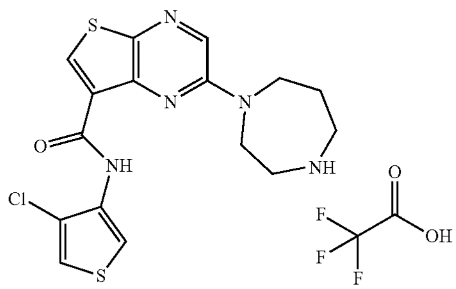 | N-(4-chlorothiophen-3-yl)-2-(1,4-diazepan-1-yl)-thieno[2,3-b]-pyrazine-7-carboxamide trifluoroacetate | Calc'd 394.1, found 394.2 |
| 108 | 307 | 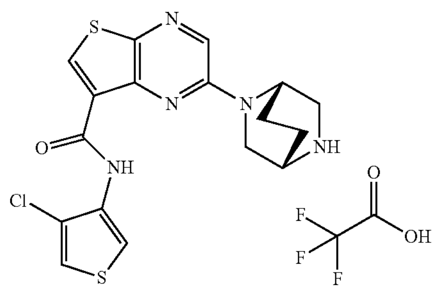 | N-(4-chlorothiophen-3-yl)-2-[(1S,4S)- or (1R,4R)-2,5-diazabicyclo-[2.2.2]oct-2-yl]-thieno[2,3-b]-pyrazine-7-carboxamide trifluoroacetate | Calc'd 406.1, found 406.2 |
| 109 | 104 | 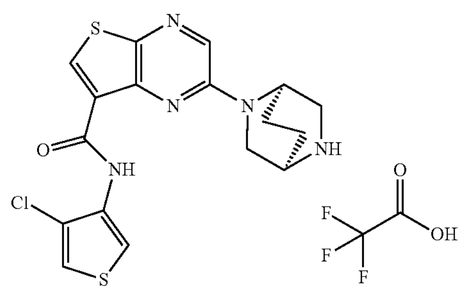 [SMILES: O=C(Nc1cscc1Cl)c1csc2ncc(N3C[C@H]4CC[C@@H]3CN4)nc12 ; O=C(O)C(F)(F)F] | N-(4-chlorothiophen-3-yl)-2-[(1S,4S)- or (1R,4R)-2,5-diazabicyclo-[2.2.2]oct-2-yl]-thieno[2,3-b]-pyrazine-7-carboxamide trifluoroacetate | Calc'd 406.1, found 406.2 |
| 110 | 0.7 | 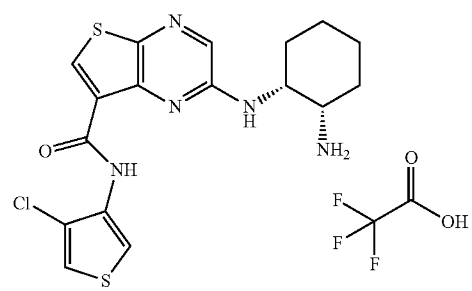 | 2-{[(1R,2S)-2-aminocyclohexyl]-amino}-N-(4-chlorothiophen-3-yl)thieno[2,3-b]-pyrazine-7-carboxamide trifluoroacetate | Calc'd 408.1, found 408.2 |
| 111 | 645 | 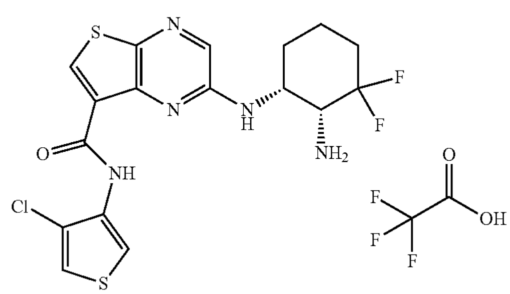 [SMILES: N[C@@H]1[C@H](Nc2cnc3scc(C(=O)Nc4cscc4Cl)c3n2)CCCC1(F)F ; O=C(O)C(F)(F)F] | 2-{[(1R,2R)-2-amino-3,3-difluorocyclohexyl]-amino}-N-(4-chlorothiophen-3-yl)thieno[2,3-b]-pyrazine-7-carboxamide trifluoroacetate | Calc'd 444.1, found 444.2 |

Biological Data

Compounds of the instant invention were tested by the assay described below and were found to have IRAK4 inhibitory activity. Data is shown in the representative table(s). Other assays are known in the literature and could be readily performed by those of skill in the art.

IRAK4 Kinase Assay

The kinase activity of IRAK4 is determined by its ability to catalyze the phosphorylation of a fluorescent polypeptide substrate. The extent of phosphorylation is measured using the IMAP technology (Molecular Devices) where the phosphorylated fluorescent substrate binds to the large M(III)-based nanoparticles which reduces the rotational speed of the substrate and thus increases its fluorescent polarization (FP).

20 µL reaction mixture contains 10 mM TriHCl, pH 7.2, 0.5 nM GST tagged IRAK4 (SignalChem), 100 nM fluorescent peptide substrate (RP7030, Molecular Devices), 100 µM ATP, 1 mM DDT, 1 mM MgCl$_2$, and 0.01% Tween 20. The reaction is initiated by the addition of ATP. After incubation for 30 minutes at 25° C., 60 µL of Progressive IMAP Reagent (Molecular Devices) is added to stop the reaction. Change in RP7030's FP is determined by a FP reader (Analyst HT, LJL BioSystems).

What is claimed is:

1. A compound according to Formula I:

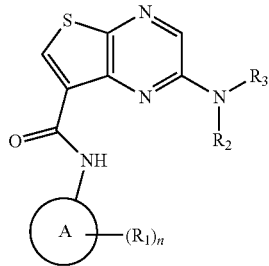

wherein:
Ring A is aryl or heterocyclyl;
n is 0, 1, 2, 3 or 4;
$R_1$ is independently selected from: (C$_1$-C$_4$)alkyl, (C$_3$-C$_6$)cycloalkyl, heterocyclyl, CN, halo, said alkyl, cycloalkyl and heterocyclyl optionally substituted with halo, OH, and OCH$_3$;
$R_2$ is H and $R_3$ is independently selected from: (C$_1$-C$_6$)alkyl, (C$_3$-C$_8$)cycloalkyl and heterocyclyl each optionally substituted with one or more halo, OH, N(R$_b$)$_2$, or morpholinyl, or $R_2$ and $R_3$ can be taken together with the nitrogen to which they are attached to form a heterocyclyl, said heterocyclyl optionally substituted with one or more substituents selected from R$_a$;
$R_a$ is independently selected from (C$_1$-C$_4$)alkyl, (C$_3$-C$_6$)cycloalkyl, CF$_3$, CHF$_2$, OH, halo and NH$_2$, said alkyl optionally substituted with (C$_3$-C$_6$)cycloalkyl and CF$_3$; and
$R_b$ is independently selected from H and (C$_1$-C$_4$)alkyl;
or a pharmaceutically acceptable salt thereof.

2. A compound according to claim 1 of Formula I: wherein:
Ring A is pyrazolyl, pyridinyl, thiophenyl, furanyl or phenyl;
n is 0, 1 or 2;
$R_1$ is independently selected from: (C$_1$-C$_4$)alkyl, cyclopropyl, oxadiazolyl, pyridinyl, oxazolyl, triazolyl, pyriminidyl, CN and halo, said alkyl, oxadiazolyl, pyridinyl, oxazolyl, triazolyl and pyriminidyl are optionally substituted with halo, OH, and OCH$_3$;
$R_2$ is H and $R_3$ is independently selected from: (C$_1$-C$_4$)alkyl, cyclohexyl, cycloheptyl, piperidinyl and azepanyl each optionally substituted with one or more F, OH, N(R$_b$)$_2$, or morpholinyl, or $R_2$ and $R_3$ can be taken together with the nitrogen to which they are attached to form a heterocyclyl selected from piperazinyl, diazepanyl, diazabicyclooctyl, diazabicycloheptyl, diazaspirononyl, hexahydropyrrolopyrazinyl, piperidinyl, diazabicyclononyl, oxadiazabicyclodecyl and diazatricyclodecyl, said heterocyclyl optionally substituted with one or more substituents selected from R$_a$;
$R_a$ is independently selected from (C$_1$-C$_4$)alkyl, cyclopropyl, CF$_3$, CHF$_2$, OH, F and NH$_2$, said alkyl optionally substituted with cyclopropyl and CF$_3$; and
$R_b$ is independently selected from H and methyl;
or a pharmaceutically acceptable salt thereof.

3. A compound which is selected from:
2-{[(1R,2S)-2-aminocyclohexyl]amino}-N-[1-methyl-3-(trifluoromethyl)-1H-pyrazol-4-yl]thieno[2,3-b]pyrazine-7-carboxamide;
N-[1-methyl-3-(trifluoromethyl)-1H-pyrazol-4-yl]-2-piperazin-1-ylthieno[2,3-b]pyrazine-7-carboxamide;
2-{[(1R,2S)-2-hydroxycyclohexyl]amino}-N-[1-methyl-3-(trifluoromethyl)-1H-pyrazol-4-yl]thieno[2,3-b]pyrazine-7-carboxamide;
N-[1-methyl-3-(trifluoromethyl)-1H-pyrazol-4-yl]-2-[(3R)-piperidin-3-ylamino]thieno[2,3-b]pyrazine-7-carboxamide;
2-{[(1R,2R)-2-amino-3,3-difluorocyclohexyl]amino}-N-[1-methyl-3-(trifluoromethyl)-1H-pyrazol-4-yl]thieno[2,3-b]pyrazine-7-carboxamide;
2-(1,4-diazepan-1-yl)-N-[1-methyl-3-(trifluoromethyl)-1H-pyrazol-4-yl]thieno[2,3-b]pyrazine-7-carboxamide;
2-(2,5-diazabicyclo[2.2.2]oct-2-yl)-N-[1-methyl-3-(trifluoromethyl)-1H-pyrazol-4-yl]thieno[2,3-b]pyrazine-7-carboxamide;
2-(5,8-diazaspiro[2.6]non-5-yl)-N-[1-methyl-3-(trifluoromethyl)-1H-pyrazol-4-yl]thieno[2,3-b]pyrazine-7-carboxamide;
2-[(3R)-3-aminopiperidin-1-yl]-N-[1-methyl-3-(trifluoromethyl)-1H-pyrazol-4-yl]thieno[2,3-b]pyrazine-7-carboxamide;
N-[3-(difluoromethyl)-1-methyl-1H-pyrazol-4-yl]-2-{[(1R,2S)-2-hydroxycyclohexyl]amino}thieno[2,3-b]pyrazine-7-carboxamide;
2-(2,5-diazabicyclo[2.2.2]oct-2-yl)-N-[3-(difluoromethyl)-1-methyl-1H-pyrazol-4-yl]thieno[2,3-b]pyrazine-7-carboxamide;
N-[3-(difluoromethyl)-1-methyl-1H-pyrazol-4-yl]-2-piperazin-1-ylthieno[2,3-b]pyrazine-7-carboxamide;
2-(5,8-diazaspiro[2.6]non-5-yl)-N-[3-(difluoromethyl)-1-methyl-1H-pyrazol-4-yl]thieno[2,3-b]pyrazine-7-carboxamide;
2-(1,4-diazepan-1-yl)-N-[3-(difluoromethyl)-1-methyl-1H-pyrazol-4-yl]thieno[2,3-b]pyrazine-7-carboxamide;
2-(azepan-3-ylamino)-N-[1-methyl-3-(trifluoromethyl)-1H-pyrazol-4-yl]thieno[2,3-b]pyrazine-7-carboxamide;
N-(3-chloro-1-methyl-1H-pyrazol-4-yl)-2-[(1S,4S)-2,5-diazabicyclo[2.2.2]oct-2-yl]thieno[2,3-b]pyrazine-7-carboxamide;
N-(3-chloro-1-methyl-1H-pyrazol-4-yl)-2-[(1R,4R)-2,5-diazabicyclo[2.2.2]oct-2-yl]thieno[2,3-b]pyrazine-7-carboxamide;
N-(3-chloro-1-methyl-1H-pyrazol-4-yl)-2-(1,4-diazepan-1-yl)thieno[2,3-b]pyrazine-7-carboxamide;

N-(3-bromo-1-methyl-1H-pyrazol-4-yl)-2-[(1S,4S)-2,5-diazabicyclo[2.2.2]oct-2-yl]thieno[2,3-b]pyrazine-7-carboxamide;

N-(3-bromo-1-methyl-1H-pyrazol-4-yl)-2-[(1R,4R)-2,5-diazabicyclo[2.2.2]oct-2-yl]thieno[2,3-b]pyrazine-7-carboxamide;

N-(3-bromo-1-methyl-1H-pyrazol-4-yl)-2-(1,4-diazepan-1-yl)thieno[2,3-b]pyrazine-7-carboxamide;

2-[(1S,4S)-2,5-diazabicyclo[2.2.2]oct-2-yl]-N-[3-(difluoromethyl)-1-methyl-1H-pyrazol-4-yl]thieno[2,3-b]pyrazine-7-carboxamide;

2-[(1R,4R)-2,5-diazabicyclo[2.2.2]oct-2-yl]-N-[3-(difluoromethyl)-1-methyl-1H-pyrazol-4-yl]thieno[2,3-b]pyrazine-7-carboxamide;

2-[(3R)-3-aminopiperidin-1-yl]-N-[3-(difluoromethyl)-1-methyl-1H-pyrazol-4-yl]thieno[2,3-b]pyrazine-7-carboxamide;

2-{[(1R,2S)-2-aminocyclohexyl]amino}-N-[3-(difluoromethyl)-1-methyl-1H-pyrazol-4-yl]thieno[2,3-b]pyrazine-7-carboxamide;

N-(3-cyano-1-methyl-1H-pyrazol-4-yl)-2-[(1S,4S)-2,5-diazabicyclo[2.2.2]oct-2-yl]thieno[2,3-b]pyrazine-7-carboxamide;

N-(3-cyano-1-methyl-1H-pyrazol-4-yl)-2-[(1R,4R)-2,5-diazabicyclo[2.2.2]oct-2-yl]thieno[2,3-b]pyrazine-7-carboxamide;

N-(3-cyano-1-methyl-1H-pyrazol-4-yl)-2-(1,4-diazepan-1-yl)thieno[2,3-b]pyrazine-7-carboxamide;

2-{[(1R,2R)-2-amino-3,3-difluorocyclohexyl]amino}-N-(3-bromo-1-methyl-1H-pyrazol-4-yl)thieno[2,3-b]pyrazine-7-carboxamide;

2-{[(1R,2S)-2-aminocyclohexyl]amino}-N-(3-bromo-1-methyl-1H-pyrazol-4-yl)thieno[2,3-b]pyrazine-7-carboxamide;

2-[(3S)-azepan-3-ylamino]-N-[1-methyl-3-(trifluoromethyl)-1H-pyrazol-4-yl]thieno[2,3-b]pyrazine-7-carboxamide;

N-[3-(difluoromethyl)-1-methyl-1H-pyrazol-4-yl]-2-[(3R)-piperidin-3-ylamino]thieno[2,3-b]pyrazine-7-carboxamide;

2-[(3R)-azepan-3-ylamino]-N-[3-(difluoromethyl)-1-methyl-1H-pyrazol-4-yl]thieno[2,3-b]pyrazine-7-carboxamide;

2-[(3S)-azepan-3-ylamino]-N-[3-(difluoromethyl)-1-methyl-1H-pyrazol-4-yl]thieno[2,3-b]pyrazine-7-carboxamide;

2-{[(1R,2S)-2-aminocyclohexyl]amino}-N-(3-chloro-1-methyl-1H-pyrazol-4-yl)thieno[2,3-b]pyrazine-7-carboxamide;

2-{[(1R,2R)-2-amino-3,3-difluorocyclohexyl]amino}-N-(3-cyano-1-methyl-1H-pyrazol-4-yl)thieno[2,3-b]pyrazine-7-carboxamide;

2-{[(1R,2S)-2-aminocyclohexyl]amino}-N-(3-cyano-1-methyl-1H-pyrazol-4-yl)thieno[2,3-b]pyrazine-7-carboxamide;

2-[(3R)-azepan-3-ylamino]-N-[1-methyl-3-(trifluoromethyl)-1H-pyrazol-4-yl]thieno[2,3-b]pyrazine-7-carboxamide;

2-{[(1R,2R)-2-amino-3,3-difluorocyclohexyl]amino}-N-[3-(difluoromethyl)-1-methyl-1H-pyrazol-4-yl]thieno[2,3-b]pyrazine-7-carboxamide;

2-(3,8-diazabicyclo[3.2.1]oct-3-yl)-N-[3-(difluoromethyl)-1-methyl-1H-pyrazol-4-yl]thieno[2,3-b]pyrazine-7-carboxamide;

2-(3,8-diazabicyclo[3.2.1]oct-3-yl)-N-[1-methyl-3-(trifluoromethyl)-1H-pyrazol-4-yl]thieno[2,3-b]pyrazine-7-carboxamide;

2-{[(1R,2S)-2-aminocyclohexyl]amino}-N-[1-methyl-5-(trifluoromethyl)-1H-pyrazol-4-yl]thieno[2,3-b]pyrazine-7-carboxamide;

2-{[(1R,2R)-2-amino-3,3-difluorocyclohexyl]amino}-N-(3-chloro-1-methyl-1H-pyrazol-4-yl)thieno[2,3-b]pyrazine-7-carboxamide;

2-(3,8-diazabicyclo[3.2.1]oct-8-yl)-N-[3-(difluoromethyl)-1-methyl-1H-pyrazol-4-yl]thieno[2,3-b]pyrazine-7-carboxamide;

2-(3,8-diazabicyclo[3.2.1]oct-8-yl)-N-[1-methyl-3-(trifluoromethyl)-1H-pyrazol-4-yl]thieno[2,3-b]pyrazine-7-carboxamide;

N-(4-bromothiophen-3-yl)-2-[(1S,4S)-2,5-diazabicyclo[2.2.2]oct-2-yl]thieno[2,3-b]pyrazine-7-carboxamide;

2-(1,4-diazepan-1-yl)-N-[4-(difluoromethyl)thiophen-3-yl]thieno[2,3-b]pyrazine-7-carboxamide;

N-(4-bromothiophen-3-yl)-2-(1,4-diazepan-1-yl)thieno[2,3-b]pyrazine-7-carboxamide;

N-(4-bromothiophen-3-yl)-2-[(1S,4S)-2,5-diazabicyclo[2.2.2]oct-2-yl]thieno[2,3-b]pyrazine-7-carboxamide;

2-{[(1R,2S)-2-aminocyclohexyl]amino}-N-[4-(difluoromethyl)thiophen-3-yl]thieno[2,3-b]pyrazine-7-carboxamide;

N-(2-bromothiophen-3-yl)-2-(1,4-diazepan-1-yl)thieno[2,3-b]pyrazine-7-carboxamide;

N-(2-chlorothiophen-3-yl)-2-(1,4-diazepan-1-yl)thieno[2,3-b]pyrazine-7-carboxamide;

2-{[(1R,2S)-2-aminocyclohexyl]amino}-N-(4-bromothiophen-3-yl)thieno[2,3-b]pyrazine-7-carboxamide;

2-{[(1R,2S)-2-aminocyclohexyl]amino}-N-(2-bromothiophen-3-yl)thieno[2,3-b]pyrazine-7-carboxamide;

N-(4-cyanothiophen-3-yl)-2-(1,4-diazepan-1-yl)thieno[2,3-b]pyrazine-7-carboxamide;

2-{[(1R,2S)-2-aminocyclohexyl]amino}-N-(2-chlorothiophen-3-yl)thieno[2,3-b]pyrazine-7-carboxamide;

2-{[(1R,2S)-2-aminocyclohexyl]amino}-N-(4-cyanothiophen-3-yl)thieno[2,3-b]pyrazine-7-carboxamide;

2-[(1S,4S)-2,5-diazabicyclo[2.2.2]oct-2-yl]-N-[4-(difluoromethyl)thiophen-3-yl]thieno[2,3-b]pyrazine-7-carboxamide;

2-[(1R,4R)-2,5-diazabicyclo[2.2.2]oct-2-yl]-N-[4-(difluoromethyl)thiophen-3-yl]thieno[2,3-b]pyrazine-7-carboxamide;

2-{[(1R,2R)-2-amino-3,3-difluorocyclohexyl]amino}-N-(2-chlorothiophen-3-yl)thieno[2,3-b]pyrazine-7-carboxamide;

N-(2-chlorothiophen-3-yl)-2-[(1S,4S)-2,5-diazabicyclo[2.2.2]oct-2-yl]thieno[2,3-b]pyrazine-7-carboxamide;

N-(2-chlorothiophen-3-yl)-2-[(1R,4R)-2,5-diazabicyclo[2.2.2]oct-2-yl]thieno[2,3-b]pyrazine-7-carboxamide;

N-(2-bromothiophen-3-yl)-2-[(1S,4S)-2,5-diazabicyclo[2.2.2]oct-2-yl]thieno[2,3-b]pyrazine-7-carboxamide;

N-(2-bromothiophen-3-yl)-2-[(1R,4R)-2,5-diazabicyclo[2.2.2]oct-2-yl]thieno[2,3-b]pyrazine-7-carboxamide;

N-(4-cyanothiophen-3-yl)-2-[(1S,4S)-2,5-diazabicyclo[2.2.2]oct-2-yl]thieno[2,3-b]pyrazine-7-carboxamide;

N-(4-cyanothiophen-3-yl)-2-[(1R,4R)-2,5-diazabicyclo[2.2.2]oct-2-yl]thieno[2,3-b]pyrazine-7-carboxamide;

2-{[(1R,2R)-2-amino-3,3-difluorocyclohexyl]amino}-N-[4-(difluoromethyl)thiophen-3-yl]thieno[2,3-b]pyrazine-7-carboxamide;

2-{[(1R,2R)-2-amino-3,3-difluorocyclohexyl]amino}-N-(4-bromothiophen-3-yl)thieno[2,3-b]pyrazine-7-carboxamide;

N-(2-cyanothiophen-3-yl)-2-[(1S,4S)-2,5-diazabicyclo[2.2.2]oct-2-yl]thieno[2,3-b]pyrazine-7-carboxamide;

N-(2-cyanothiophen-3-yl)-2-[(1R,4R)-2,5-diazabicyclo [2.2.2]oct-2-yl]thieno[2,3-b]pyrazine-7-carboxamide;
2-{[(1R,2R)-2-amino-3,3-difluorocyclohexyl]amino}-N-(2-bromothiophen-3-yl)thieno[2,3-b]pyrazine-7-carboxamide;
N-(2-cyanothiophen-3-yl)-2-(1,4-diazepan-1-yl)thieno[2,3-b]pyrazine-7-carboxamide;
2-(1,4-diazepan-1-yl)-N-[2-(trifluoromethyl)thiophen-3-yl]thieno[2,3-b]pyrazine-7-carboxamide;
2-[(1S,4S)-2,5-diazabicyclo[2.2.2]oct-2-yl]-N-[2-(trifluoromethyl)thiophen-3-yl]thieno[2,3-b]pyrazine-7-carboxamide;
2-[(1R,4R)-2,5-diazabicyclo[2.2.2]oct-2-yl]-N-[2-(trifluoromethyl)thiophen-3-yl]thieno[2,3-b]pyrazine-7-carboxamide;
2-{[(1R,2S)-2-aminocyclohexyl]amino}-N-[2-(trifluoromethyl)thiophen-3-yl]thieno[2,3-b]pyrazine-7-carboxamide;
2-{[(1R,2S)-2-aminocyclohexyl]amino}-N-(2-cyanothiophen-3-yl)thieno[2,3-b]pyrazine-7-carboxamide;
2-{[(1R,2R)-2-amino-3,3-difluorocyclohexyl]amino}-N-(2-cyanothiophen-3-yl)thieno[2,3-b]pyrazine-7-carboxamide;
2-{[(1R,2R)-2-amino-3,3-difluorocyclohexyl]amino}-N-(4-cyanothiophen-3-yl)thieno[2,3-b]pyrazine-7-carboxamide;
N-(2-cyanophenyl)-2-(1,4-diazepan-1-yl)thieno[2,3-b]pyrazine-7-carboxamide;
2-{[(1R,2S)-2-aminocyclohexyl]amino}-N-[2-(trifluoromethyl)phenyl]thieno[2,3-b]pyrazine-7-carboxamide;
N-(2-bromophenyl)-2-(1,4-diazepan-1-yl)thieno[2,3-b]pyrazine-7-carboxamide;
N-(2-cyanophenyl)-2-(5,8-diazaspiro[2.6]non-5-yl)thieno[2,3-b]pyrazine-7-carboxamide;
2-[(3R)-3-aminopiperidin-1-yl]-N-(2-cyanophenyl)thieno[2,3-b]pyrazine-7-carboxamide;
N-(2-cyanophenyl)-2-[(3R)-piperidin-3-ylamino]thieno[2,3-b]pyrazine-7-carboxamide;
N-(2-cyanophenyl)-2-piperazin-1-ylthieno[2,3-b]pyrazine-7-carboxamide;
2-{[(1R,2S)-2-aminocyclohexyl]amino}-N-(2-bromophenyl)thieno[2,3-b]pyrazine-7-carboxamide;
N-(2-bromophenyl)-2-[(1S,4S)-2,5-diazabicyclo[2.2.2]oct-2-yl]thieno[2,3-b]pyrazine-7-carboxamide;
N-(2-bromophenyl)-2-[(1R,4R)-2,5-diazabicyclo[2.2.2]oct-2-yl]thieno[2,3-b]pyrazine-7-carboxamide;
2-(1,4-diazepan-1-yl)-N-[2-(trifluoromethyl)phenyl]thieno[2,3-b]pyrazine-7-carboxamide;
N-(2-chlorophenyl)-2-(1,4-diazepan-1-yl)thieno[2,3-b]pyrazine-7-carboxamide;
2-{[(1R,2S)-2-aminocyclohexyl]amino}-N-(2-chlorophenyl)thieno[2,3-b]pyrazine-7-carboxamide;
2-[(3S)-azepan-3-ylamino]-N-(2-cyanophenyl)thieno[2,3-b]pyrazine-7-carboxamide;
2-[(3R)-azepan-3-ylamino]-N-(2-cyanophenyl)thieno[2,3-b]pyrazine-7-carboxamide;
2-{[(1R,2S)-2-aminocyclohexyl]amino}-N-(2-cyanophenyl)thieno[2,3-b]pyrazine-7-carboxamide;
2-{[(1R,2R)-2-amino-3,3-difluorocyclohexyl]amino}-N-(2-bromophenyl)thieno[2,3-b]pyrazine-7-carboxamide;
N-(2-cyanophenyl)-2-[(1S,4S)-2,5-diazabicyclo[2.2.2]oct-2-yl]thieno[2,3-b]pyrazine-7-carboxamide;
N-(2-cyanophenyl)-2-[(1R,4R)-2,5-diazabicyclo[2.2.2]oct-2-yl]thieno[2,3-b]pyrazine-7-carboxamide;
N-(2-chlorophenyl)-2-[(1S,4S)-2,5-diazabicyclo[2.2.2]oct-2-yl]thieno[2,3-b]pyrazine-7-carboxamide;
N-(2-chlorophenyl)-2-[(1R,4R)-2,5-diazabicyclo[2.2.2]oct-2-yl]thieno[2,3-b]pyrazine-7-carboxamide;
2-{[(1R,2R)-2-amino-3,3-difluorocyclohexyl]amino}-N-(2-chlorophenyl)thieno[2,3-b]pyrazine-7-carboxamide;
2-{[(1R,2S)-2-aminocyclohexyl]amino}-N-[2-(difluoromethyl)phenyl]thieno[2,3-b]pyrazine-7-carboxamide;
2-(1,4-diazepan-1-yl)-N-[2-(difluoromethyl)phenyl]thieno[2,3-b]pyrazine-7-carboxamide;
2-[(1R,4R)-2,5-diazabicyclo[2.2.2]oct-2-yl]-N-[2-(difluoromethyl)phenyl]thieno[2,3-b]pyrazine-7-carboxamide;
2-{[(1R,2R)-2-amino-3,3-difluorocyclohexyl]amino}-N-(2-cyanophenyl)thieno[2,3-b]pyrazine-7-carboxamide;
2-{[(1R,2R)-2-amino-3,3-difluorocyclohexyl]amino}-N-[2-(difluoromethyl)phenyl]thieno[2,3-b]pyrazine-7-carboxamide;
N-(4-chlorothiophen-3-yl)-2-(1,4-diazepan-1-yl)thieno[2,3-b]pyrazine-7-carboxamide;
N-(4-chlorothiophen-3-yl)-2-[(1S,4S)-2,5-diazabicyclo[2.2.2]oct-2-yl]thieno[2,3-b]pyrazine-7-carboxamide;
N-(4-chlorothiophen-3-yl)-2-[(1R,4R)-2,5-diazabicyclo[2.2.2]oct-2-yl]thieno[2,3-b]pyrazine-7-carboxamide;
2-{[(1R,2S)-2-aminocyclohexyl]amino}-N-(4-chlorothiophen-3-yl)thieno[2,3-b]pyrazine-7-carboxamide; and
2-{[(1R,2R)-2-amino-3,3-difluorocyclohexyl]amino}-N-(4-chlorothiophen-3-yl)thieno[2,3-b]pyrazine-7-carboxamide;
or a pharmaceutically acceptable salt thereof.

4. A pharmaceutical composition comprising a pharmaceutical carrier and a therapeutically effective amount of a compound of claim 1.

* * * * *